(12) United States Patent
Hubschwerlen et al.

(10) Patent No.: US 9,029,368 B2
(45) Date of Patent: May 12, 2015

(54) 3,7-DISUBSTITUTED OCTAHYDRO-2H-PYRIDO[4,3-E][1,3] OXAZIN-2-ONE ANTIBIOTICS

(71) Applicant: Actelion Pharmaceuticals Ltd., Allschwil (CH)

(72) Inventors: Christian Hubschwerlen, Durmenach (FR); Georg Rueedi, Allschwil (CH); Jean-Philippe Surivet, Kembs (FR); Cornelia Zumbrunn Acklin, Basel (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 14/362,026

(22) PCT Filed: Nov. 29, 2012

(86) PCT No.: PCT/IB2012/056829
§ 371 (c)(1),
(2) Date: May 30, 2014

(87) PCT Pub. No.: WO2013/080156
PCT Pub. Date: Jun. 6, 2013

(65) Prior Publication Data
US 2014/0309218 A1    Oct. 16, 2014

(30) Foreign Application Priority Data

Nov. 30, 2011   (WO) .................. PCT/IB2011/055383

(51) Int. Cl.
C07D 498/04      (2006.01)
A61K 31/5383     (2006.01)
C07D 513/04      (2006.01)

(52) U.S. Cl.
CPC ............ *C07D 498/04* (2013.01); *C07D 513/04* (2013.01)

(58) Field of Classification Search
USPC .......................................... 544/91; 514/230.5
See application file for complete search history.

(56) References Cited

U.S. PATENT DOCUMENTS

| 7,888,359 B2 | 2/2011  | Hubschwerlen et al. |
| 7,999,115 B2 | 8/2011  | Hubschwerlen et al. |
| 8,114,867 B2 | 2/2012  | Gude et al. |
| 8,349,826 B2 | 1/2013  | Hubschwerlen et al. |
| 8,349,828 B2 | 1/2013  | Hubschwerlen et al. |
| 8,618,092 B2 | 12/2013 | Hubschwerlen et al. |

FOREIGN PATENT DOCUMENTS

| WO | 00/78748      | 12/2000 |
| WO | 02/08224      | 1/2002  |
| WO | 02/056882     | 7/2002  |
| WO | 02/089749     | 11/2002 |
| WO | 03/050132     | 6/2003  |
| WO | 2004/009562   | 1/2004  |
| WO | 2004/058144   | 7/2004  |
| WO | 2005/000838   | 1/2005  |
| WO | 2005/016916   | 2/2005  |
| WO | 2005/108389   | 11/2005 |
| WO | 2006/002047   | 1/2006  |
| WO | 2006/021448   | 3/2006  |
| WO | 2006/032466   | 3/2006  |
| WO | 2006/105289   | 10/2006 |
| WO | 2006/137485   | 12/2006 |
| WO | 2007/016610   | 2/2007  |
| WO | 2007/071936   | 6/2007  |
| WO | 2007/081597   | 7/2007  |
| WO | 2007/100758   | 9/2007  |
| WO | 2007/107905   | 9/2007  |
| WO | 2007/107965   | 9/2007  |
| WO | 2007/138974   | 12/2007 |
| WO | 2008/003690   | 1/2008  |
| WO | 2008/009700   | 1/2008  |
| WO | 2008/026172   | 3/2008  |
| WO | 2008/125594   | 10/2008 |
| WO | 2008/126024   | 10/2008 |
| WO | 2009/009700   | 1/2009  |
| WO | 2009/069589   | 6/2009  |
| WO | 2009/071890   | 6/2009  |
| WO | 2009/104147   | 8/2009  |
| WO | 2009/104159   | 8/2009  |
| WO | 2010/030782   | 3/2010  |
| WO | 2010/041194   | 4/2010  |
| WO | 2011/057892   | 5/2011  |

OTHER PUBLICATIONS

Snyder et al., PubMed Abstract (J. Med. Liban 48(4): 208-214, Jul.-Aug. 2000.*
Adams E.P. et al., "Dialkylaminoalkylquinolines," J. Chem. Soc. (1957), pp. 3066-3071.
Gijsen, H.J.M. et al., "Development of Two Diastereoselective Routes Towards trans-4-aminomethyl-piperidin-3-ol Building Blocks," Tetrahedron (2008), vol. 64, pp. 2456-2464.
Gould, Philip, "Salt selection for basic drugs," International Journal of Pharmaceutics (1986), vol. 33, pp. 201-217.
Greene, T. W. et al., "Protection for the Amino Group," in Protecting Groups in Organic Synthesis (3rd Edition,1999), pp. 494-653.
(Continued)

*Primary Examiner* — Kahsay Habte
(74) *Attorney, Agent, or Firm* — Hunton & Williams LLP

(57) ABSTRACT

The invention relates to antibacterial compounds of formula I

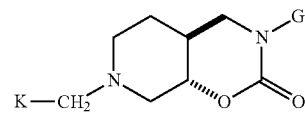

wherein G and K are as defined in the description; and salts of such compounds.

15 Claims, No Drawings

(56) References Cited

OTHER PUBLICATIONS

Greene, T. W. et al., "Protection for the Amino Group," in Protecting Groups in Organic Synthesis (3rd Edition,1999), pp. 749-779.
Larock, R.C., Comprehensive Organic Transformations, A Guide to Functional Group Preparations (2nd Edition, 1999), pp. 1234-1236.
Larock, R.C., Comprehensive Organic Transformations, A Guide to Functional Group Preparations (2nd Edition, 1999), pp. 1075-1110.
Clinical & Lab. Standards Institute, "Methods for Dilution Antimicrobial Susceptibility Tests for Bacteria that Grow Aerobically" (2006), vol. 26, No. 2.
Gibson, Mark, Pharmaceutical Preformulation and Formulation: A Practical Guide from Candidate Drug Selection to Commercial Dosage Form (1st Edition, 2001) (7 pages, TOC).
Gennaro, Alfonso, Remington: The Science and Practice of Pharmacy (20th Edition, 2005) (3 pages, TOC).
Gennaro, Alfonso, Remington: The Science and Practice of Pharmacy (21st Edition, 2005) (5 pages, TOC).
Sato et al., "One-pot reductive amination of aldehydes and ketones with -picoline-borane in methanol, in water, and in neat conditions", Tetrahedron (2004), vol. 60, pp. 7899-7906.
Smissmann E.E. et al., "A Novel Synthesis of 1,4-Benzoxathians," J. Org. Chem. (1968), vol. 33, No. 1, pp. 456-457.

\* cited by examiner

3,7-DISUBSTITUTED OCTAHYDRO-2H-PYRIDO[4,3-E][1,3]OXAZIN-2-ONE ANTIBIOTICS

CROSS-REFERENCE TO RELATED APPLICATIONS

This application is the U.S. National Phase of International Patent Application No. PCT/IB2012/056829, filed Nov. 29, 2012, which claims priority to International Patent Application No. PCT/IB2011/055383, filed Nov. 30, 2011, the contents of each are hereby incorporated by reference in their entireties.

The present invention relates to 3,7-disubstituted octahydro-2H-pyrido[4,3-e][1,3]oxazin-2-one antibiotic derivatives, pharmaceutical antibacterial compositions containing them and the use of these compounds in the manufacture of a medicament for the treatment of infections (e.g. bacterial infections). These compounds are useful antimicrobial agents effective against a variety of human and veterinary pathogens including among others Gram positive and Gram negative aerobic and anaerobic bacteria and mycobacteria.

The intensive use of antibiotics has exerted a selective evolutionary pressure on micro-organisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus*, *Streptococcus pneumoniae*, *Enterococcus* spp., and *Pseudomonas aeruginosa*, major sources of infections, are becoming multi-drug resistant and therefore difficult if not impossible to treat:

- *S. aureus* is resistant to β-lactams, quinolones and now even to vancomycin;
- *S. pneumoniae* is becoming resistant to penicillin or quinolone antibiotics and even to new macrolides;
- *Enteroccocci* are quinolone and vancomycin resistant and β-lactam antibiotics are inefficacious against these strains;
- Enterobacteriacea are cephalosporin and quinolone resistant;
- *P. aeruginosa* are β-lactam and quinolone resistant.

Further new emerging organisms like *Acinetobacter* spp. or *Clostridium difficile*, which have been selected during therapy with the currently used antibiotics, are becoming a real problem in hospital settings. In addition, microorganisms that are causing persistent infections are increasingly being recognized as causative agents or cofactors of severe chronic diseases like peptic ulcers or heart diseases.

The present invention describes for the first time trans-3,7-disubstituted octahydro-2H-pyrido[4,3-e][1,3]oxazin-2-one derivatives having antibiotic activity.

Various embodiments of the invention are presented hereafter:

1) The invention relates to the compounds of formula I wherein the relative configuration of the octahydro-pyrido[4,3-e][1,3]oxazinone moiety is trans

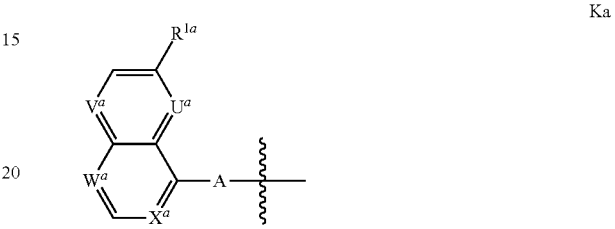

wherein

K represents the group Ka

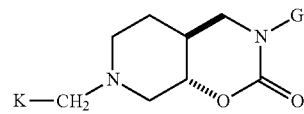

wherein $R^{1a}$ represents alkoxy, halogen or cyano (especially alkoxy);

one or two (especially two) of $U^a$, $V^a$, $W^a$ represent(s) N and the remaining each represent CH;

$X^a$ represents $CR^a$ wherein $R^a$ represents hydrogen or halogen (especially fluorine);

A represents $CHR^b$ wherein $R^b$ represents hydrogen or hydroxyl;

or K represents the group Kb

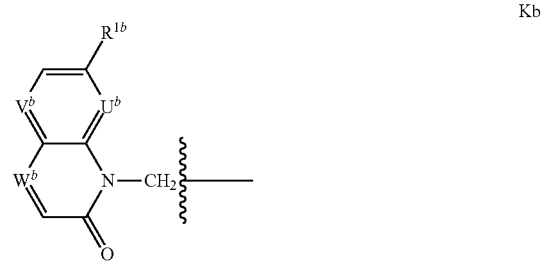

wherein $R^{1b}$ represents hydrogen, alkoxy, halogen or cyano (especially alkoxy);

one or two of $U^b$, $V^b$, and $W^b$ (especially of $U^b$ or $W^b$) represent(s) N and the remaining each represent CH;

or K represents the group Kc or Kd wherein

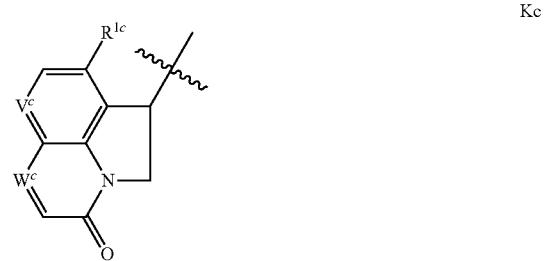

-continued

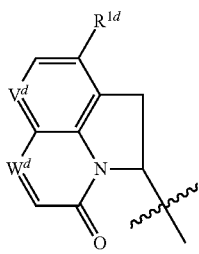

wherein $R^{1c}$ and $R^{1d}$ independently represent H or F;
$V^c$, $V^d$, $W^c$ and $W^d$ independently represent CH or N; and
G represents one of the groups Ga, Gb, Gc and Gd

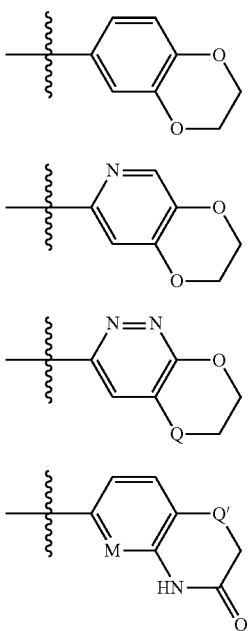

wherein M represents CH or N; and Q and Q' independently represent O or S.

The relative configuration of the octahydro-pyrido[4,3-e][1,3]oxazinone moiety is trans; i.e. the compounds of formula I are either compounds of formula $I_{E1}$, or compounds of formula $I_{E2}$, or any mixture thereof (such as racemates):

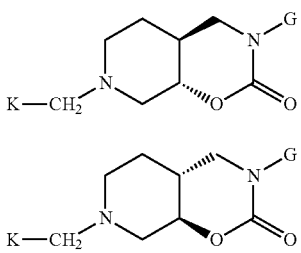

The relative configuration of stereoisomers is denoted as follows: for example, (4aR*,8aR*)-3-(2,3-dihydro-benzo[1,4]dioxin-6-yl)-7-[2-(3-methoxy-6-oxo-6H-pyrido[2,3-b]pyrazin-5-yl)-ethyl]-octahydro-pyrido[4,3-e][1,3]oxazin-2-one, if not explicitly mentioned as racemate, denominates (4aR,8aR)-3-(2,3-dihydro-benzo[1,4]dioxin-6-yl)-7-[2-(3-methoxy-6-oxo-6H-pyrido[2,3-b]pyrazin-5-yl)-ethyl]-octahydro-pyrido[4,3-e][1,3]oxazin-2-one or (4aS,8aS)-3-(2,3-dihydro-benzo[1,4]dioxin-6-yl)-7-[2-(3-methoxy-6-oxo-6H-pyrido[2,3-b]pyrazin-5-yl)-ethyl]-octahydro-pyrido[4,3-e][1,3]oxazin-2-one, or any mixture of these two enantiomers (including the racemic mixture).

The compounds of formula I may contain further stereogenic or asymmetric centers, such as one or more asymmetric carbon atoms. The compounds of formula I may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and other expressions used in this text and are intended to apply uniformly throughout the specification and claims, unless an otherwise expressly set out definition provides a broader or narrower definition.

The term "alkyl", used alone or in combination, refers to a saturated straight or branched chain alkyl group containing from one to four carbon atoms. Representative examples of alkyl groups include methyl, ethyl, propyl, iso-propyl, n-butyl, iso-butyl, sec-butyl and tert-butyl. The term "($C_x$-$C_y$)alkyl" (x and y each being an integer) refers to an alkyl group as defined before containing x to y carbon atoms.

The term "alkoxy", used alone or in combination, refers to a straight or branched chain alkoxy group containing from one to four carbon atoms. The term "($C_x$-$C_y$)alkoxy" (x and y each being an integer) refers to an alkoxy group as defined before containing x to y carbon atoms. For example, a ($C_1$-$C_3$)alkoxy group contains from one to three carbon atoms. Representative examples of alkoxy groups include methoxy, ethoxy, n-propoxy and iso-propoxy. Preferred are methoxy and ethoxy.

The term "halogen" refers to fluorine, chlorine, bromine or iodine, preferably to fluorine or chlorine.

The term "hydroxy" or "hydroxyl" refers to a —OH group.

In this text, a bond interrupted by a wavy line shows a point of attachment of the radical drawn to the rest of the molecule. For example, the radical drawn below

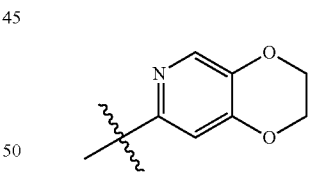

is the 2,3-dihydro-[1,4]dioxino[2,3-c]pyridin-7-yl group.

The term "enriched", for example when used in the context of enantiomers, is understood in the context of the present invention to mean especially that the respective enantiomer is present in a ratio (mutatis mutandis:purity) of at least 70:30, and notably of at least 90:10 (mutatis mutandis:purity of 70%/90%) with respect to the respective other enantiomer. Preferably the term refers to the respective essentially pure enantiomer. The term "essentially", for example when used in a term such as "essentially pure" is understood in the context of the present invention to mean especially that the respective stereoisomer/composition/compound etc. consists in an amount of at least 90, especially of at least 95, and notably of at least 99 percent by weight of the respective pure stereoisomer/composition/compound etc.

Where the plural form is used for compounds, salts, pharmaceutical compositions, diseases or the like, this is intended to mean also a single compound, salt, disease or the like.

The present invention also relates to pharmacologically acceptable salts and to compositions and formulations of compounds of formula I.

Any reference to a compound of formula I in this text (and notably in the embodiments presented above) is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

2) A second embodiment relates to the compounds of formula I according to embodiment 1) which are also compounds of formula $I_{E1}$:

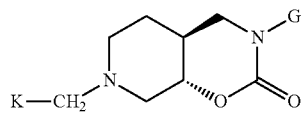

$I_{E1}$ wherein the absolute configuration of the octahydro-pyrido[4,3-e][1,3]oxazinone moiety is as depicted in formula $I_{E1}$ [i.e. the absolute configuration of the octahydro-pyrido[4,3-e][1,3]oxazinone moiety is (4aS,8aS)].

3) A third embodiment relates to the compounds of formula I according to embodiment 1) which are also compounds of formula $I_{E2}$:

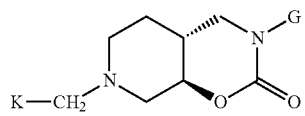

$I_{E2}$ wherein the absolute configuration of the octahydro-pyrido[4,3-e][1,3]oxazinone moiety is as depicted in formula $I_{E2}$ [i.e. the absolute configuration of the octahydro-pyrido[4,3-e][1,3]oxazinone moiety is (4aR,8aR)].

4) A further embodiment relates to the compounds according to any one of embodiments 1) to 3) wherein K represents the group Ka or Kb.

5) In particular, the compounds of formula I according to embodiment 4) will be such that K represents the group Ka wherein $R^{1a}$ represents methoxy, or such that K represents the group Kb wherein $R^{1b}$ represents methoxy.

6) A further embodiment relates to the compounds according to any one of embodiments 1) to 5) wherein K represents the group Ka.

7) A further embodiment relates to the compounds according to any one of embodiments 1) to 4) and 6) wherein, in case K represents Ka, at least one of the following characteristics (in any combination) is present:

$R^{1a}$ represents alkoxy (especially methoxy);

$U^a$ represents N, or $U^a$ and $V^a$ both represent N, or, especially, $U^a$ and $W^a$ both represent N; and the remaining of $V^a$ and $W^a$ each represent CH;

$X^a$ represents $CR^a$ wherein $R^a$ represents hydrogen or fluorine (especially $R^a$ represents fluorine);

A represents $CHR^b$ wherein $R^b$ represents hydrogen or hydroxyl (especially $R^b$ represents hydrogen).

8) A further embodiment relates to the compounds according to any one of embodiments 1) to 7) wherein, in case K represents the group Ka, A represents $CHR^b$ and $R^b$ represents hydroxyl, the absolute configuration of the carbon atom to which $R^b$ is attached to being (R).

9) A further embodiment relates to the compounds according to any one of embodiments 1) to 6) wherein K represents the group Ka and A represents $CHR^b$ wherein $R^b$ represents hydrogen.

10) A further embodiment relates to the compounds according to any one of embodiments 1) to 6) wherein K represents the group Ka, A represents $CHR^b$ wherein $R^b$ represents hydroxyl, and the absolute configuration of the carbon atom to which $R^b$ is attached to is (R).

11) A further embodiment relates to the compounds according to any one of embodiments 1) to 6) wherein K represents the group Ka wherein $R^{1a}$ represents methoxy, $U^a$ and $W^a$ each represent N and $V^a$ and $X^a$ each represent CH, $X^a$ represents $CR^a$ wherein $R^a$ represents fluorine and A represents $CHR^b$ wherein $R^b$ represents hydrogen or hydroxyl.

12) A further embodiment relates to the compounds according to any one of embodiments 1) to 5) wherein K represents the group Kb.

13) A further embodiment relates to the compounds according to embodiment 12) wherein $R^{1b}$ represents methoxy, $U^b$ represents N, $V^b$ represents CH and $W^b$ represents CH or N.

14) A further embodiment relates to the compounds according to any one of embodiments 1) to 4) and 12) wherein, in case K represents Kb, at least one of the following characteristics (in any combination) is present:

$R^{1b}$ represents hydrogen or alkoxy (notably alkoxy, especially methoxy);

$U^b$ represents N, or $U^b$ and $W^b$ both represent N, or $U^b$ and $V^b$ both represent N; and the remaining of $V^b$ and $W^b$ each represent CH.

15) A further embodiment relates to the compounds according to any one of embodiments 1) to 3) wherein K represents the group Kc or Kd.

16) A further embodiment relates to the compounds according to any one of embodiments 1) to 3) and 15) wherein, in case K represents Kc or Kd, at least one of the following characteristics (in any combination) is present:

$R^{1c}$, or respectively, $R^{1d}$ represents F;

$V^c$ and $W^c$ both represent CH, $V^c$ represents N and $W^c$ represents CH, or $W^c$ represents N and $V^c$ represents CH, or $V^c$ and $W^c$ both represent N (in a sub-embodiment: $V^c$ and $W^c$ both represent CH, or $V^c$ represents N and $W^c$ represents CH); or respectively
$V^d$ and $W^d$ both represent CH, $V^d$ represents N and $W^d$ represents CH, or $W^d$ represents N and $V^d$ represents CH, or $V^d$ and $W^d$ both represent N (in a sub-embodiment: $V^d$ and $W^d$ both represent CH, or $V^d$ represents N and $W^d$ represents CH).

17) A further embodiment relates to the compounds according to any one of embodiments 1) to 16) wherein G represents one of the groups Ga, Gb, Gc and Gd

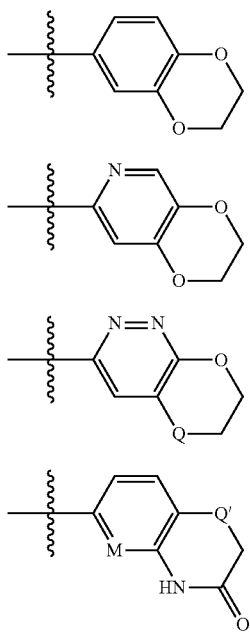

Ga

Gb

Gc

Gd wherein M represents CH and Q' represent O or S, or M represents N and Q' represents S, and Q represents O or S.

18) A further embodiment relates to the compounds according to any one of embodiments 1) to 17) wherein G represents Gd, wherein M represents CH and Q' represent O or S, or M represents N and Q' represents S.

19) A further embodiment relates to compounds according to any one of embodiments 1) to 17) wherein G represents Ga, Gb or Gc, wherein Q represents O or S.

20) A further embodiment relates to compounds of formula I according to one of embodiments 1) to 3), wherein:
K represents the group Ka

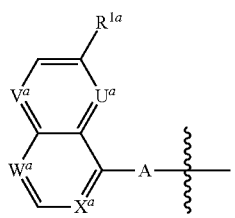

Ka wherein $R^{1a}$ represents methoxy;
$U^a$ and $W^a$ each represent N and $V^a$ and $X^a$ each represent CH;

$X^a$ represents $CR^a$ wherein $R^a$ represents fluorine;
A represents $CHR^b$ wherein $R^b$ represents hydrogen or hydroxyl;
or K represents the group Kb

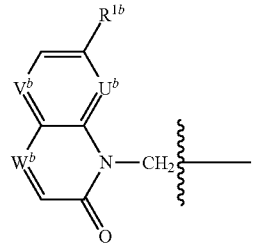

Kb wherein $R^{1b}$ represents methoxy;
$U^b$ represents N, $V^b$ represents CH and $W^b$ represents CH or N; and
G represents one of the groups Gb and Gc

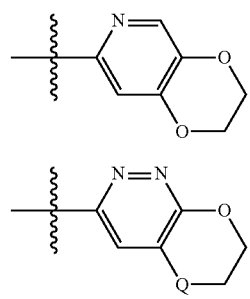

Gb

Gc wherein Q represents O or S.

21) According to one variant of embodiment 20), the compounds of formula I according to embodiment 20) will be such that K represents the group Ka, wherein Ka and $R^{1a}$, $U^a$, $V^a$, $W^a$, $X^a$ and A are as defined in embodiment 20).

22) According to another variant of embodiment 20), the compounds of formula I according to embodiment 20) will be such that K represents the group Kb, wherein Kb and $R^{1b}$, $U^b$, $V^a$ and $W^b$ are as defined in embodiment 20).

23) According to a particular embodiment, the compounds of formula I according to one of embodiments 20) to 22) will be such that G represents the group Gb, wherein Gb is as defined in embodiment 20).

24) According to another particular embodiment, the compounds of formula I according to one of embodiments 20) to 22) will be such that G represents the group Gc, wherein Gc and Q are as defined in embodiment 20).

25) A further embodiment of the present invention relates to the compounds of formula I according to embodiment 1), which are selected from the group consisting of:
(4aR,8aR)-3-(2,3-dihydro-benzo[1,4]dioxin-6-yl)-7-[2-(3-fluoro-6-methoxy-[1,5]naphthyridin-4-yl)-ethyl]-octahydro-pyrido[4,3-e][1,3]oxazin-2-one;
(4aS,8aS)-3-(2,3-dihydro-benzo[1,4]dioxin-6-yl)-7-[2-(3-fluoro-6-methoxy-[1,5]naphthyridin-4-yl)-ethyl]-octahydro-pyrido[4,3-e][1,3]oxazin-2-one;
(4aR*,8aR*)-3-(2,3-dihydro-benzo[1,4]dioxin-6-yl)-7-[2-hydroxy-2-(6-methoxy-[1,5]naphthyridin-4-yl)-ethyl]-octahydro-pyrido[4,3-e][1,3]oxazin-2-one;

(4aR*,8aR*)-3-(2,3-dihydro-benzo[1,4]dioxin-6-yl)-7-[2-(6-methoxy-[1,5]naphthyridin-4-yl)-ethyl]-octahydro-pyrido[4,3-e][1,3]oxazin-2-one;

(4aR*,8aR*)-7-[2-(3-fluoro-6-methoxy-[1,5]naphthyridin-4-yl)-ethyl]-3-(3-oxo-3,4-dihydro-2H-benzo[1,4]oxazin-6-yl)-octahydro-pyrido[4,3-e][1,3]oxazin-2-one;

(4aR*,8aR*)-3-(2,3-dihydro-benzo[1,4]dioxin-6-yl)-7-[2-(3-fluoro-6-methoxy-[1,5]naphthyridin-4-yl)-2-hydroxy-ethyl]-octahydro-pyrido[4,3-e][1,3]oxazin-2-one;

(4aR*,8aR*)-7-[2-(3-fluoro-6-methoxy-[1,5]naphthyridin-4-yl)-ethyl]-3-(3-oxo-3,4-dihydro-2H-benzo[1,4]thiazin-6-yl)-octahydro-pyrido[4,3-e][1,3]oxazin-2-one;

(4aR*,8aR*)-3-(2,3-dihydro-benzo[1,4]dioxin-6-yl)-7-[2-(7-methoxy-2-oxo-2H-quinolin-1-yl)-ethyl]-octahydro-pyrido[4,3-e][1,3]oxazin-2-one;

(4aR*,8aR*)-3-(2,3-dihydro-benzo[1,4]dioxin-6-yl)-7-[2-(7-methoxy-2-oxo-2H-quinoxalin-1-yl)-ethyl]-octahydro-pyrido[4,3-e][1,3]oxazin-2-one;

(4aR*,8aR*)-3-(2,3-dihydro-benzo[1,4]dioxin-6-yl)-7-[2-(7-methoxy-2-oxo-2H-[1,8]naphthyridin-1-yl)-ethyl]-octahydro-pyrido[4,3-e][1,3]oxazin-2-one;

(4aR*,8aR*)-3-(2,3-dihydro-benzo[1,4]dioxin-6-yl)-7-[2-(6-methoxy-3-oxo-3H-pyrido[2,3-b]pyrazin-4-yl)-ethyl]-octahydro-pyrido[4,3-e][1,3]oxazin-2-one;

(4aR*,8aR*)-3-(2,3-dihydro-benzo[1,4]dioxin-6-yl)-7-[2-(3-methoxy-6-oxo-6H-pyrido[2,3-b]pyrazin-5-yl)-ethyl]-octahydro-pyrido[4,3-e][1,3]oxazin-2-one;

(4aR*,8aR*)-3-(2,3-dihydro-benzo[1,4]dioxin-6-yl)-7-[(R)-2-(3-fluoro-6-methoxy-[1,5]naphthyridin-4-yl)-2-hydroxy-ethyl]-octahydro-pyrido[4,3-e][1,3]oxazin-2-one;

(4aS,8aS)-3-(2,3-dihydro-benzo[1,4]dioxin-6-yl)-7-[(S)-2-(3-fluoro-6-methoxy-[1,5]naphthyridin-4-yl)-2-hydroxy-ethyl]-octahydro-pyrido[4,3-e][1,3]oxazin-2-one;

(4aR,8aR)-3-(2,3-dihydro-benzo[1,4]dioxin-6-yl)-7-[(S)-2-(3-fluoro-6-methoxy-[1,5]naphthyridin-4-yl)-2-hydroxy-ethyl]-octahydro-pyrido[4,3-e][1,3]oxazin-2-one;

(4aR*,8aR*)-3-(2,3-dihydro-benzo[1,4]dioxin-6-yl)-7-[2-(7-fluoro-2-methoxy-quinolin-8-yl)-2-hydroxy-ethyl]-octahydro-pyrido[4,3-e][1,3]oxazin-2-one;

(4aR*,8aR*)-3-(2,3-dihydro-benzo[1,4]dioxin-6-yl)-7-[2-(6-fluoro-3-methoxy-quinoxalin-5-yl)-2-hydroxy-ethyl]-octahydro-pyrido[4,3-e][1,3]oxazin-2-one;

(4aR*,8aR*)-3-(2,3-dihydro-benzo[1,4]dioxin-6-yl)-7-[2-hydroxy-2-(3-methoxy-quinoxalin-5-yl)-ethyl]-octahydro-pyrido[4,3-e][1,3]oxazin-2-one;

(4aR*,8aR*)-7-[2-(3-fluoro-6-methoxy-[1,5]naphthyridin-4-yl)-ethyl]-3-(3-oxo-3,4-dihydro-2H-pyrido[3,2-b][1,4]oxazin-6-yl)-octahydro-pyrido[4,3-e][1,3]oxazin-2-one;

(4aR,8aR)-7-[2-(3-fluoro-6-methoxy-[1,5]naphthyridin-4-yl)-ethyl]-3-(3-oxo-3,4-dihydro-2H-pyrido[3,2-b][1,4]thiazin-6-yl)-octahydro-pyrido[4,3-e][1,3]oxazin-2-one;

(4aS,8aS)-7-[2-(3-fluoro-6-methoxy-[1,5]naphthyridin-4-yl)-ethyl]-3-(3-oxo-3,4-dihydro-2H-pyrido[3,2-b][1,4]thiazin-6-yl)-octahydro-pyrido[4,3-e][1,3]oxazin-2-one;

(4aR*,8aR*)-3-(2,3-dihydro-[1,4]dioxino[2,3-b]pyridin-7-yl)-7-[2-(3-fluoro-6-methoxy-[1,5]naphthyridin-4-yl)-ethyl]-octahydro-pyrido[4,3-e][1,3]oxazin-2-one;

(4aR*,8aR*)-3-(6,7-dihydro-[1,4]dioxino[2,3-c]pyridazin-3-yl)-7-[2-(3-fluoro-6-methoxy-[1,5]naphthyridin-4-yl)-ethyl]-octahydro-pyrido[4,3-e][1,3]oxazin-2-one;

(4aR*,8aR*)-3-(2,3-dihydro-[1,4]dioxino[2,3-c]pyridin-7-yl)-7-[2-(3-fluoro-6-methoxy-[1,5]naphthyridin-4-yl)-ethyl]-octahydro-pyrido[4,3-e][1,3]oxazin-2-one;

(4aR*,8aR*)-7-[2-(7-methoxy-2-oxo-2H-[1,8]naphthyridin-1-yl)-ethyl]-3-(3-oxo-3,4-dihydro-2H-pyrido[3,2-b][1,4]oxazin-6-yl)-octahydro-pyrido[4,3-e][1,3]oxazin-2-one;

(4aR*,8aR*)-7-[2-(7-methoxy-2-oxo-2H-[1,8]naphthyridin-1-yl)-ethyl]-3-(3-oxo-3,4-dihydro-2H-pyrido[3,2-b][1,4]thiazin-6-yl)-octahydro-pyrido[4,3-e][1,3]oxazin-2-one;

(4aR*,8aR*)-3-(6,7-dihydro-8-oxa-5-thia-1,2-diaza-naphthalen-3-yl)-7-[2-(3-fluoro-6-methoxy-[1,5]naphthyridin-4-yl)-ethyl]-octahydro-pyrido[4,3-e][1,3]oxazin-2-one;

(4aR*,8aR*)-3-(6,7-dihydro-8-oxa-5-thia-1,2-diaza-naphthalen-3-yl)-7-[2-(6-methoxy-3-oxo-3H-pyrido[2,3-b]pyrazin-4-yl)-ethyl]-octahydro-pyrido[4,3-e][1,3]oxazin-2-one;

(R)-2-[(4aR*,8aR*)-3-(2,3-dihydro-benzo[1,4]dioxin-6-yl)-2-oxo-octahydro-pyrido[4,3-e][1,3]oxazin-7-ylmethyl]-9-fluoro-1,2-dihydro-pyrrolo[3,2,1-ij]quinolin-4-one; and 4-[(4aR*,8aR*)-3-(2,3-dihydro-benzo[1,4]dioxin-6-yl)-2-oxo-octahydro-pyrido[4,3-e][1,3]oxazin-7-ylmethyl]-3-fluoro-4,5-dihydro-pyrrolo[3,2,1-de][1,5]naphthyridin-7-one.

In a sub-embodiment of embodiment 25), the above listed compounds having the relative configuration (4aR*,8aR*) preferably are enantiomerically enriched, having either the absolute configuration (4aR,8aR), or the absolute configuration (4aS,8aS).

26) A further embodiment of the present invention relates to the compounds of formula I according to embodiment 1), which are selected from the group consisting of:

(4aR*,8aR*)-7-(2-(7-methoxy-2-oxo-1,8-naphthyridin-1(2H)-yl)ethyl)-3-(3-oxo-3,4-dihydro-2H-benzo[b][1,4]thiazin-6-yl)octahydro-2H-pyrido[4,3-e][1,3]oxazin-2-one;

(4aR*,8aR*)-7-((2RS)-2-(3-fluoro-6-methoxy-1,5-naphthyridin-4-yl)-2-hydroxyethyl)-3-(3-oxo-3,4-dihydro-2H-benzo[b][1,4]oxazin-6-yl)octahydro-2H-pyrido[4,3-e][1,3]oxazin-2-one;

(4aR*,8aR*)-7-(((R)-9-fluoro-4-oxo-2,4-dihydro-1H-pyrrolo[3,2,1-ij]quinolin-2-yl)methyl)-3-(3-oxo-3,4-dihydro-2H-pyrido[3,2-b][1,4]oxazin-6-yl)octahydro-2H-pyrido[4,3-e][1,3]oxazin-2-one; and (4aR*,8aR*)-7-(2-(7-methoxy-2-oxo-1,8-naphthyridin-1(2H)-yl)ethyl)-3-(3-oxo-3,4-dihydro-2H-benzo[b][1,4]oxazin-6-yl)octahydro-2H-pyrido[4,3-e][1,3]oxazin-2-one.

In a sub-embodiment of embodiment 26), the above listed compounds having the relative configuration (4aR*,8aR*) preferably are enantiomerically enriched, having either the absolute configuration (4aR,8aR), or the absolute configuration (4aS,8aS).

27) The invention furthermore relates to the groups of compounds of formula I selected from the group consisting of the compounds listed in embodiments 25) and 26), which groups of compounds furthermore correspond to one of embodiments 2) to 24), as well as to the salts (in particular the pharmaceutically acceptable salts) of such compounds.

28) The invention moreover relates to any individual compound of formula I selected from the group consisting of the compounds listed in embodiments 25) and 26), and to the salts (in particular the pharmaceutically acceptable salts) of such individual compound.

The present invention also includes isotope labelled, especially $^2$H (deuterium) labelled compounds of formula I as defined in any one of embodiments 1) to 28), which compounds are identical to the compounds of formula I except that one or more atoms have each been replaced by an atom having the same atomic number but an atomic mass different from the atomic mass usually found in nature. Isotope labelled, especially $^2$H (deuterium) labelled compounds of formula I and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula I are not isotope labelled, or they are labelled only with one or more deuterium atoms. In a sub-embodiment, the compounds of formula I are not isotope labelled at all. Isotope labelled compounds of formula I may be prepared in analogy to the methods described hereinafter, but using the appropriate isotope variation of suitable reagents or starting materials.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of formula I and their pharmaceutically acceptable salts can be used as medicaments, e.g. in the form of pharmaceutical compositions for enteral (such especially oral) or parenteral administration (including topical application or inhalation).

A further aspect of the invention are pharmaceutical compositions comprising a compound of formula I, or a pharmaceutically acceptable salt thereof, and a pharmaceutically acceptable excipient/carrier material.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy*, 20th Edition, Philadelphia College of Pharmacy and Science) by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of formula I according to this invention, or the pharmaceutically acceptable salts thereof, may be used for the preparation of a medicament, and are suitable, for the prevention or treatment of a bacterial infection.

Another aspect of the invention concerns a method for the prevention or the treatment of a bacterial infection in a patient comprising the administration to said patient of a pharmaceutically active amount of a compound of formula I or a pharmaceutically acceptable salt thereof.

As well as in humans, bacterial infections can also be treated using compounds of formula I (or pharmaceutically acceptable salts thereof) in other species like pigs, ruminants, horses, dogs, cats and poultry.

Moreover, the compounds of formula I may also be used for cleaning purposes, e.g. to remove pathogenic microbes and bacteria from surgical instruments or to make a room or an area aseptic. For such purposes, the compounds of formula I could be contained in a solution or in a spray formulation.

Moreover, the compounds of formula I according to the invention are suitable for the use as substances for preserving inorganic and organic materials in particular all types of organic materials for example polymers, lubricants, paints, fibres, leather, paper and wood.

The compounds of formula I according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus,* or *Peptostreptococcus* spp.; pharyngitis, rheumatic fever, and glomerulonephritis related to infection by *Streptococcus pyogenes,* Groups C and G streptococci, *Corynebacterium diphtheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neiseria gonorrhoeae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii,* or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Borde-*

*tella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

The compounds of formula I according to any one of embodiments 1) to 28) are further useful for the preparation of a medicament for the treatment of infections that are mediated by Gram negative bacteria, such as *E. coli, Klebsiella pneumoniae* and other Enterobacteriaceae, *Acinetobacter* spp. including *Acinetobacter baumannii, Pseudomonas aeruginosa, Stenotrophomonas maltophilia, Neisseria meningitidis*, and *Bacteroides* spp.

The compounds of formula I according to any one of embodiments 1) to 28) are further useful for the preparation of a medicament for the treatment of infections that are mediated by Gram positive bacteria such as *Bacillus cereus, Bacillus anthracis, Clostridium difficile, Corynebacterium* spp. and *Propionibacterium acnes*.

The compounds of formula I according to any one of embodiments 1) to 28) are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

Besides, any preferences indicated for the compounds of formula I (whether for the compounds themselves, salts thereof, compositions containing the compounds or salts thereof, uses of the compounds or salts thereof, etc.) apply mutatis mutandis to compounds of formula $I_{E1}$ and $I_{E2}$.

This invention, thus, relates to the compounds of formula I as defined in embodiment 1), or further limited under consideration of their respective dependencies by the characteristics of any one of embodiments 2) to 28), and to pharmaceutically acceptable salts thereof. It relates furthermore to the use of such compounds as medicaments, especially for the prevention or treatment of bacterial infections (i.e. infections that are mediated by Gram negative bacteria or infections that are mediated by Gram positive bacteria), in particular for the prevention or treatment of bacterial infections caused by *Staphylococcus aureus* bacteria, and notably caused by quinolone-resistant *Staphylococcus aureus* bacteria. In particular, the following embodiments relating to the compounds of formula I according to embodiment 1) are thus possible and intended and herewith specifically disclosed in individualised form: 1, 2+1, 3+1, 4+1, 4+2+1, 4+3+1, 5+4+1, 5+4+2+1, 5+4+3+1, 6+1, 6+2+1, 6+3+1, 6+4+1, 6+4+2+1, 6+4+3+1, 6+5+4+1, 6+5+4+2+1, 6+5+4+3+1, 7+1, 7+2+1, 7+3+1, 7+4+1, 7+4+2+1, 7+4+3+1, 7+6+1, 7+6+2+1, 7+6+3+1, 7+6+4+1, 7+6+4+2+1, 7+6+4+3+1, 7+6+5+4+1, 7+6+5+4+2+1, 7+6+5+4+3+1, 8+1, 8+2+1, 8+3+1, 8+4+1, 8+4+2+1, 8+4+3+1, 8+5+4+1, 8+5+4+2+1, 8+5+4+3+1, 8+6+1, 8+6+2+1, 8+6+3+1, 8+6+4+1, 8+6+4+2+1, 8+6+4+3+1, 8+6+5+4+1, 8+6+5+4+2+1, 8+6+5+4+3+1, 8+7+1, 8+7+2+1, 8+7+3+1, 8+7+4+1, 8+7+4+2+1, 8+7+4+3+1, 8+7+6+1, 8+7+6+2+1, 8+7+6+3+1, 8+7+6+4+1, 8+7+6+4+2+1, 8+7+6+4+3+1, 8+7+6+5+4+1, 8+7+6+5+4+2+1, 8+7+6+5+4+3+1, 9+1, 9+2+1, 9+3+1, 9+4+1, 9+4+2+1, 9+4+3+1, 9+5+4+1, 9+5+4+2+1, 9+5+4+3+1, 9+6+1, 9+6+2+1, 9+6+3+1, 9+6+4+1, 9+6+4+2+1, 9+6+4+3+1, 9+6+5+4+1, 9+6+5+4+2+1, 9+6+5+4+3+1, 10+1, 10+2+1, 10+3+1, 10+4+1, 10+4+2+1, 10+4+3+1, 10+5+4+1, 10+5+4+2+1, 10+5+4+3+1, 10+6+1, 10+6+2+1, 10+6+3+1, 10+6+4+1, 10+6+4+2+1, 10+6+4+3+1, 10+6+5+4+1, 10+6+5+4+2+1, 10+6+5+4+3+1, 11+1, 11+2+1, 11+3+1, 11+4+1, 11+4+2+1, 11+4+3+1, 11+5+4+1, 11+5+4+2+1, 11+5+4+3+1, 11+6+1, 11+6+2+1, 11+6+3+1, 11+6+4+1, 11+6+4+2+1, 11+6+4+3+1, 11+6+5+4+1, 11+6+5+4+2+1, 11+6+5+4+3+1, 12+1, 12+2+1, 12+3+1, 12+4+1, 12+4+2+1, 12+4+3+1, 12+5+4+1, 12+5+4+2+1, 12+5+4+3+1, 13+12+1, 13+12+2+1, 13+12+3+1, 13+12+4+1, 13+12+4+2+1, 13+12+4+3+1, 13+12+5+4+1, 13+12+5+4+2+1, 13+12+5+4+3+1, 14+1, 14+2+1, 14+3+1, 14+4+1, 14+4+2+1, 14+4+3+1, 14+12+1, 14+12+2+1, 14+12+3+1, 14+12+4+1, 14+12+4+2+1, 14+12+4+3+1, 14+12+5+4+1, 14+12+5+4+2+1, 14+12+5+4+3+1, 15+1, 15+2+1, 15+3+1, 16+1, 16+2+1, 16+3+1, 16+15+1, 16+15+2+1, 16+15+3+1, 17+1, 17+2+1, 17+3+1, 17+4+1, 17+4+2+1, 17+4+3+1, 17+5+4+1, 17+5+4+2+1, 17+5+4+3+1, 17+6+1, 17+6+2+1, 17+6+3+1, 17+6+4+1, 17+6+4+2+1, 17+6+4+3+1, 17+6+5+4+1, 17+6+5+4+2+1, 17+6+5+4+3+1, 17+7+1, 17+7+2+1, 17+7+3+1, 17+7+4+1, 17+7+4+2+1, 17+7+4+3+1, 17+7+6+1, 17+7+6+2+1, 17+7+6+3+1, 17+7+6+4+1, 17+7+6+4+2+1, 17+7+6+4+3+1, 17+7+6+5+4+1, 17+7+6+5+4+2+1, 17+7+6+5+4+3+1, 17+8+1, 17+8+2+1, 17+8+3+1, 17+8+4+1, 17+8+4+2+1, 17+8+4+3+1, 17+8+5+4+1, 17+8+5+4+2+1, 17+8+5+4+3+1, 17+8+6+1, 17+8+6+2+1, 17+8+6+3+1, 17+8+6+4+1, 17+8+6+4+2+1, 17+8+6+4+3+1, 17+8+6+5+4+1, 17+8+6+5+4+2+1, 17+8+6+5+4+3+1, 17+8+7+1, 17+8+7+2+1, 17+8+7+3+1, 17+8+7+4+1, 17+8+7+4+2+1, 17+8+7+4+3+1, 17+8+7+6+1, 17+8+7+6+2+1, 17+8+7+6+3+1, 17+8+7+6+4+1, 17+8+7+6+4+2+1, 17+8+7+6+4+3+1, 17+8+7+6+5+4+1, 17+8+7+6+5+4+2+1, 17+8+7+6+5+4+3+1, 17+9+1, 17+9+2+1, 17+9+3+1, 17+9+4+1, 17+9+4+2+1, 17+9+4+3+1, 17+9+5+4+1, 17+9+5+4+2+1, 17+9+5+4+3+1, 17+9+6+1, 17+9+6+2+1, 17+9+6+3+1, 17+9+6+4+1, 17+9+6+4+2+1, 17+9+6+4+3+1, 17+9+6+5+4+1, 17+9+6+5+4+2+1, 17+9+6+5+4+3+1, 17+10+1, 17+10+2+1, 17+10+3+1, 17+10+4+1, 17+10+4+2+1, 17+10+4+3+1, 17+10+5+4+1, 17+10+5+4+2+1, 17+10+5+4+3+1, 17+10+6+1, 17+10+6+2+1, 17+10+6+3+1, 17+10+6+4+1, 17+10+6+4+2+1, 17+10+6+4+3+1, 17+10+6+5+4+1, 17+10+6+5+4+2+1, 17+10+6+5+4+3+1, 17+11+1, 17+11+2+1, 17+11+3+1, 17+11+4+1, 17+11+4+2+1, 17+11+4+3+1, 17+11+5+4+1, 17+11+5+4+2+1, 17+11+5+4+3+1, 17+11+6+1, 17+11+6+2+1, 17+11+6+3+1, 17+11+6+4+1, 17+11+6+4+2+1, 17+11+6+4+3+1, 17+11+6+5+4+1, 17+11+6+5+4+2+1, 17+11+6+5+4+3+1, 17+12+1, 17+12+2+1, 17+12+3+1, 17+12+4+1, 17+12+4+2+1, 17+12+4+3+1, 17+12+5+4+1, 17+12+5+4+2+1, 17+12+5+4+3+1, 17+13+12+1, 17+13+12+2+1, 17+13+12+3+1, 17+13+12+4+1, 17+13+12+4+2+1, 17+13+12+4+3+1, 17+13+12+5+4+1, 17+13+12+5+4+2+1, 17+13+12+5+4+3+1, 17+14+1, 17+14+2+1, 17+14+3+1, 17+14+4+1, 17+14+4+2+1, 17+14+4+3+1, 17+14+12+1, 17+14+12+2+1, 17+14+12+3+1, 17+14+12+4+1, 17+14+12+4+2+1, 17+14+12+4+3+1, 17+14+12+5+4+1, 17+14+12+5+4+2+1, 17+14+12+5+4+3+1, 17+15+1, 17+15+2+1, 17+15+3+1, 17+16+1, 17+16+2+1, 17+16+3+1, 17+16+15+1, 17+16+15+2+1, 17+16+15+3+1, 18+1, 18+2+1, 18+3+1, 18+4+1, 18+4+2+1, 18+4+3+1, 18+5+4+1, 18+5+4+2+1, 18+5+4+3+1, 18+6+1, 18+6+2+1, 18+6+3+1, 18+6+4+1, 18+6+4+2+1, 18+6+4+3+1, 18+6+5+4+1, 18+6+5+4+2+1, 18+6+5+4+3+1, 18+7+1, 18+7+2+1, 18+7+3+1, 18+7+4+1, 18+7+4+2+1, 18+7+4+3+1, 18+7+6+1, 18+7+6+2+1, 18+7+6+3+1, 18+7+6+4+1, 18+7+6+4+2+1, 18+7+6+4+3+1, 18+7+6+5+4+1, 18+7+6+5+4+2+1, 18+7+6+5+4+3+1, 18+8+1, 18+8+2+1, 18+8+3+1, 18+8+4+1, 18+8+4+2+1, 18+8+4+3+1, 18+8+5+4+1, 18+8+5+4+2+1, 18+8+5+4+3+1, 18+8+6+1, 18+8+6+2+1, 18+8+6+3+1, 18+8+6+4+1, 18+8+6+4+2+1, 18+8+6+4+3+1, 18+8+6+5+4+1, 18+8+6+5+4+2+1, 18+8+6+5+4+3+1, 18+8+7+1, 18+8+7+2+1, 18+8+7+3+1, 18+8+7+4+1, 18+8+7+4+2+1, 18+8+7+4+3+1, 18+8+7+6+1, 18+8+7+6+2+1, 18+8+7+6+3+1, 18+8+7+6+4+1, 18+8+7+6+4+2+1, 18+8+7+6+4+3+1, 18+8+7+6+5+4+1, 18+8+7+6+5+4+2+1, 18+8+7+6+5+4+3+1, 18+9+1, 18+9+2+1, 18+9+3+1, 18+9+4+1, 18+9+4+2+1, 18+9+4+3+1, 18+9+5+4+1, 18+9+5+4+2+1, 18+9+5+4+3+1, 18+9+6+1, 18+9+6+2+1, 18+9+6+3+1, 18+9+6+4+1, 18+9+6+4+2+1, 18+9+6+4+3+1, 18+9+6+5+4+1, 18+9+6+5+4+2+1, 18+9+6+5+4+3+1, 18+10+1, 18+10+2+1, 18+10+3+1, 18+10+4+1, 18+10+4+2+1, 18+10+4+3+1, 18+10+5+4+1, 18+10+5+4+2+1, 18+10+5+4+3+1, 18+10+6+1, 18+10+6+2+1, 18+10+6+3+1, 18+10+6+4+1, 18+10+6+4+2+1, 18+10+6+4+3+1, 18+10+6+5+4+1, 18+10+6+5+4+2+1, 18+10+6+5+4+3+1, 18+11+1, 18+11+2+1, 18+11+3+1, 18+11+4+1, 18+11+4+2+1, 18+11+4+3+1, 18+11+5+4+1, 18+11+5+4+2+1, 18+11+5+4+3+1, 18+11+6+1, 18+11+6+2+1, 18+11+6+3+1, 18+11+6+4+1, 18+11+6+4+2+1, 18+11+6+4+3+1, 18+11+6+5+4+1, 18+11+6+5+4+2+1, 18+11+6+5+4+3+1, 18+12+1, 18+12+2+1, 18+12+3+1, 18+12+4+1, 18+12+4+2+1, 18+12+4+3+1, 18+12+5+4+1, 18+12+5+4+2+1, 18+12+5+4+3+1, 18+13+12+1, 18+13+12+2+1, 18+13+12+3+1, 18+13+12+4+1, 18+13+12+4+2+1, 18+13+12+4+3+1, 18+13+12+5+4+1, 18+13+12+5+4+2+1, 18+13+12+5+4+3+1, 18+14+1, 18+14+2+1, 18+14+3+1, 18+14+4+1, 18+14+4+2+1, 18+14+4+3+1, 18+14+12+1, 18+14+12+2+1, 18+14+12+3+1, 18+14+12+4+1, 18+14+12+4+2+1, 18+14+12+4+3+1, 18+14+12+5+4+1, 18+14+12+5+4+2+1, 18+14+12+5+4+3+1, 18+15+1, 18+15+2+1, 18+15+3+1, 18+16+1, 18+16+2+1, 18+16+3+1, 18+16+15+1, 18+16+15+2+1, 18+16+15+3+1, 18+17+1, 18+17+2+1, 18+17+3+1, 18+17+4+1, 18+17+4+2+1, 18+17+4+3+1, 18+17+5+4+1, 18+17+5+4+2+1, 18+17+5+4+3+1, 18+17+6+1, 18+17+6+2+1, 18+17+6+3+1, 18+17+6+4+1, 18+17+6+4+2+1, 18+17+6+4+3+1, 18+17+6+5+4+1, 18+17+6+5+4+2+1, 18+17+6+5+4+3+1, 18+17+7+1, 18+17+7+2+1, 18+17+7+3+1, 18+17+7+4+1, 18+17+7+4+2+1, 18+17+7+4+3+1, 18+17+7+6+1, 18+17+7+6+2+1, 18+17+7+6+3+1, 18+17+7+6+4+1, 18+17+7+6+4+2+1, 18+17+7+6+4+3+1, 18+17+7+6+5+4+1, 18+17+7+6+5+4+2+1, 18+17+7+6+5+4+3+1, 18+17+8+1, 18+17+8+2+1, 18+17+8+3+1, 18+17+8+4+1, 18+17+8+4+2+1, 18+17+8+4+3+1, 18+17+8+5+4+1, 18+17+8+5+4+2+1, 18+17+8+5+4+3+1, 18+17+8+6+1, 18+17+8+6+2+1, 18+17+8+6+3+1, 18+17+8+6+4+1, 18+17+8+6+4+2+1, 18+17+8+6+4+3+1, 18+17+8+6+5+4+1, 18+17+8+6+5+4+2+1, 18+17+8+6+5+4+3+1, 18+17+8+7+1, 18+17+8+7+2+1, 18+17+8+7+3+1, 18+17+8+7+4+1, 18+17+8+7+4+2+1, 18+17+8+7+4+3+1, 18+17+8+7+6+1, 18+17+8+7+6+2+1, 18+17+8+7+6+3+1, 18+17+8+7+6+4+1, 18+17+8+7+6+4+2+1, 18+17+8+7+6+4+3+1, 18+17+8+7+6+5+4+1, 18+17+8+7+6+5+4+2+1, 18+17+8+7+6+5+4+3+1, 18+17+9+1, 18+17+9+2+1, 18+17+9+3+1, 18+17+9+4+1, 18+17+9+4+2+1, 18+17+9+4+3+1, 18+17+9+5+4+1, 18+17+9+5+4+2+1, 18+17+9+5+4+3+1, 18+17+9+6+1, 18+17+9+6+2+1, 18+17+9+6+3+1, 18+17+9+6+4+1, 18+17+9+6+4+2+1, 18+17+9+6+4+3+1, 18+17+9+6+5+4+1, 18+17+9+6+5+4+2+1, 18+17+9+6+5+4+3+1, 18+17+10+1, 18+17+10+2+1, 18+17+10+3+1, 18+17+10+4+1, 18+17+10+4+2+1, 18+17+10+4+3+1, 18+17+10+5+4+1, 18+17+10+5+4+2+1, 18+17+10+5+4+3+1, 18+17+10+6+1, 18+17+10+6+2+1, 18+17+10+6+3+1, 18+17+10+6+4+1, 18+17+10+6+4+2+1, 18+17+10+6+4+3+1, 18+17+10+6+5+4+1, 18+17+10+6+5+4+2+1, 18+17+10+6+5+4+3+1, 18+17+11+1, 18+17+11+2+1, 18+17+11+3+1, 18+17+11+4+1, 18+17+11+4+2+1, 18+17+11+4+3+1, 18+17+11+5+4+1, 18+17+11+5+4+2+1, 18+17+11+5+4+3+1, 18+17+11+6+1, 18+17+11+6+2+1, 18+17+11+6+3+1, 18+17+11+6+4+1, 18+17+11+6+4+2+1, 18+17+11+6+4+3+1, 18+17+11+6+5+4+1, 18+17+11+6+5+4+2+1, 18+17+11+6+5+4+3+1, 18+17+12+1, 18+17+12+2+1, 18+17+12+3+1, 18+17+12+4+1, 18+17+12+4+2+1, 18+17+12+4+3+1, 18+17+12+5+4+1, 18+17+12+5+4+2+1, 18+17+12+5+4+3+1, 18+17+13+12+1, 18+17+13+12+2+1, 18+17+13+12+3+1, 18+17+13+12+4+1, 18+17+13+12+4+2+1, 18+17+13+12+4+3+1, 18+17+13+12+5+4+1, 18+17+13+12+5+4+2+1, 18+17+13+12+5+4+3+1, 18+17+14+1, 18+17+14+2+1, 18+17+14+3+1, 18+17+14+4+1, 18+17+14+4+2+1, 18+17+14+4+3+1, 18+17+14+12+1, 18+17+14+12+2+1, 18+17+14+12+3+1, 18+17+14+12+4+1, 18+17+14+12+4+2+1, 18+17+14+12+4+3+1, 18+17+14+12+5+4+1, 18+17+14+12+5+4+2+1, 18+17+14+12+5+4+3+1, 18+17+15+1, 18+17+15+2+1, 18+17+15+3+1, 18+17+16+1, 18+17+16+2+1, 18+17+16+3+1, 18+17+16+15+1, 18+17+16+15+2+1, 18+17+16+15+3+1, 19+1, 19+2+1, 19+3+1, 19+4+1, 19+4+2+1, 19+4+3+1, 19+5+4+1, 19+5+4+2+1, 19+5+4+3+1, 19+6+1, 19+6+2+1, 19+6+3+1, 19+6+4+1, 19+6+4+2+1, 19+6+4+3+1, 19+6+5+4+1, 19+6+5+4+2+1, 19+6+5+4+3+1, 19+7+1, 19+7+2+1, 19+7+3+1, 19+7+4+1, 19+7+4+2+1, 19+7+4+3+1, 19+7+6+1, 19+7+6+2+1, 19+7+6+3+1, 19+7+6+4+1, 19+7+6+4+2+1, 19+7+6+4+3+1, 19+7+6+5+4+1, 19+7+6+5+4+2+1, 19+7+6+5+4+3+1, 19+8+1, 19+8+2+1, 19+8+3+1, 19+8+4+1, 19+8+4+2+1, 19+8+4+3+1, 19+8+5+4+1, 19+8+5+4+2+1, 19+8+5+4+3+1, 19+8+6+1, 19+8+6+2+1, 19+8+6+3+1, 19+8+6+4+1, 19+8+6+4+2+1, 19+8+6+4+3+1, 19+8+6+5+4+1, 19+8+6+5+4+2+1, 19+8+6+5+4+3+1, 19+8+7+1, 19+8+7+2+1, 19+8+7+3+1, 19+8+7+4+1, 19+8+7+4+2+1, 19+8+7+4+3+1, 19+8+7+6+1, 19+8+7+6+2+1, 19+8+7+6+3+1, 19+8+7+6+4+1, 19+8+7+6+4+2+1, 19+8+7+6+4+3+1, 19+8+7+6+5+4+1, 19+8+7+6+5+4+2+1, 19+8+7+6+5+4+3+1, 19+9+1, 19+9+2+1, 19+9+3+1, 19+9+4+1, 19+9+4+2+1, 19+9+4+3+1, 19+9+5+4+1, 19+9+5+4+2+1, 19+9+5+4+3+1, 19+9+6+1, 19+9+6+2+1, 19+9+6+3+1, 19+9+6+4+1, 19+9+6+4+2+1, 19+9+6+4+3+1, 19+9+6+5+4+1, 19+9+6+5+4+2+1, 19+9+6+5+4+3+1, 19+10+1, 19+10+2+1, 19+10+3+1, 19+10+4+1, 19+10+4+2+1, 19+10+4+3+1, 19+10+5+4+1, 19+10+5+4+2+1, 19+10+5+4+3+1, 19+10+6+1, 19+10+6+2+1, 19+10+6+3+1, 19+10+6+4+1, 19+10+6+4+2+1, 19+10+6+4+3+1, 19+10+6+5+4+1, 19+10+6+5+4+2+1, 19+10+6+5+4+3+1, 19+11+1, 19+11+2+1, 19+11+3+1, 19+11+4+1, 19+11+4+2+1, 19+11+4+3+1, 19+11+5+4+1, 19+11+5+4+2+1, 19+11+5+4+3+1, 19+11+6+1, 19+11+6+2+1, 19+11+6+3+1, 19+11+6+4+1, 19+11+6+4+2+1, 19+11+6+4+3+1, 19+11+6+5+4+1, 19+11+6+5+4+2+1, 19+11+6+5+4+3+1, 19+12+1, 19+12+2+1, 19+12+3+1, 19+12+4+1, 19+12+4+2+1, 19+12+4+3+1, 19+12+5+4+1, 19+12+5+4+2+1, 19+12+5+4+3+1, 19+13+12+1, 19+13+12+2+1, 19+13+12+3+1, 19+13+12+4+1, 19+13+12+4+2+1, 19+13+12+4+3+1, 19+13+12+5+4+1, 19+13+12+5+4+2+1, 19+13+12+5+4+3+1, 19+14+1, 19+14+2+1, 19+14+3+1, 19+14+4+1, 19+14+4+2+1, 19+14+4+3+1, 19+14+12+1, 19+14+12+2+1, 19+14+12+3+1, 19+14+12+4+1, 19+14+12+4+2+1, 19+14+12+4+3+1, 19+14+12+5+4+1, 19+14+12+5+4+2+1, 19+14+12+5+4+3+1, 19+15+1, 19+15+2+1, 19+15+3+1, 19+16+1, 19+16+2+1, 19+16+3+1, 19+16+15+1, 19+16+15+2+1, 19+16+15+3+1, 19+17+1, 19+17+2+1, 19+17+3+1, 19+17+4+1, 19+17+4+2+1, 19+17+4+3+1, 19+17+5+4+1, 19+17+5+4+2+1, 19+17+5+4+3+1, 19+17+6+1, 19+17+6+2+1, 19+17+6+3+1, 19+17+6+4+1, 19+17+6+4+2+1, 19+17+6+4+3+1, 19+17+6+5+4+1, 19+17+6+5+4+2+1, 19+17+6+5+4+3+1, 19+17+7+1, 19+17+7+2+1, 19+17+7+3+1, 19+17+7+4+1, 19+17+7+4+2+1, 19+17+7+4+3+1, 19+17+7+6+1, 19+17+7+6+2+1, 19+17+7+6+3+1, 19+17+7+6+4+1, 19+17+7+6+4+2+1, 19+17+7+6+4+3+1, 19+17+7+6+5+4+1, 19+17+7+6+5+4+

2+1, 19+17+7+6+5+4+3+1, 19+17+8+1, 19+17+8+2+1, 19+17+8+3+1, 19+17+8+4+1, 19+17+8+4+2+1, 19+17+8+4+3+1, 19+17+8+5+1, 19+17+8+5+2+1, 19+17+8+5+4+1, 19+17+8+5+4+2+1, 19+17+8+5+4+3+1, 19+17+8+6+1, 19+17+8+6+2+1, 19+17+8+6+3+1, 19+17+8+6+4+1, 19+17+8+6+4+2+1, 19+17+8+6+4+3+1, 19+17+8+6+5+4+1, 19+17+8+6+5+4+2+1, 19+17+8+6+5+4+3+1, 19+17+8+7+1, 19+17+8+7+2+1, 19+17+8+7+3+1, 19+17+8+7+4+1, 19+17+8+7+4+2+1, 19+17+8+7+4+3+1, 19+17+8+7+6+1, 19+17+8+7+6+2+1, 19+17+8+7+6+3+1, 19+17+8+7+6+4+1, 19+17+8+7+6+4+2+1, 19+17+8+7+6+4+3+1, 19+17+8+7+6+5+4+1, 19+17+8+7+6+5+4+2+1, 19+17+8+7+6+5+4+3+1, 19+17+9+1, 19+17+9+2+1, 19+17+9+3+1, 19+17+9+4+1, 19+17+9+4+2+1, 19+17+9+4+3+1, 19+17+9+5+4+1, 19+17+9+5+4+2+1, 19+17+9+5+4+3+1, 19+17+9+6+1, 19+17+9+6+2+1, 19+17+9+6+3+1, 19+17+9+6+4+1, 19+17+9+6+4+2+1, 19+17+9+6+4+3+1, 19+17+9+6+5+4+1, 19+17+9+6+5+4+2+1, 19+17+9+6+5+4+3+1, 19+17+10+1, 19+17+10+2+1, 19+17+10+3+1, 19+17+10+4+1, 19+17+10+4+2+1, 19+17+10+4+3+1, 19+17+10+5+4+1, 19+17+10+5+4+2+1, 19+17+10+5+4+3+1, 19+17+10+6+1, 19+17+10+6+2+1, 19+17+10+6+3+1, 19+17+10+6+4+1, 19+17+10+6+4+2+1, 19+17+10+6+4+3+1, 19+17+10+6+5+4+1, 19+17+10+6+5+4+2+1, 19+17+10+6+5+4+3+1, 19+17+11+1, 19+17+11+2+1, 19+17+11+3+1, 19+17+11+4+1, 19+17+11+4+2+1, 19+17+11+4+3+1, 19+17+11+5+4+1, 19+17+11+5+4+2+1, 19+17+11+5+4+3+1, 19+17+11+6+1, 19+17+11+6+2+1, 19+17+11+6+3+1, 19+17+11+6+4+1, 19+17+11+6+4+2+1, 19+17+11+6+4+3+1, 19+17+11+6+5+4+1, 19+17+11+6+5+4+2+1, 19+17+11+6+5+4+3+1, 19+17+12+1, 19+17+12+2+1, 19+17+12+3+1, 19+17+12+4+1, 19+17+12+4+2+1, 19+17+12+4+3+1, 19+17+12+5+4+1, 19+17+12+5+4+2+1, 19+17+12+5+4+3+1, 19+17+13+12+1, 19+17+13+12+2+1, 19+17+13+12+3+1, 19+17+13+12+4+1, 19+17+13+12+4+2+1, 19+17+13+12+4+3+1, 19+17+13+12+5+4+1, 19+17+13+12+5+4+2+1, 19+17+13+12+5+4+3+1, 19+17+14+1, 19+17+14+2+1, 19+17+14+3+1, 19+17+14+4+1, 19+17+14+4+2+1, 19+17+14+4+3+1, 19+17+14+12+1, 19+17+14+12+2+1, 19+17+14+12+3+1, 19+17+14+12+4+1, 19+17+14+12+4+2+1, 19+17+14+12+4+3+1, 19+17+14+12+5+4+1, 19+17+14+12+5+4+2+1, 19+17+14+12+5+4+3+1, 19+17+15+1, 19+17+15+2+1, 19+17+15+3+1, 19+17+16+1, 19+17+16+2+1, 19+17+16+3+1, 19+17+16+15+1, 19+17+16+15+2+1, 19+17+16+15+3+1, 20+1, 20+2+1, 20+3+1, 21+20+1, 21+20+2+1, 21+20+3+1, 22+20+1, 22+20+2+1, 22+20+3+1, 23+20+1, 23+20+2+1, 23+20+3+1, 23+21+20+1, 23+21+20+2+1, 23+21+20+3+1, 23+22+20+1, 23+22+20+2+1, 23+22+20+3+1, 24+20+1, 24+20+2+1, 24+20+3+1, 24+21+20+1, 24+21+20+2+1, 24+21+20+3+1, 24+22+20+1, 24+22+20+2+1, 24+22+20+3+1, 25, 26, 27+2+1, 27+3+1, 27+4+1, 27+4+2+1, 27+4+3+1, 27+5+4+1, 27+5+4+2+1, 27+5+4+3+1, 27+6+1, 27+6+2+1, 27+6+3+1, 27+6+4+1, 27+6+4+2+1, 27+6+4+3+1, 27+6+5+4+1, 27+6+5+4+2+1, 27+6+5+4+3+1, 27+7+1, 27+7+2+1, 27+7+3+1, 27+7+4+1, 27+7+4+2+1, 27+7+4+3+1, 27+7+6+1, 27+7+6+2+1, 27+7+6+3+1, 27+7+6+4+1, 27+7+6+4+2+1, 27+7+6+4+3+1, 27+7+6+5+4+1, 27+7+6+5+4+2+1, 27+7+6+5+4+3+1, 27+8+1, 27+8+2+1, 27+8+3+1, 27+8+4+1, 27+8+4+2+1, 27+8+4+3+1, 27+8+5+4+1, 27+8+5+4+2+1, 27+8+5+4+3+1, 27+8+6+1, 27+8+6+2+1, 27+8+6+3+1, 27+8+6+4+1, 27+8+6+4+2+1, 27+8+6+4+3+1, 27+8+6+5+4+1, 27+8+6+5+4+2+1, 27+8+6+5+4+3+1, 27+8+7+1, 27+8+7+2+1, 27+8+7+3+1, 27+8+7+4+1, 27+8+7+4+2+1, 27+8+7+4+3+1, 27+8+7+6+1, 27+8+7+6+2+1, 27+8+7+6+3+1, 27+8+7+6+4+1, 27+8+7+6+4+2+1, 27+8+7+6+4+3+1, 27+8+7+6+5+4+1, 27+8+7+6+5+4+2+1, 27+8+7+6+5+4+3+1, 27+9+1, 27+9+2+1, 27+9+3+1, 27+9+4+1, 27+9+4+2+1, 27+9+4+3+1, 27+9+5+4+1, 27+9+5+4+2+1, 27+9+5+4+3+1, 27+9+6+1, 27+9+6+2+1, 27+9+6+3+1, 27+9+6+4+1, 27+9+6+4+2+1, 27+9+6+4+3+1, 27+9+6+5+4+1, 27+9+6+5+4+2+1, 27+9+6+5+4+3+1, 27+10+1, 27+10+2+1, 27+10+3+1, 27+10+4+1, 27+10+4+2+1, 27+10+4+3+1, 27+10+5+4+1, 27+10+5+4+2+1, 27+10+5+4+3+1, 27+10+6+1, 27+10+6+2+1, 27+10+6+3+1, 27+10+6+4+1, 27+10+6+4+2+1, 27+10+6+4+3+1, 27+10+6+5+4+1, 27+10+6+5+4+2+1, 27+10+6+5+4+3+1, 27+11+1, 27+11+2+1, 27+11+3+1, 27+11+4+1, 27+11+4+2+1, 27+11+4+3+1, 27+11+5+4+1, 27+11+5+4+2+1, 27+11+5+4+3+1, 27+11+6+1, 27+11+6+2+1, 27+11+6+3+1, 27+11+6+4+1, 27+11+6+4+2+1, 27+11+6+4+3+1, 27+11+6+5+4+1, 27+11+6+5+4+2+1, 27+11+6+5+4+3+1, 27+12+1, 27+12+2+1, 27+12+3+1, 27+12+4+1, 27+12+4+2+1, 27+12+4+3+1, 27+12+5+4+1, 27+12+5+4+2+1, 27+12+5+4+3+1, 27+13+12+1, 27+13+12+2+1, 27+13+12+3+1, 27+13+12+4+1, 27+13+12+4+2+1, 27+13+12+4+3+1, 27+13+12+5+4+1, 27+13+12+5+4+2+1, 27+13+12+5+4+3+1, 27+14+1, 27+14+2+1, 27+14+3+1, 27+14+4+1, 27+14+4+2+1, 27+14+4+3+1, 27+14+12+1, 27+14+12+2+1, 27+14+12+3+1, 27+14+12+4+1, 27+14+12+4+2+1, 27+14+12+4+3+1, 27+14+12+5+4+1, 27+14+12+5+4+2+1, 27+14+12+5+4+3+1, 27+15+1, 27+15+2+1, 27+15+3+1, 27+16+1, 27+16+2+1, 27+16+3+1, 27+16+15+1, 27+16+15+2+1, 27+16+15+3+1, 27+17+1, 27+17+2+1, 27+17+3+1, 27+17+4+1, 27+17+4+2+1, 27+17+4+3+1, 27+17+5+4+1, 27+17+5+4+2+1, 27+17+5+4+3+1, 27+17+6+1, 27+17+6+2+1, 27+17+6+3+1, 27+17+6+4+1, 27+17+6+4+2+1, 27+17+6+4+3+1, 27+17+6+5+4+1, 27+17+6+5+4+2+1, 27+17+6+5+4+3+1, 27+17+7+1, 27+17+7+2+1, 27+17+7+3+1, 27+17+7+4+1, 27+17+7+4+2+1, 27+17+7+4+3+1, 27+17+7+6+1, 27+17+7+6+2+1, 27+17+7+6+3+1, 27+17+7+6+4+1, 27+17+7+6+4+2+1, 27+17+7+6+4+3+1, 27+17+7+6+5+4+1, 27+17+7+6+5+4+2+1, 27+17+7+6+5+4+3+1, 27+17+8+1, 27+17+8+2+1, 27+17+8+3+1, 27+17+8+4+1, 27+17+8+4+2+1, 27+17+8+4+3+1, 27+17+8+5+4+1, 27+17+8+5+4+2+1, 27+17+8+5+4+3+1, 27+17+8+6+1, 27+17+8+6+2+1, 27+17+8+6+3+1, 27+17+8+6+4+1, 27+17+8+6+4+2+1, 27+17+8+6+4+3+1, 27+17+8+6+5+4+1, 27+17+8+6+5+4+2+1, 27+17+8+6+5+4+3+1, 27+17+8+7+1, 27+17+8+7+2+1, 27+17+8+7+3+1, 27+17+8+7+4+1, 27+17+8+7+4+2+1, 27+17+8+7+4+3+1, 27+17+8+7+6+1, 27+17+8+7+6+2+1, 27+17+8+7+6+3+1, 27+17+8+7+6+4+1, 27+17+8+7+6+4+2+1, 27+17+8+7+6+4+3+1, 27+17+8+7+6+5+4+1, 27+17+8+7+6+5+4+2+1, 27+17+8+7+6+5+4+3+1, 27+17+9+1, 27+17+9+2+1, 27+17+9+3+1, 27+17+9+4+1, 27+17+9+4+2+1, 27+17+9+4+3+1, 27+17+9+5+4+1, 27+17+9+5+4+2+1, 27+17+9+5+4+3+1, 27+17+9+6+1, 27+17+9+6+2+1, 27+17+9+6+3+1, 27+17+9+6+4+1, 27+17+9+6+4+2+1, 27+17+9+6+4+3+1, 27+17+9+6+5+4+1, 27+17+9+6+5+4+2+1, 27+17+9+6+5+4+3+1, 27+17+10+1, 27+17+10+2+1, 27+17+10+3+1, 27+17+10+4+1, 27+17+10+4+2+1, 27+17+10+4+3+1, 27+17+10+5+4+1, 27+17+10+5+4+2+1, 27+17+10+5+4+3+1, 27+17+10+6+1, 27+17+10+6+2+1, 27+17+10+6+3+1, 27+17+10+6+4+1, 27+17+10+6+4+2+1, 27+17+10+6+4+3+1, 27+17+10+6+5+4+1, 27+17+10+6+5+4+2+1, 27+17+10+6+5+4+3+1, 27+17+11+1, 27+17+11+2+1, 27+17+11+3+1, 27+17+11+4+1, 27+17+11+4+2+1, 27+17+11+4+3+1, 27+17+11+5+4+1, 27+17+11+5+4+2+1, 27+17+11+5+4+3+1, 27+17+11+6+1, 27+17+11+6+2+1, 27+17+11+6+3+1, 27+17+11+6+4+1, 27+17+11+6+4+2+1, 27+17+11+6+4+3+1, 27+17+11+6+5+4+1, 27+17+11+6+5+4+2+1, 27+17+11+6+5+4+3+1, 27+17+12+1, 27+17+12+2+1,

27+17+12+3+1, 27+17+12+4+1, 27+17+12+4+2+1, 27+17+12+4+3+1, 27+17+12+5+4+1, 27+17+12+5+4+2+1, 27+17+12+5+4+3+1, 27+17+13+12+1, 27+17+13+12+2+1, 27+17+13+12+3+1, 27+17+13+12+4+1, 27+17+13+12+4+2+1, 27+17+13+12+4+3+1, 27+17+13+12+5+4+1, 27+17+13+12+5+4+2+1, 27+17+13+12+5+4+3+1, 27+17+14+1, 27+17+14+2+1, 27+17+14+3+1, 27+17+14+4+1, 27+17+14+4+2+1, 27+17+14+4+3+1, 27+17+14+12+1, 27+17+14+12+2+1, 27+17+14+12+3+1, 27+17+14+12+4+1, 27+17+14+12+4+2+1, 27+17+14+12+4+3+1, 27+17+14+12+5+4+1, 27+17+14+12+5+4+2+1, 27+17+14+12+5+4+3+1, 27+17+15+1, 27+17+15+2+1, 27+17+15+3+1, 27+17+16+1, 27+17+16+2+1, 27+17+16+3+1, 27+17+16+15+1, 27+17+16+15+2+1, 27+17+16+15+3+1, 27+18+1, 27+18+2+1, 27+18+3+1, 27+18+4+1, 27+18+4+2+1, 27+18+4+3+1, 27+18+5+4+1, 27+18+5+4+2+1, 27+18+5+4+3+1, 27+18+6+1, 27+18+6+2+1, 27+18+6+3+1, 27+18+6+4+1, 27+18+6+4+2+1, 27+18+6+4+3+1, 27+18+6+5+4+1, 27+18+6+5+4+2+1, 27+18+6+5+4+3+1, 27+18+7+1, 27+18+7+2+1, 27+18+7+3+1, 27+18+7+4+1, 27+18+7+4+2+1, 27+18+7+4+3+1, 27+18+7+6+1, 27+18+7+6+2+1, 27+18+7+6+3+1, 27+18+7+6+4+1, 27+18+7+6+4+2+1, 27+18+7+6+4+3+1, 27+18+7+6+5+4+1, 27+18+7+6+5+4+2+1, 27+18+7+6+5+4+3+1, 27+18+8+1, 27+18+8+2+1, 27+18+8+3+1, 27+18+8+4+1, 27+18+8+4+2+1, 27+18+8+4+3+1, 27+18+8+5+4+1, 27+18+8+5+4+2+1, 27+18+8+5+4+3+1, 27+18+8+6+1, 27+18+8+6+2+1, 27+18+8+6+3+1, 27+18+8+6+4+1, 27+18+8+6+4+2+1, 27+18+8+6+4+3+1, 27+18+8+6+5+4+1, 27+18+8+6+5+4+2+1, 27+18+8+6+5+4+3+1, 27+18+8+7+1, 27+18+8+7+2+1, 27+18+8+7+3+1, 27+18+8+7+4+1, 27+18+8+7+4+2+1, 27+18+8+7+4+3+1, 27+18+8+7+6+1, 27+18+8+7+6+2+1, 27+18+8+7+6+3+1, 27+18+8+7+6+4+1, 27+18+8+7+6+4+2+1, 27+18+8+7+6+4+3+1, 27+18+8+7+6+5+4+1, 27+18+8+7+6+5+4+2+1, 27+18+8+7+6+5+4+3+1, 27+18+9+1, 27+18+9+2+1, 27+18+9+3+1, 27+18+9+4+1, 27+18+9+4+2+1, 27+18+9+4+3+1, 27+18+9+5+4+1, 27+18+9+5+4+2+1, 27+18+9+5+4+3+1, 27+18+9+6+1, 27+18+9+6+2+1, 27+18+9+6+3+1, 27+18+9+6+4+1, 27+18+9+6+4+2+1, 27+18+9+6+4+3+1, 27+18+9+6+5+4+1, 27+18+9+6+5+4+2+1, 27+18+9+6+5+4+3+1, 27+18+10+1, 27+18+10+2+1, 27+18+10+3+1, 27+18+10+4+1, 27+18+10+4+2+1, 27+18+10+4+3+1, 27+18+10+5+4+1, 27+18+10+5+4+2+1, 27+18+10+5+4+3+1, 27+18+10+6+1, 27+18+10+6+2+1, 27+18+10+6+3+1, 27+18+10+6+4+1, 27+18+10+6+4+2+1, 27+18+10+6+4+3+1, 27+18+10+6+5+4+1, 27+18+10+6+5+4+2+1, 27+18+10+6+5+4+3+1, 27+18+11+1, 27+18+11+2+1, 27+18+11+3+1, 27+18+11+4+1, 27+18+11+4+2+1, 27+18+11+4+3+1, 27+18+11+5+4+1, 27+18+11+5+4+2+1, 27+18+11+5+4+3+1, 27+18+11+6+1, 27+18+11+6+2+1, 27+18+11+6+3+1, 27+18+11+6+4+1, 27+18+11+6+4+2+1, 27+18+11+6+4+3+1, 27+18+11+6+5+4+1, 27+18+11+6+5+4+2+1, 27+18+11+6+5+4+3+1, 27+18+12+1, 27+18+12+2+1, 27+18+12+3+1, 27+18+12+4+1, 27+18+12+4+2+1, 27+18+12+4+3+1, 27+18+12+5+4+1, 27+18+12+5+4+2+1, 27+18+12+5+4+3+1, 27+18+13+12+1, 27+18+13+12+2+1, 27+18+13+12+3+1, 27+18+13+12+4+1, 27+18+13+12+4+2+1, 27+18+13+12+4+3+1, 27+18+13+12+5+4+1, 27+18+13+12+5+4+2+1, 27+18+13+12+5+4+3+1, 27+18+14+1, 27+18+14+2+1, 27+18+14+3+1, 27+18+14+4+1, 27+18+14+4+2+1, 27+18+14+4+3+1, 27+18+14+12+1, 27+18+14+12+2+1, 27+18+14+12+3+1, 27+18+14+12+4+1, 27+18+14+12+4+2+1, 27+18+14+12+4+3+1, 27+18+14+12+5+4+1, 27+18+14+12+5+4+2+1, 27+18+14+12+5+4+3+1, 27+18+15+1, 27+18+15+2+1, 27+18+15+3+1, 27+18+16+1, 27+18+16+2+1, 27+18+16+3+1, 27+18+16+15+1, 27+18+16+15+2+1, 27+18+16+15+3+1, 27+18+17+1, 27+18+17+2+1, 27+18+17+3+1, 27+18+17+4+1, 27+18+17+4+2+1, 27+18+17+4+3+1, 27+18+17+5+4+1, 27+18+17+5+4+2+1, 27+18+17+5+4+3+1, 27+18+17+6+1, 27+18+17+6+2+1, 27+18+17+6+3+1, 27+18+17+6+4+1, 27+18+17+6+4+2+1, 27+18+17+6+4+3+1, 27+18+17+6+5+4+1, 27+18+17+6+5+4+2+1, 27+18+17+6+5+4+3+1, 27+18+17+7+1, 27+18+17+7+2+1, 27+18+17+7+3+1, 27+18+17+7+4+1, 27+18+17+7+4+2+1, 27+18+17+7+4+3+1, 27+18+17+7+6+1, 27+18+17+7+6+2+1, 27+18+17+7+6+3+1, 27+18+17+7+6+4+1, 27+18+17+7+6+4+2+1, 27+18+17+7+6+4+3+1, 27+18+17+7+6+5+4+1, 27+18+17+7+6+5+4+2+1, 27+18+17+7+6+5+4+3+1, 27+18+17+8+1, 27+18+17+8+2+1, 27+18+17+8+3+1, 27+18+17+8+4+1, 27+18+17+8+4+2+1, 27+18+17+8+4+3+1, 27+18+17+8+5+4+1, 27+18+17+8+5+4+2+1, 27+18+17+8+5+4+3+1, 27+18+17+8+6+1, 27+18+17+8+6+2+1, 27+18+17+8+6+3+1, 27+18+17+8+6+4+1, 27+18+17+8+6+4+2+1, 27+18+17+8+6+4+3+1, 27+18+17+8+6+5+4+1, 27+18+17+8+6+5+4+2+1, 27+18+17+8+6+5+4+3+1, 27+18+17+8+7+1, 27+18+17+8+7+2+1, 27+18+17+8+7+3+1, 27+18+17+8+7+4+1, 27+18+17+8+7+4+2+1, 27+18+17+8+7+4+3+1, 27+18+17+8+7+6+1, 27+18+17+8+7+6+2+1, 27+18+17+8+7+6+3+1, 27+18+17+8+7+6+4+1, 27+18+17+8+7+6+4+2+1, 27+18+17+8+7+6+4+3+1, 27+18+17+8+7+6+5+4+1, 27+18+17+8+7+6+5+4+2+1, 27+18+17+8+7+6+5+4+3+1, 27+18+17+9+1, 27+18+17+9+2+1, 27+18+17+9+3+1, 27+18+17+9+4+1, 27+18+17+9+4+2+1, 27+18+17+9+4+3+1, 27+18+17+9+5+4+1, 27+18+17+9+5+4+2+1, 27+18+17+9+5+4+3+1, 27+18+17+9+6+1, 27+18+17+9+6+2+1, 27+18+17+9+6+3+1, 27+18+17+9+6+4+1, 27+18+17+9+6+4+2+1, 27+18+17+9+6+4+3+1, 27+18+17+9+6+5+4+1, 27+18+17+9+6+5+4+2+1, 27+18+17+9+6+5+4+3+1, 27+18+17+10+1, 27+18+17+10+2+1, 27+18+17+10+3+1, 27+18+17+10+4+1, 27+18+17+10+4+2+1, 27+18+17+10+4+3+1, 27+18+17+10+5+4+1, 27+18+17+10+5+4+2+1, 27+18+17+10+5+4+3+1, 27+18+17+10+6+1, 27+18+17+10+6+2+1, 27+18+17+10+6+3+1, 27+18+17+10+6+4+1, 27+18+17+10+6+4+2+1, 27+18+17+10+6+4+3+1, 27+18+17+10+6+5+4+1, 27+18+17+10+6+5+4+2+1, 27+18+17+10+6+5+4+3+1, 27+18+17+11+1, 27+18+17+11+2+1, 27+18+17+11+3+1, 27+18+17+11+4+1, 27+18+17+11+4+2+1, 27+18+17+11+4+3+1, 27+18+17+11+5+4+1, 27+18+17+11+5+4+2+1, 27+18+17+11+5+4+3+1, 27+18+17+11+6+1, 27+18+17+11+6+2+1, 27+18+17+11+6+3+1, 27+18+17+11+6+4+1, 27+18+17+11+6+4+2+1, 27+18+17+11+6+4+3+1, 27+18+17+11+6+5+4+1, 27+18+17+11+6+5+4+2+1, 27+18+17+11+6+5+4+3+1, 27+18+17+12+1, 27+18+17+12+2+1, 27+18+17+12+3+1, 27+18+17+12+4+1, 27+18+17+12+4+2+1, 27+18+17+12+4+3+1, 27+18+17+12+5+4+1, 27+18+17+12+5+4+2+1, 27+18+17+12+5+4+3+1, 27+18+17+13+12+1, 27+18+17+13+12+2+1, 27+18+17+13+12+3+1, 27+18+17+13+12+4+1, 27+18+17+13+12+4+2+1, 27+18+17+13+12+4+3+1, 27+18+17+13+12+5+4+1, 27+18+17+13+12+5+4+2+1, 27+18+17+13+12+5+4+3+1, 27+18+17+14+1, 27+18+17+14+2+1, 27+18+17+14+3+1, 27+18+17+14+4+1, 27+18+17+14+4+2+1, 27+18+17+14+4+3+1, 27+18+17+14+12+1, 27+18+17+14+12+2+1, 27+18+17+14+12+3+1, 27+18+17+14+12+4+1, 27+18+17+14+12+4+2+1, 27+18+17+14+12+4+3+1,

27+18+17+14+12+5+4+1, 27+18+17+14+12+5+4+2+1, 27+18+17+14+12+5+4+3+1, 27+18+17+15+1, 27+18+17+15+2+1, 27+18+17+15+3+1, 27+18+17+16+1, 27+18+17+16+2+1, 27+18+17+16+3+1, 27+18+17+16+15+1, 27+18+17+16+15+2+1, 27+18+17+16+15+3+1, 27+19+1, 27+19+2+1, 27+19+3+1, 27+19+4+1, 27+19+4+2+1, 27+19+4+3+1, 27+19+5+4+1, 27+19+5+4+2+1, 27+19+5+4+3+1, 27+19+6+1, 27+19+6+2+1, 27+19+6+3+1, 27+19+6+4+1, 27+19+6+4+2+1, 27+19+6+4+3+1, 27+19+6+5+4+1, 27+19+6+5+4+2+1, 27+19+6+5+4+3+1, 27+19+7+1, 27+19+7+2+1, 27+19+7+3+1, 27+19+7+4+1, 27+19+7+4+2+1, 27+19+7+4+3+1, 27+19+7+6+1, 27+19+7+6+2+1, 27+19+7+6+3+1, 27+19+7+6+4+1, 27+19+7+6+4+2+1, 27+19+7+6+4+3+1, 27+19+7+6+5+4+1, 27+19+7+6+5+4+2+1, 27+19+7+6+5+4+3+1, 27+19+8+1, 27+19+8+2+1, 27+19+8+3+1, 27+19+8+4+1, 27+19+8+4+2+1, 27+19+8+4+3+1, 27+19+8+5+4+1, 27+19+8+5+4+2+1, 27+19+8+5+4+3+1, 27+19+8+6+1, 27+19+8+6+2+1, 27+19+8+6+3+1, 27+19+8+6+4+1, 27+19+8+6+4+2+1, 27+19+8+6+4+3+1, 27+19+8+6+5+4+1, 27+19+8+6+5+4+2+1, 27+19+8+6+5+4+3+1, 27+19+8+7+1, 27+19+8+7+2+1, 27+19+8+7+3+1, 27+19+8+7+4+1, 27+19+8+7+4+2+1, 27+19+8+7+4+3+1, 27+19+8+7+6+1, 27+19+8+7+6+2+1, 27+19+8+7+6+3+1, 27+19+8+7+6+4+1, 27+19+8+7+6+4+2+1, 27+19+8+7+6+4+3+1, 27+19+8+7+6+5+4+1, 27+19+8+7+6+5+4+2+1, 27+19+8+7+6+5+4+3+1, 27+19+9+1, 27+19+9+2+1, 27+19+9+3+1, 27+19+9+4+1, 27+19+9+4+2+1, 27+19+9+4+3+1, 27+19+9+5+4+1, 27+19+9+5+4+2+1, 27+19+9+5+4+3+1, 27+19+9+6+1, 27+19+9+6+2+1, 27+19+9+6+3+1, 27+19+9+6+4+1, 27+19+9+6+4+2+1, 27+19+9+6+4+3+1, 27+19+9+6+5+4+1, 27+19+9+6+5+4+2+1, 27+19+9+6+5+4+3+1, 27+19+10+1, 27+19+10+2+1, 27+19+10+3+1, 27+19+10+4+1, 27+19+10+4+2+1, 27+19+10+4+3+1, 27+19+10+5+4+1, 27+19+10+5+4+2+1, 27+19+10+5+4+3+1, 27+19+10+6+1, 27+19+10+6+2+1, 27+19+10+6+3+1, 27+19+10+6+4+1, 27+19+10+6+4+2+1, 27+19+10+6+4+3+1, 27+19+10+6+5+4+1, 27+19+10+6+5+4+2+1, 27+19+10+6+5+4+3+1, 27+19+11+1, 27+19+11+2+1, 27+19+11+3+1, 27+19+11+4+1, 27+19+11+4+2+1, 27+19+11+4+3+1, 27+19+11+5+4+1, 27+19+11+5+4+2+1, 27+19+11+5+4+3+1, 27+19+11+6+1, 27+19+11+6+2+1, 27+19+11+6+3+1, 27+19+11+6+4+1, 27+19+11+6+4+2+1, 27+19+11+6+4+3+1, 27+19+11+6+5+4+1, 27+19+11+6+5+4+2+1, 27+19+11+6+5+4+3+1, 27+19+12+1, 27+19+12+2+1, 27+19+12+3+1, 27+19+12+4+1, 27+19+12+4+2+1, 27+19+12+4+3+1, 27+19+12+5+4+1, 27+19+12+5+4+2+1, 27+19+12+5+4+3+1, 27+19+13+12+1, 27+19+13+12+2+1, 27+19+13+12+3+1, 27+19+13+12+4+1, 27+19+13+12+4+2+1, 27+19+13+12+4+3+1, 27+19+13+12+5+4+1, 27+19+13+12+5+4+2+1, 27+19+13+12+5+4+3+1, 27+19+14+1, 27+19+14+2+1, 27+19+14+3+1, 27+19+14+4+1, 27+19+14+4+2+1, 27+19+14+4+3+1, 27+19+14+12+1, 27+19+14+12+2+1, 27+19+14+12+3+1, 27+19+14+12+4+1, 27+19+14+12+4+2+1, 27+19+14+12+4+3+1, 27+19+14+12+5+4+1, 27+19+14+12+5+4+2+1, 27+19+14+12+5+4+3+1, 27+19+15+1, 27+19+15+2+1, 27+19+15+3+1, 27+19+16+1, 27+19+16+2+1, 27+19+16+3+1, 27+19+16+15+1, 27+19+16+15+2+1, 27+19+16+15+3+1, 27+19+17+1, 27+19+17+2+1, 27+19+17+3+1, 27+19+17+4+1, 27+19+17+4+2+1, 27+19+17+4+3+1, 27+19+17+5+4+1, 27+19+17+5+4+2+1, 27+19+17+5+4+3+1, 27+19+17+6+1, 27+19+17+6+2+1, 27+19+17+6+3+1, 27+19+17+6+4+1, 27+19+17+6+4+2+1, 27+19+17+6+4+3+1, 27+19+17+6+5+4+1, 27+19+17+6+5+4+2+1, 27+19+17+6+5+4+3+1, 27+19+17+7+1, 27+19+17+7+2+1, 27+19+17+7+3+1, 27+19+17+7+4+1, 27+19+17+7+4+2+1, 27+19+17+7+4+3+1, 27+19+17+7+6+1, 27+19+17+7+6+2+1, 27+19+17+7+6+3+1, 27+19+17+7+6+4+1, 27+19+17+7+6+4+2+1, 27+19+17+7+6+4+3+1, 27+19+17+7+6+5+4+1, 27+19+17+7+6+5+4+2+1, 27+19+17+7+6+5+4+3+1, 27+19+17+8+1, 27+19+17+8+2+1, 27+19+17+8+3+1, 27+19+17+8+4+1, 27+19+17+8+4+2+1, 27+19+17+8+4+3+1, 27+19+17+8+5+4+1, 27+19+17+8+5+4+2+1, 27+19+17+8+5+4+3+1, 27+19+17+8+6+1, 27+19+17+8+6+2+1, 27+19+17+8+6+3+1, 27+19+17+8+6+4+1, 27+19+17+8+6+4+2+1, 27+19+17+8+6+4+3+1, 27+19+17+8+6+5+4+1, 27+19+17+8+6+5+4+2+1, 27+19+17+8+6+5+4+3+1, 27+19+17+8+7+1, 27+19+17+8+7+2+1, 27+19+17+8+7+3+1, 27+19+17+8+7+4+1, 27+19+17+8+7+4+2+1, 27+19+17+8+7+4+3+1, 27+19+17+8+7+6+1, 27+19+17+8+7+6+2+1, 27+19+17+8+7+6+3+1, 27+19+17+8+7+6+4+1, 27+19+17+8+7+6+4+2+1, 27+19+17+8+7+6+4+3+1, 27+19+17+8+7+6+5+4+1, 27+19+17+8+7+6+5+4+2+1, 27+19+17+8+7+6+5+4+3+1, 27+19+17+9+1, 27+19+17+9+2+1, 27+19+17+9+3+1, 27+19+17+9+4+1, 27+19+17+9+4+2+1, 27+19+17+9+4+3+1, 27+19+17+9+5+4+1, 27+19+17+9+5+4+2+1, 27+19+17+9+5+4+3+1, 27+19+17+9+6+1, 27+19+17+9+6+2+1, 27+19+17+9+6+3+1, 27+19+17+9+6+4+1, 27+19+17+9+6+4+2+1, 27+19+17+9+6+4+3+1, 27+19+17+9+6+5+4+1, 27+19+17+9+6+5+4+2+1, 27+19+17+9+6+5+4+3+1, 27+19+17+10+1, 27+19+17+10+2+1, 27+19+17+10+3+1, 27+19+17+10+4+1, 27+19+17+10+4+2+1, 27+19+17+10+4+3+1, 27+19+17+10+5+4+1, 27+19+17+10+5+4+2+1, 27+19+17+10+5+4+3+1, 27+19+17+10+6+1, 27+19+17+10+6+2+1, 27+19+17+10+6+3+1, 27+19+17+10+6+4+1, 27+19+17+10+6+4+2+1, 27+19+17+10+6+4+3+1, 27+19+17+10+6+5+4+1, 27+19+17+10+6+5+4+2+1, 27+19+17+10+6+5+4+3+1, 27+19+17+11+1, 27+19+17+11+2+1, 27+19+17+11+3+1, 27+19+17+11+4+1, 27+19+17+11+4+2+1, 27+19+17+11+4+3+1, 27+19+17+11+5+4+1, 27+19+17+11+5+4+2+1, 27+19+17+11+5+4+3+1, 27+19+17+11+6+1, 27+19+17+11+6+2+1, 27+19+17+11+6+3+1, 27+19+17+11+6+4+1, 27+19+17+11+6+4+2+1, 27+19+17+11+6+4+3+1, 27+19+17+11+6+5+4+1, 27+19+17+11+6+5+4+2+1, 27+19+17+11+6+5+4+3+1, 27+19+17+12+1, 27+19+17+12+2+1, 27+19+17+12+3+1, 27+19+17+12+4+1, 27+19+17+12+4+2+1, 27+19+17+12+4+3+1, 27+19+17+12+5+4+1, 27+19+17+12+5+4+2+1, 27+19+17+12+5+4+3+1, 27+19+17+13+12+1, 27+19+17+13+12+2+1, 27+19+17+13+12+3+1, 27+19+17+13+12+4+1, 27+19+17+13+12+4+2+1, 27+19+17+13+12+4+3+1, 27+19+17+13+12+5+4+1, 27+19+17+13+12+5+4+2+1, 27+19+17+13+12+5+4+3+1, 27+19+17+14+1, 27+19+17+14+2+1, 27+19+17+14+3+1, 27+19+17+14+4+1, 27+19+17+14+4+2+1, 27+19+17+14+4+3+1, 27+19+17+14+12+1, 27+19+17+14+12+2+1, 27+19+17+14+12+3+1, 27+19+17+14+12+4+1, 27+19+17+14+12+4+2+1, 27+19+17+14+12+4+3+1, 27+19+17+14+12+5+4+1, 27+19+17+14+12+5+4+2+1, 27+19+17+14+12+5+4+3+1, 27+19+17+15+1, 27+19+17+15+2+1, 27+19+17+15+3+1, 27+19+17+16+1, 27+19+17+16+2+1, 27+19+17+16+3+1, 27+19+17+16+15+1, 27+19+17+16+15+2+1, 27+19+17+16+15+3+1, 27+20+1, 27+20+2+1, 27+20+3+1, 27+21+20+1, 27+21+20+2+1, 27+21+20+3+1, 27+22+20+1, 27+22+20+2+1, 27+22+20+3+1, 27+23+20+1, 27+23+20+2+1, 27+23+20+3+1, 27+23+21+20+1, 27+23+21+20+2+1, 27+23+21+20+3+1, 27+23+22+20+1,

27+23+22+20+2+1, 27+23+22+20+3+1, 27+24+20+1, 27+24+20+2+1, 27+24+20+3+1, 27+24+21+20+1, 27+24+21+20+2+1, 27+24+21+20+3+1, 27+24+22+20+1, 27+24+22+20+2+1, 27+24+22+20+3+1 and 28.

In the list above, the numbers refer to the embodiments according to their numbering provided hereinabove whereas "+" indicates the dependency from another embodiment. The different individualised embodiments are separated by commas. In other words, "5+4+1" for example refers to embodiment 5) depending on embodiment 4), depending on embodiment 1), i.e. embodiment "5+4+1" corresponds to embodiment 1) further limited by the features of embodiments 4) and 5). Likewise, "18+16+3+1" refers to embodiment 18) depending mutatis mutandis on embodiments 16) and 13), depending on embodiment 1), i.e. embodiment "18+16+3+1" corresponds to embodiment 1) further limited by the features of embodiment 3), further limited by the features of embodiments 16) and 18).

The compounds of formula I can be manufactured in accordance with the present invention using the procedures described hereafter.

Preparation of Compounds of Formula I
General Preparation Methods:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures. Sections a) to f) hereafter describe general methods for preparing compounds of formula I. If not indicated otherwise, the generic groups K (Ka, Kb, Kc and Kd), $R^{1a}$, $R^{1b}$, $R^{1c}$, $R^{1d}$, $U^a$, $V^a$, $W^a$, $U^b$, $V^b$, $W^b$, $V^c$, $W^c$, $V^d$, $W^d$, $X^a$, $R^a$, A, $R^b$, G (Ga, Gb, Gc and Gd), M, Q and Q' are as defined for formula I. General synthetic methods used repeatedly throughout the text below are referenced to and described in the section entitled "General reaction techniques" in the experimental section below. In some instances generic groups might be incompatible with the assembly illustrated in the procedures and schemes below and so will require the use of protecting groups. The use of protecting groups is well known in the art (see for example "*Protective Groups in Organic Synthesis*", T. W. Greene, P. G. M. Wuts, Wiley-Interscience, 1999).

The compounds of formula I can be manufactured by
a) reacting a compound of formula II

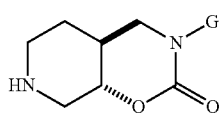

with an alkene derivative of formulae IIIa or IIIb

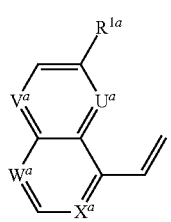

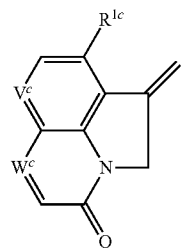

using general reaction technique 1; or
b) reacting a compound of formula II with an epoxide of formula IVa, IVb or IVc

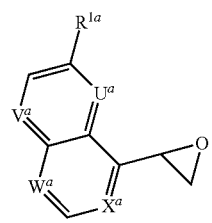

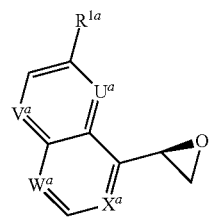

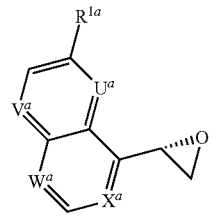

using general reaction technique 2; or
c) reacting a compound of formula II with an aldehyde of formula V

wherein K is as defined in formula I, provided that when K is Ka, A is $CH_2$, using general reaction technique 3; or
d) reacting a compound of formula II with a compound of formula VI

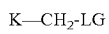

wherein LG represents chloro, bromo, iodo, OTf, OTs or OMs. The reaction can be performed in various solvents such as DMF, DMA, NMP, in presence of a base such as DIPEA or TEA at a temperature ranging between 20° C. and 100° C.; or
e) reacting a compound of formula VII

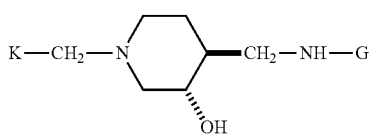

VII wherein when K is Ka A is CH$_2$, with a carbonic acid derivative of formula VIII,

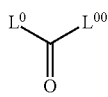

VIII wherein L$^0$ and L$^{00}$ both represent chloro, OCCl$_3$, imidazolyl or succinimidyloxy, or L$^0$ represents chloro and L$^{00}$ represents OCCl$_3$ using general reaction technique 4; or f) deprotecting a compound of formula IX

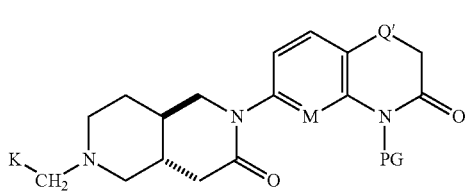

IX wherein PG represents 4-methoxybenzyl or 2,4-dimethoxybenzyl or 3,4-dimethoxybenzyl. The deprotection reaction can be performed using acidic conditions such as TFA, TfOH, or a combination of TFA and TfOH at a temperature ranging between 20° C. and 100° C.

The compounds of formula I thus obtained may be, if desired, converted into their salts, and notably into their pharmaceutically acceptable salts.

Besides, whenever the compounds of formula I are obtained in the form of mixtures of diastereomers, the diastereomers can be separated using methods known to one skilled in the art, e.g. by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as TEA or diethylamine) and eluent B (Hex), at a flow rate of 0.8 to 150 mL/min. The mixtures of diasteromers may also be separated by an appropriate combination of silica gel chromatography, HPLC and crystallization techniques.

Preparation of the Intermediates Used in the Preparation the Compounds of Formula I:

Compounds of Formula II:

The compounds of formula II can be prepared as summarised in Scheme 1 hereafter.

Scheme 1

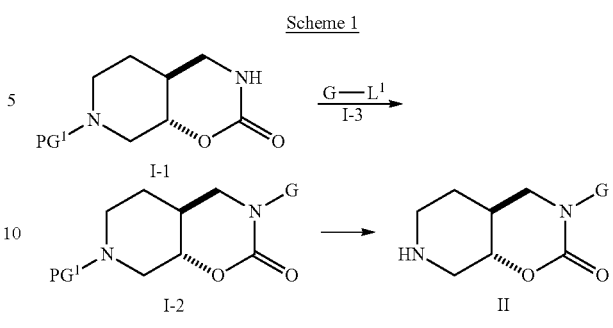

In Scheme 1, PG$^1$ is an amine protecting group, such as a Boc, Cbz, Alloc or Fmoc and L$^1$ represents Cl, Br, I or OTf.

The compounds of formula I-1 are reacted with compounds of formula I-3 using general reaction technique 5 to give the intermediates of formula I-2. Removal of the protecting group using general reaction technique 6 provides the compounds of formula II.

Compounds of Formulae IIIa and IIIb:

The compounds of formula IIIa can be prepared as described in WO 02/08224, WO 2004/058144, WO 2006/021448, WO 2007/016610, WO 2007/107965 and WO 2010/041194 or by analogy to these reported methods. The compounds of formula IIIb can be prepared as described in WO 2007/071936 and WO 2010/041194 or by analogy to these reported methods.

Compounds of Formulae IVa, IVb and IVc:

The compounds of formulae IVa, IVb and IVc can be prepared as described in WO 00/78748, WO 02/08224, WO 2006/02047, WO 2006/21448 and WO 2006/032466.

Compounds of Formula V:

The compounds of formula V wherein K represents Ka, A represents CH$_2$, U is CH and V or W is N can be prepared as described in WO 2005/16916 and WO 2005/108389. The other azaisosters can be prepared by analogy to these reported methods.

The compounds of formula V wherein K represents Kb can be prepared as described in WO 2006/137485, WO 2007/138974, WO 2009/09700 and WO 2009/69589.

The compounds of formula V wherein K represents Kc can be prepared by oxidation of the corresponding primary alcohols using general reaction technique 7. The precursors (Vc=N and Wc=CH) can be obtained as described in WO 2008/125594 and WO 2010/041194.

The compounds of formula V wherein K represents Kd can be prepared by oxidation of the corresponding primary alcohols using general reaction technique 7. The precursors (Vd=N and Wd=CH) can be obtained as described in WO 2009/104147. The azaisosters (e.g. Vd=CH and Wd=N) can be obtained in analogy to the reported methods.

Compounds of Formula VI:

The compounds of formula VI can be prepared as summarised in Scheme 2 hereafter.

Scheme 2

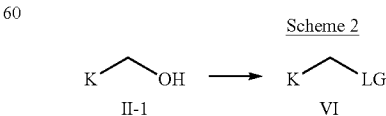

In Scheme 2, LG represents OTf, OMs, OTf or halogen such as bromine, chlorine or iodine.

The compounds of formula VI can be prepared from compounds of formula II-1 using general reaction technique 8.

Compounds of Formula VII:

The compounds of formula VII can be prepared as summarised in Scheme 3 hereafter.

Scheme 3

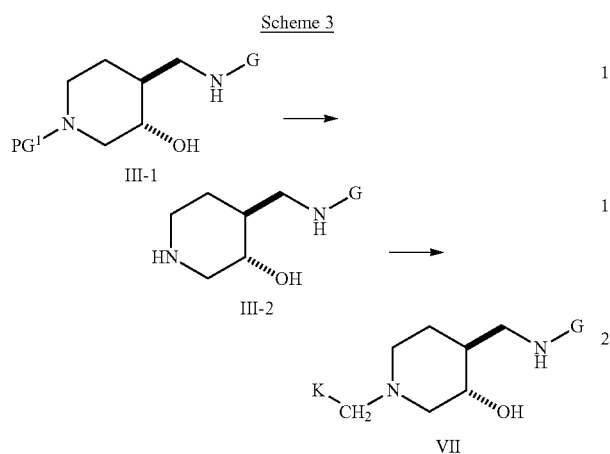

In Scheme 3, G is as defined in formula VII, PG$^1$ is an amine protecting group, such as a Boc, Cbz, Alloc or Fmoc and k is as defined in formula I, provided that A represents CH$_2$.

The compounds of formula III-1 can be deprotected (Scheme 3) using general reaction technique 6, leading to the intermediates of formula III-2. The formation of the compounds of formula VII can then be achieved using methods which have been described for the preparation of compounds of formula I wherein A is CH$_2$, section a), c), d) and f) using respectively precursors of formulae IIIa, IIIb, V and VI.

Compounds of Formula VIII:

The compounds of formula VIII are commercially available.

Compounds of Formula IX:

The compounds of formula IX can be prepared as summarised in Scheme 4 hereafter.

Scheme 4

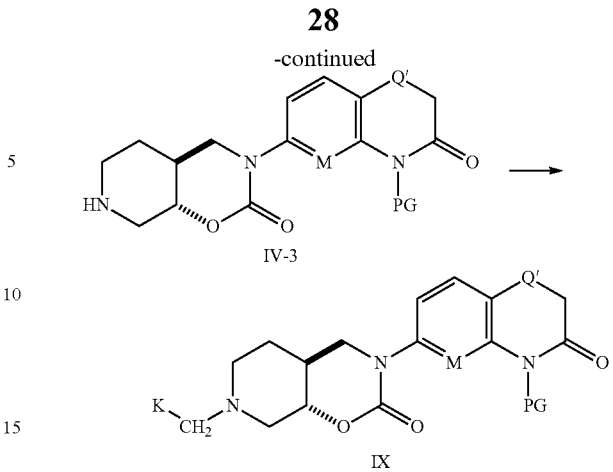

In Scheme 4, PG represents 4-methoxybenzyl, 2,4-dimethoxybenzyl or 3,4-dimethoxybenzyl, PG$^1$ is an amine protecting group, such as a Boc, Cbz, Alloc or Fmoc, L$^2$ represents OTf or a halogen such as Cl, Br or I.

The compounds of formula I-1 can be reacted (Scheme 4) with the compounds of formula IV-1, wherein L$^2$ represents OTf or a halogen such as Cl, Br or I using general reaction technique 5. The protecting group PG$^1$ in the intermediates of formula IV-2 is removed using general reaction technique 6 affording the intermediates of formula IV-3 which are further transformed into the derivatives of formula IX using methods which have been described for the preparation of compounds of formula I wherein A is CH$_2$, section a), c), d) and f), using respectively precursors of formulae IIIa, IIIb, V and VI.

Synthesis of Building Blocks:

Compounds of Formula I-1:

The compounds of formula I-1 can be prepared as summarised in Scheme 5 hereafter.

Scheme 5

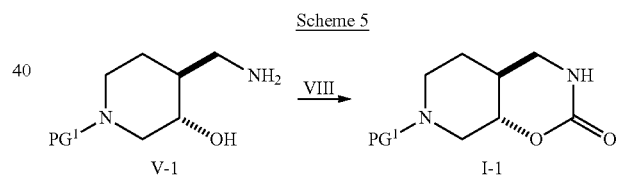

In Scheme 5, PG$^1$ represents an amino protecting group such Boc or Cbz.

The derivatives of formula V-1 (commercially available when PG$^1$ represents Cbz or Boc) can be reacted with the derivatives of formula VIII using general reaction technique 4.

Compounds of Formula I-3:

The compounds of formula I-3 are either commercially available (G represents Ga) or can be made according to WO 2008/009700 (G represents Gc), WO 2009/71890, WO 2010/30782, WO 2010/41194 or WO 2011/057892 (G represents Gd).

Compounds of Formula II-1

The compounds of formula II-1 wherein K represents Ka can be obtained by reduction of the corresponding aldehydes using general reaction technique 9. The required aldehydes can be made according to J Chem. Soc. (1957), 3066-3071, WO 02/089749, WO 2003/050132, WO 2005/108389, WO 2005/016916 or in analogy to methods reported therein.

The compounds of formula II-1 wherein K represents Kb can be obtained according to WO 2006/137485, WO 2007/138974, WO 2008/009700 and WO 2009/069589.

The compounds of formula II-1 wherein K represents Kc are obtained by reduction of the corresponding aldehydes using general reaction technique 9. The required aldehydes are made according to WO 201041194 or in analogy to the method reported therein.

The compounds of formula II-1 wherein K represents Kd can be obtained by reduction of the corresponding aldehydes using general reaction technique 9. The required aldehydes can be made according to WO 2008/03690 and WO 2009/104147 or in analogy to the methods reported therein.

Compounds of Formula III-1:

The compounds of formula III-1 can be prepared as summarised in Scheme 6 hereafter.

Scheme 6

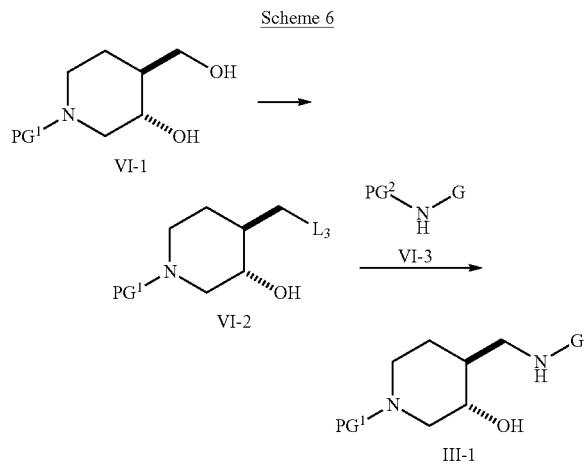

In Scheme 6, G is as defined in formula I. $PG^1$ and $PG^2$ are orthogonal amine protecting groups, such as a Boc, alloc, Cbz or Fmoc. $L^3$ is Cl, Br, I, OMs, OTs or OTf.

The compounds of formula VI-2 can be obtained (Scheme 6) from the compounds of formula VI-1 (commercially available when $PG^1$ represents Cbz or Boc) using general technique reaction 8. The sodio anion of compounds of formula VI-3 which are formed by reacting the compounds of formula VI-3 with sodium hydride in an appropriate solvent such as DMF are subsequently reacted with the compound of formula VI-2 at a temperature ranging between 25° C. and 100° C. and especially at 60° C. to afford directly the compounds of formula III-1. If required, the protecting group $PG^2$ can be removed using general reaction technique 6.

Compounds of Formula IV-1:

The compounds of formula IV-1 can be prepared as summarised in Scheme 7 hereafter.

Scheme 7

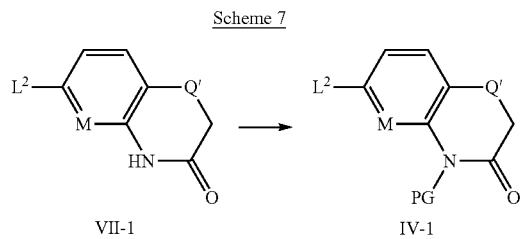

In Scheme 7, $L^2$ is Cl, Br or I. PG is an amine protecting group such as a 4-methoxybenzyl or 3,4-dimethoxybenzyl, Q' represents O or S and M is N or CH.

The compounds of formula VII-1 can be reacted with 4-methoxybenzyl, 2,4-dimethoxybenzyl or 3,4-dimethoxybenzyl chloride in the presence of a base such as $Cs_2CO_3$ in a solvent such as DMF at a temperature ranging between 20° C. and 100° C., affording the compound of formula IV-1.

Compounds of Formula V-1:

The compound of formula V-1 wherein $PG^1$ is Boc is commercially available. The other analogues can be made from (3R,4R)-4-(aminomethyl)-3-piperidinol (prepared according to WO 2005/000838) using general reaction technique 10.

Compounds of Formula VI-3:

Compounds of formula VI-3 can be prepared according to WO 2004/09562, WO 2007/107965, WO 2008/126024 and WO 2009/104159 or prepared (when $PG^2$ represents Boc) as described in Scheme 8 hereafter.

Scheme 8

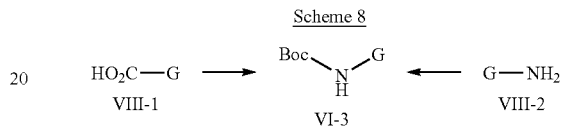

In Scheme 8, G represents Ga, Gb or Gc.

The compound of formula VI-3, wherein G represents Gc and $PG^2$ represents Boc can be prepared from the corresponding acids of formula VIII-1 via a Curtius reaction. The compounds of formula VIII-1 can for instance be reacted with DPPA in 2-methyl-2-propanol in presence of TEA at a temperature between 50° C. and reflux. Alternatively the compounds of formula VI-3 can be prepared from the compounds of formula VIII-2 using general reaction technique 10.

Compounds of Formula VII-1:

The compounds of formula VII-1 are commercially available or can be prepared according to WO 2010/041194 and WO 2010/30782.

Compounds of Formula VIII-1:

The compounds of formula VIII-1 are either commercially available or can be prepared according to WO 2004/58144, WO 02/56882, WO 2006/105289, WO 2007/16610 or J Org. Chem. (1968), 33(1), 456-457. In case G represents Gc, they can also be obtained by saponification of the corresponding ester using general reaction technique 11 as shown in Scheme 9 hereafter. The required esters can be prepared according to WO 2007/081597.

Scheme 9

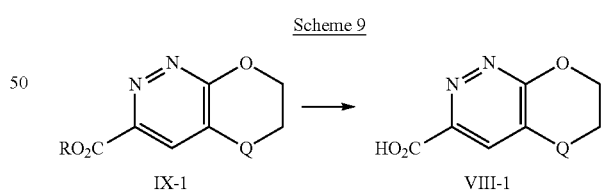

In scheme 9, Q is O or S and R is alkyl.

Compounds of Formula VIII-2:

Compounds of formula VIII-2 are either commercially available or prepared according to WO 2007/100758, WO 2007/107905 or WO 2010/30782.

EXPERIMENTAL PART

Abbreviations

The following abbreviations are used throughout the specification and the examples:

Ac acetyl
AcOH acetic acid
Alloc allyloxycarbonyl
aq. aqueous
BINAP (±)-(1,1'-binaphthalene-2,2'-diyl)bis(diphenylphosphine)
Boc tert-butoxycarbonyl
BrettPhos 2-(dicyclohexylphosphino)3,6-dimethoxy-2',4',6'-triisopropyl-1,1'-biphenyl
Cbz benzyloxycarbonyl
CC column chromatography over silica gel
Cy cyclopentyl
CDI carbonyldiimidazole
Dba dibenzylideneacetone
DCE 1,2-dichloroethane
DCM dichloromethane
DIPEA N,N-diisopropylethylamine
DMA dimethylacetamide
DMAP 4-dimethylaminopyridine
DME 1,2-dimethoxyethane
DMF N,N-dimethylformamide
DMSO dimethylsulfoxide
EA ethyl acetate
ESI Electron Spray Ionisation
eq. equivalent
ether diethyl ether
Et ethyl
EtOH ethanol
Fmoc 9-fluorenylmethoxycarbonyl
h hour(s)
Hex hexane
Hept heptanes
HPLC high pressure liquid chromatography
IPr 1,3-bis(2,6-diisopropylphenyl)-1,3-dihydro-2H-imidazol-2-ylidene
JosiPhos ligands (R)-1-[SP)-2-(di-tert-butylphosphino)ferrocenyl]ethylbis(2-methyl-phenyl)phosphine or (R)-1-[(SP)-2-(di-tert-butyl-phosphino)ferrocenyl]ethyldiphenylphosphine or (R)-1-[(SP)-2-(dicyclohexylphosphino)ferrocenyl]ethyl-di-tert-butylphosphine
KHMDS potassium hexamethyldisilazide
LAH lithium aluminium hydride
LC liquid chromatography
LiHMDS lithium hexamethyldisilazide
Me methyl
MeCN acetonitrile
MEK methyl ethyl ketone
MeOH methanol
min minute(s)
MS Mass Spectroscopy
Ms methanesulfonyl (mesyl)
n-BuLi n-butyl lithium
NMO N-methylmorpholine oxide
NMP N-methyl-2-pyrrolidone
org. organic
Pd/C palladium on carbon
Pd/CaCO$_3$ palladium dihydroxide on calcium carbonate
Pd(OH)$_2$/C palladium dihydroxide on carbon
PEPPSI™-IPr [1,3-bis(2,6-diisopropylphenyl)imidazol-2-ylidene](3-chloropyridyl)palladium(II) dichloride
Ph phenyl
PMB para-methoxybenzyl
Pyr pyridine
Q-phos 1,2,3,4,5-pentaphenyl-1'-(di-tert-butylphosphino)ferrocene
quant. quantitative
rac racemic
rt room temperature
sat. saturated
SK-CC01-A 2'-(dimethylamino)-2-biphenylyl-palladium(II) chloride dinorbornylphosphine complex
SK-CC02-A 2-(dimethylaminomethyl)ferrocen-1-yl-palladium(II) chloride dinorbornylphosphine complex
S-Phos 2-dicyclohexylphosphino-2',6'-dimethoxybiphenyl
TBAF tetrabutylammonium fluoride
TBDMS tert-butyldimethylsilyl
TBDPS tert-butyldiphenylsilyl
TBME tert-butylmethylether
tBu tert-butyl
TEA triethylamine
Tf trifluoromethanesulfonyl (triflyl)
TFA trifluoroacetic acid
THF tetrahydrofuran
TMG 1,1,3,3-tetramethylguanidine
TMS trimethylsilyl
t$_R$ retention time
Ts para-toluenesulfonyl
T3P propylphosphonic anhydride
XantPhos 4,5-bis(diphenylphosphino)-9,9-dimethylxanthene
X-Phos 2-dicyclohexylphosphino-2',4',6'-triisopropylbiphenyl General Reaction Techniques:

General Reaction Technique 1 (Addition of Piperidine Derivative onto an Alkene):

The addition of a piperidine derivative onto an alkene can be accomplished in various solvents such as DMF, DMA or NMP in presence of a promoter such a TMG at a temperature ranging between 60° C. and 100° C.

General Reaction Technique 2 (Addition of Piperidine Derivative onto an Epoxide):

The addition of a piperidine derivative onto an epoxide can be accomplished in various solvent such as DMF, DMA, NMP in presence of a mineral base such as K$_2$CO$_3$ and a Lewis acid such as LiClO$_4$ at a temperature ranging between 60° C. and 100° C.

General Reaction Technique 3 (Reductive Amination):

The reaction between an amine and an aldehyde is performed in a solvent system allowing the removal of the formed water through physical or chemical means (e.g. distillation of the solvent-water azeotrope or presence of drying agents such as molecular sieves, MgSO$_4$ or Na$_2$SO$_4$). Such solvent is typically toluene, Hex, THF, NMP, DCM or DCE or a mixture of solvents such as DCE/MeOH. The reaction can be catalyzed by traces or a stoichiometric amount of acid (usually AcOH or p-TsOH). The intermediate imine is reduced with a suitable reducing agent (e.g. NaBH$_4$, NaBH$_3$CN, or NaBH(OAc)$_3$) or by hydrogenation over a noble metal catalyst such as Pd/C. The reaction is carried out between −10° and +110° C., preferably between 0° C. and 60° C. The reaction can also be carried out in one pot. It can also be performed in protic solvents such as MeOH or water in the presence of a picoline-borane complex (*Tetrahedron* (2004), 60, 7899-7906).

General Reaction Technique 4 (Cyclic Carbamate Formation):

The aminoalcohol derivative was reacted with phosgene, diphosgene, triphosgene, carbonyldiimidazole or di-O-succinyl carbonate. The reaction is preferably carried out in a dry aprotic solvent such as DCM or THF in presence of an organic base such as TEA or pyridine and at a temperature range between −78° C. and +80° C.

General Reaction Technique 5 (Buchwald-Hartwig Coupling):

The halide or triflate aromatic partner is reacted with the required 7-protected octahydro-2H-pyrido[4,3-e][1,3]oxazin-2-one derivative in the presence of a palladium catalyst in a solvent such as toluene, THF, dioxane, DME or DMF. Examples of typical palladium catalysts are triarylphosphine palladium complexes such as Pd(PPh$_3$)$_4$. These catalysts can also be prepared in situ from a common palladium source such as Pd(OAc)$_2$ or Pd$_2$(dba)$_3$ and a ligand such as trialkylphosphines (e.g. PCy$_3$ or P(tBu)$_3$), dialkylphosphinobiphenyls (e.g. X-Phos or BrettPhos), chelating diphosphines (e.g. BINAP, XantPhos) or ferrocenylphosphines (e.g. Q-phos). One can also use instead, a commercially available precatalyst based on palladacycle (e.g. SK-CC02-A) or N-heterocyclic carbene complexes (e.g. PEPPSI™-IPr). Alternatively, a copper catalysed coupling reaction between the above mentioned partners can be performed using a copper (I) source such as copper iodide, a ligand such as trans-N,N'-dimethyl-1,2-cyclohexanediamine, a base such as K$_2$CO$_3$ in a solvent such as dioxane at a temperature ranging between 50° C. and reflux.

General Reaction Technique 6 (Removal of Amine Protecting Groups):

The benzyl carbamates are deprotected by hydrogenolysis over a noble metal catalyst (e.g. Pd/C or Pd(OH)$_2$/C). The Boc group is removed under acidic conditions such as HCl in an organic solvent such as MeOH or dioxane, or TFA neat or diluted in a solvent such DCM. The Alloc group is removed by the action of tetrakis(triphenylphosphine)palladium(0) in presence of an allyl cation scavenger such as morpholine, dimedone or tributyltin hydride between 0° C. and +50° C. in a solvent such as THF. The Fmoc group is removed under mild basic conditions such as piperidine in DMF. The N-acetyl protecting group is removed under basic conditions such as Na$_2$CO$_3$, LiOH or NaOH in aq. MeOH or THF, or under acidic conditions such as aq. HCl in THF. The N-benzyl protected amines are deprotected by hydrogenolysis over a noble catalyst (e.g. Pd(OH)$_2$). The 2,4-dimethoxybenzyl, 3,4-dimethoxybenzyl or 4-methoxybenzyl protecting group can be removed by reaction with TFA. Further general methods to remove amine protecting groups have been described in *Protecting Groups in Organic Synthesis*, 3$^{rd}$ Ed 1999, 494-653; T. W. Greene, P. G. M. Wuts (Publisher: John Wiley and Sons, Inc., New York).

General Reaction Technique 7 (Alcohol Oxidation):

A primary allylic or benzylic alcohol dissolved in an organic solvent such as DCM or THF is oxidized into the corresponding aldehyde with MnO$_2$. Further methods can be found in *Comprehensive Organic Transformations. A guide to Functional Group Preparations*; 2$^{nd}$ Edition, R. C. Larock, Wiley-VC; New York, Chichester, Weinheim, Brisbane, Singapore, Toronto, 1999; Section aldehydes and ketones, p. 1234-1236

General Reaction Technique 8 (Alcohol Activation):

The alcohol is reacted with MsCl, TfCl or TsCl in presence of a base such as TEA in a dry aprotic solvent such as Pyr, THF or DCM between −30° C. and +50° C. In the case of the triflate or mesylate, Tf$_2$O or Ms$_2$O can also be used. These sulfonates can be reacted with a sodium halogenide such as NaI or NaBr in MeCN or DMF between 40° C. and 120° C. delivering the corresponding iodide derivatives. Alternatively the corresponding bromides or chlorides can also be obtained by reaction of the corresponding alcohol derivatives with PBr$_3$ or PCl$_3$ respectively.

General Reaction Technique 9 (Aldehyde and Ketone Reduction):

A ketone or an aldehyde is reduced with a boron or aluminium hydride reducing agent such as LiBH$_4$, NaBH$_4$ or LAH in a solvent such as THF between −20° C. and +40° C. Further general methods to reduce carbonyl groups as well as asymmetric reduction methods have been described in *Comprehensive Organic Transformations. A guide to Functional Group Preparations*, 2nd Edition, R. C. Larock, Wiley-VC, New York, Chichester, Weinheim, Brisbane, Singapore, Toronto 1999, Section alcohols and phenols, p. 1075-1087 and p. 1097-1110.

General Reaction Technique 10 (Protection of an Amine):

Amines are usually protected as carbamates such as Alloc, Cbz, Boc or Fmoc. They are obtained by reacting the amine with allyl- or benzyl-chloroformate, di tert-butyl dicarbonate or Fmoc chloride in presence of a base such as NaOH, TEA, DMAP or imidazole. Further strategies to introduce other amine protecting groups have been described in Protecting Groups in Organic Synthesis, 3rd Ed (1999), 494-653; T. W. Greene, P. G. M. Wuts; (Publisher: John Wiley and Sons, Inc., New York, N.Y.).

General Reaction Technique 11 (Ester Hydrolysis):

The methyl and ethyl esters are deprotected by saponification with an alkali hydroxide such as NaOH, LiOH or KOH, benzyl ester by hydrogenolysis over a noble metal catalyst such as Pd/C. The tert-butyl esters are deprotected by treatment with TFA (neat or diluted in an organic solvent such as DCM) or a solution of HCl in an organic solvent such as dioxane.

Detailed Synthetic Procedures $^1$H NMR spectra were recorded on a 300 MHz VARIAN GEMINI spectrometer and are reported relative to the indicated deuterated solvent signals (δ CDCl$_3$: 7.26 ppm and δ DMSO: 2.54 ppm). Multiplicities: s=singlet, d=doublet, t=triplet, q=quadruplet, p=pentuplet, hex=hexet, hep=heptet, m=multiplet, br.=broad; coupling constants are given in Hz.

Preparative HPLCs were performed on XBridge Prep C18 columns from Waters. The following conditions were used:

Eluents: A: H$_2$O+0.1% acidic or basic additive; B: MeCN+ 0.1% acidic or basic additive;

Gradient: 5% B→95% B over 5 min.

Detection: UV/Vis and/or MS and/or ELSD.

Method A: Prep-HPLC (basic conditions): additive in A and B is 0.1% NH$_4$OH.

Method B: Prep-HPLC (acidic conditions): additive in A and B is 0.1% HCO$_2$H.

Preparation A: rac-(4aR*,8aR*)-tert-butyl 2-oxo-hexahydro-2H-pyrido[4,3-e][1,3]oxazine-7(3H)-carboxylate To a mixture of rac-(3R*,4R*)-tert-butyl 4-(aminomethyl)-3-hydroxypiperidine-1-carboxylate (3.39 g, 14.72 mmol; prepared according to *Tetrahedron* (2008), 64, 2456-2464) in MEK (40 mL) heated to 60° C. was added CDI (3.58 g, 22.08 mmol, 1.5 eq). The mixture was stirred for 3 h. Na$_2$CO$_3$ (5% aq., 4 mL) was added. The reaction proceeded at rt for 70 min. The two layers were decanted and the aq. layer was extracted with EA (10 mL). The combined org. layers were washed with brine (8 mL), dried over Na$_2$SO$_4$, filtered and concentrated to dryness. The residue was purified by CC (DCM to DCM/MeOH 9:1) to afford the title compound as a white solid (2.59 g).

$^1$H NMR (d6-DMSO) δ: 7.23 (d, J=3.7 Hz, 1H); 4.111 (m, 1H); 3.94 (m, 1H); 3.79 (td, J=5.0, 10.4 Hz, 1H); 3.14 (td, J=5.0, 11.2 Hz, 1H); 2.87 (t, J=11.2 Hz, 1H); 2.55-2.80 (m,

2H); 1.64-1.76 (m, 2H); 1.38 (s, 9H), 1.12 (m, 1H). MS (ESI, m/z): 257.2 [M+H$^+$] for $C_{12}H_{20}N_2O_4$.

Preparation B: rac-(4aR*,8aR*)-3-(2,3-dihydrobenzo[b][1,4]dioxin-6-yl)octahydro-2H-pyrido[4,3-e][1,3]oxazin-2-one B.i. Rac-(4aR*,8aR*)-tert-butyl 3-(2,3-dihydrobenzo[b][1,4]dioxin-6-yl)-2-oxohexahydro-2H-pyrido[4,3-e][1,3]oxazine-7(3H)-carboxylate A vial was charged with $K_2CO_3$ (0.22 g, 1.56 mmol, 2 eq.), CuI (0.01 g, 0.08 mmol, 0.1 eq.) and trans-1,2-cyclohexane diamine (0.01 g, 0.08 mmol, 0.1 eq.), rac-(4aR*,8aR*)-tert-butyl 2-oxohexahydro-2H-pyrido[4,3-e][1,3]oxazine-7(3H)-carboxylate (Preparation A, 0.2 g, 0.78 mmol) and flushed with nitrogen for 5 min. A solution of 6-iodo-2,3-dihydrobenzo[b][1,4]dioxine (0.21 g, 0.78 mmol, 1.01 eq.) in dry dioxane (0.78 mL) was added and the resulting suspension was at 110° C. for 40 h. The reaction mixture was cooled to rt and filtered over Celite. The solid was washed by EA (2×10 mL). The filtrate was concentrated to dryness and the residue was purified by CC (DCM/MeOH 49:1 to 19:1) to give the title compound as a beige foam (0.19 g).
MS (ESI, m/z): 391.2 [M+H$^+$] for $C_2H_{26}N_2O_6$.

B.ii. Rac-(4aR*,8aR*)-3-(2,3-dihydrobenzo[b][1,4]dioxin-6-yl)octahydro-2H-pyrido[4,3-e][1,3]oxazin-2-one A solution of intermediate B.i (0.18 g, 0.47 mmol) in TFA (1.8 mL) was stirred at rt for 20 min. The volatiles were removed in vacuo and the residue was partitioned between aq. sat. sodium carbonate (5 mL) and DCM/MeOH (9:1, 8 mL). The aq. layer (pH=11) was extracted four times with DCM/MeOH (9:1, 4×10 mL). The combined org. layers were dried over $Na_2SO_4$, filtered and concentrated. The residue was purified by CC (DCM/MeOH 19:1 containing 1% aq. $NH_4OH$) to give the title amine as a white foam (0.07 g).
$^1$H NMR (d6-DMSO) δ: 6.84 (d, J=2.3 Hz, 1H); 6.81 (d, J=8.4 Hz, 1H); 6.76 (dd, J=2.3, 8.4 Hz, 1H); 4.21 (s, 4H); 3.96 (td, J=4.7, 10.2 Hz, 1H); 3.43 (dd, J=5.4, 11.0 Hz, 1H); 3.35 (t, J=11.0 Hz, 1H); 3.11 (dd, J=4.7, 11.4 Hz, 1H); 2.87 (m, 1H); 2.31-2.44 (m, 2H); 1.88 (m, 1H); 1.68 (m, 1H); 1.12 (m, 1H). MS (ESI, m/z): 291.2 [M+H$^+$] for $C_{15}H_{18}N_2O_4$.

Preparation C: rac-(4aR*,8aR*)-3-(3-oxo-3,4-dihydro-2H-benzo[b][1,4]oxazin-6-yl)octahydro-2H-pyrido[4,3-e][1,3]oxazin-2-one C.i. Rac-(4aR*,8aR*)-tert-butyl 3-(4-(4-methoxybenzyl)-3-oxo-3,4-dihydro-2H-benzo[b][1,4]oxazin-6-yl)-2-oxohexahydro-2H-pyrido[4,3-e][1,3]oxazine-7(3H)-carboxylate In a 7 mL sealed vial were introduced 6-iodo-4-(4-methoxybenzyl)-2H-benzo[b][1,4]thiazin-3(4H)-one (0.2 g, 0.486 mmol), rac-(4aR*,8aR*)-tert-butyl 2-oxohexahydro-2H-pyrido[4,3-e][1,3]oxazine-7(3H)-carboxylate (Preparation A, 0.15 g, 0.584 mmol, 1.2 eq.), potassium carbonate (0.134 g, 2 eq.), (R,R)-(−)-N,N'-dimethyl-1,2-cyclohexanediamine (0.01 g, 0.06 mmol, 0.1 eq.), CuI (0.11 g, 0.57 mmol, 1 eq.) and dioxane (2.3 mL). The suspension was stirred at 100° C. for 2 days. The mixture was cooled to rt, diluted with DCM/MeOH (9:1, 2 mL) and filtered. The yellow salt obtained was washed with DCM/MeOH (9:1, 2×10 mL). The combined filtrates were concentrated under reduced pressure. The residue was purified (DCM/MeOH 9:1) to afford the title compound as a greenish foam (0.15 g).
MS (ESI, m/z): 524.2 [M+H$^+$] for $C_{28}H_{33}N_3O_7$.

C.ii. rac-(4aR*,8aR*)-3-(3-oxo-3,4-dihydro-2H-benzo[b][1,4]oxazin-6-yl)octahydro-2H-pyrido[4,3-e][1,3]oxazin-2-one A solution of intermediate C.i (0.14 g, 0.26 mmol) in TFA (99%, 1.06 mL) was stirred at 60° C. for 1 h, then 3 h at 70° C. More TFA (1.06 mL) was added and the mixture was stirred at 80° C. overnight. The volatiles were removed in vacuo and the residue was partitioned between aq. sat. sodium carbonate (4 mL) and DCM/MeOH (9:1, 8 mL). The pH of the aq. layer was adjusted to 12 using 32% aq. NaOH and the aq. layer was extracted with DCM/MeOH (9:1, 4×10 mL). The combined org. layers were dried over $Na_2SO_4$, filtered and concentrated to dryness. The residue was purified by CC (DCM/MeOH 19:1 containing 0.5% aq. $NH_4OH$) to give the title compound as a beige foam (0.041 g, 49% yield).
$^1$H NMR (d6-DMSO) δ: 10.7 (s, 1H); 6.84-6.94 (m, 3H); 4.54 (s, 2H); 4.01 (td, J=4.3, 10.2 Hz, 1H); 3.33-3.49 (m, 2H); 3.35 (t, J=11.0 Hz, 1H); 3.12 (dd, J=4.7, 11.4 Hz, 1H); 2.87 (m, 1H); 2.31-2.44 (m, 2H); 1.89 (m, 1H); 1.68 (m, 1H); 1.12 (m, 1H). MS (ESI, m/z): 304.2 [M+H$^+$] for $C_{15}H_{17}N_3O_4$.

Preparation D: rac-(4aR*,8aR*)-3-(4-(4-methoxybenzyl)-3-oxo-3,4-dihydro-2H-benzo[b][1,4]thiazin-6-yl)octahydro-2H-pyrido[4,3-e][1,3]oxazin-2-one D.i. Rac-(4aR*,8aR*)-tert-butyl 3-(4-(4-methoxybenzyl)-3-oxo-3,4-dihydro-2H-benzo[b][1,4]thiazin-6-yl)-2-oxohexahydro-2H-pyrido[4,3-e][1,3]oxazine-7(3H)-carboxylate In a 7 mL sealed vial were introduced 6-iodo-4-(4-methoxybenzyl)-2H-benzo[b][1,4]oxazin-3(4H)-one (0.2 g, 0.57 mmol), rac-(4aR*,8aR*)-tert-butyl 2-oxohexahydro-2H-pyrido[4,3-e][1,3]oxazine-7(3H)-carboxylate (Preparation A, 0.18 g, 0.69 mmol, 1.2 eq.), potassium carbonate (0.16 g, 1.15 mmol, 2 eq.), (R,R)-(−)-N,N'-dimethyl-1,2-cyclohexanediamine (0.008 mL, 0.1 eq.), CuI (0.09 g, 0.1 eq.) and dioxane (2 mL). The suspension was stirred at 100° C. for 2 days. The mixture was cooled to rt, diluted with DCM/MeOH (2 mL) and filtered. The yellow salt obtained was washed with DCM/MeOH (9:1, 2×10 mL). The combined filtrates were concentrated under reduced pressure. The residue was purified by CC (DCM/MeOH 9:1) to afford the title compound as a greenish foam (0.231 g).
MS (ESI, m/z): 540.0 [M+H$^+$] for $C_{28}H_{33}N_3O_6S$.

D.ii. Rac-(4aR*,8aR*)-3-(3-oxo-3,4-dihydro-2H-benzo[b][1,4]oxazin-6-yl)octahydro-2H-pyrido[4,3-e][1,3]oxazin-2-one A solution of intermediate D.i (0.2 g, 0.38 mmol) in TFA (1.5 mL) was stirred at rt for 10 min. The volatiles were removed in vacuo and the residue was partitioned between aq. sat. sodium carbonate (4 mL) and DCM/MeOH (9:1, 8 mL). The pH of the aq. layer was adjusted to 12 adding 32% NaOH, and then extracted with DCM/MeOH (9:1, 4×10 mL). The combined org. layers were dried over $MgSO_4$, filtered and concentrated to dryness. The residue was purified by CC (DCM/MeOH 9:1 containing 10% of aq. $NH_4OH$) to give the title compound as a yellow foam (0.134 g, 80% yield).
$^1$H NMR (d6-DMSO) δ: 7.38 (d, J=8.3 Hz, 1H); 7.33 (d, J=2.0 Hz, 1H); 7.16 (d, J=8.6 Hz, 2H); 7.01 (dd, J=2.0, 8.3 Hz, 1H); 6.84 (d, J=8.6 Hz, 2H); 5.15 (br. s, 2H); 4.01 (td, J=4.6, 10.2 Hz, 1H); 3.70 (s, 3H); 3.63 (s, 2H); 3.37 (m, 1H); 3.35 (d, J=3.5 Hz, 1H); 3.13 (dd, J=4.7, 11.5 Hz, 1H); 2.90 (m, 1H); 2.33-2.50 (m, 2H); 1.90 (m, 1H); 1.70 (m, 1H); 1.17 (m, 1H). MS (ESI, m/z): 440.0 [M+H$^+$] for $C_{23}H_{25}N_3O_4S$.

Preparation E: (R)-7-fluoro-2-methoxy-8-(oxiran-2-yl)-1,5-naphthyridine and (S)-7-fluoro-2-methoxy-8-(oxiran-2-yl)-1,5-naphthyridine The two title enantiomers of 7-fluoro-2-methoxy-8-(oxiran-2-yl)-1,5-naphthyridine were separated by chiral HPLC. Rac-7-fluoro-2-methoxy-8-(oxiran-2-yl)-1,5-naphthyridine obtained as described in WO 2004/058144 (0.33 g), was separated using the following chiral HPLC conditions: ChiralPak IC (Daicel, 30×250 mm, 5 µm) column, using a ratio of 1/1 of eluent A (EtOH, in the presence of 0.1% diethylamine) and eluent B (MeCN), at rt, at a flow rate of 34 mL/min. The relevant fractions were pooled and concentrated to afford each enantiomer (0.15 g). The absolute stereochemistry of both enantiomers was assigned by comparison with the chiral HPLC analysis of an authentic sample of the (R)-enantiomer synthesized as described in WO 2007/016610.

(R)-enantiomer: $t_R$=8.5 min (ChiralPak IA (Daicel, 4.6×250 mm, 5 µm), same gradient as before at a flow rate of 0.8 mL/min). MS (ESI, m/z): 221.2 [M+H$^+$] for $C_{11}H_9N_2O_2F$.

(S)-enantiomer: $t_R$=11.0 min (ChiralPak IA (Daicel, 4.6×250 mm, 5 µm), same gradient as before at a flow rate of 0.8 mL/min). MS (ESI, m/z): 221.2 [M+H$^+$] for $C_{11}H_9N_2O_2F$.

Preparation F:
rac-7-fluoro-2-methoxy-8-(oxiran-2-yl)quinoline

F.i. 7-fluoro-2-methoxy-8-vinylquinoline

A solution of 8-bromo-7-fluoro-2-methoxyquinoline and (PPh$_3$)$_4$Pd in DME (155 mL) was flushed with N$_2$. K$_2$CO$_3$ (2.66 g, 19.3 mmol), water (47 mL) and 2,4,6-trivinylcyclotriboroxane-pyridine (2.31 g) were added at rt and the mixture was heated at 85° C. overnight. After cooling to rt, water (50 mL) was added and the mixture was extracted with TBME (2×100 mL). The combined org. layers were washed with water (30 mL) and brine (30 mL), dried over MgSO$_4$ and concentrated to dryness. The residue was purified by CC (Hept/EA 4:1) to afford the title alkene as an orange solid (3.97 g, quant. yield).

MS (ESI, m/z): 204.2 [M+H$^+$] for $C_{12}H_{10}NOF$.

F.ii. Rac-1-(7-fluoro-2-methoxyquinolin-8-yl)ethane-1,2-diol

To a solution of intermediate F.i (1.88 g, 9.25 mmol) in DCM (40 mL) and water (5 mL) were added NMO (137 mg, 10.2 mmol) and potassium osmate (VI) dihydrate (0.035 g, 0.1 mmol). The resulting mixture was vigorously stirred at rt for 2 h. The phases were separated, the aq. layer was extracted with a DCM/MeOH mixture (9:1, 100 mL) and the combined org. layers were washed with 10% Na$_2$S$_2$O$_3$, dried over MgSO$_4$ and concentrated to dryness. The residue was purified by CC (Hept/EA 1:1 then EA) to afford the title diol as a yellowish oil (1.85 g, 85% yield).

MS (ESI, m/z): 238.0 [M+H$^+$] for $C_{12}H_{12}NO_3F$.

F.iii.
Rac-7-fluoro-2-methoxy-8-(oxiran-2-yl)quinoline

To an ice-chilled solution of intermediate F.ii (1.18 g, 4.97 mmol) and trimethyl orthoacetate (0.75 mL, 5.92 mmol) in DCM (45 mL) was added TMSCl (0.763 mL, 5.97 mmol). The mixture was stirred 10 min. and was concentrated under reduced pressure. The residue was taken up in MeOH (30 mL) and K$_2$CO$_3$ (1.72 g, 12.4 mmol) was added. The suspension was vigorously stirred at rt for 1 h. Water (50 mL) and DCM (300 mL) were added and the two phases were separated. The aq. layer was extracted once more with DCM (100 mL). The combined org. layers were dried over MgSO$_4$, filtered and concentrated to dryness to afford the title epoxide as a yellowish oil (0.98 g, 90% yield).

$^1$H NMR (d6-DMSO) δ: 7.95 (d, J=9.5 Hz, 1H); 7.66 (dd, J=5.8, 8.9 Hz, 1H); 7.12 (dd, J=8.9, 10.4 Hz, 1H); 6.89 (d, J=8.8 Hz, 1H); 4.74 (dd, J=2.9, 4.2 Hz, 1H); 4.08 (s, 3H); 3.59 (ddd, J=0.7, 2.9, 5.5 Hz, 1H); 3.28 (ddd, J=2.9, 5.5, 8.4 Hz, 1H). MS (ESI, m/z): 219.9 [M+H$^+$] for $C_{12}H_{10}NO_2F$.

Preparation G:
rac-7-fluoro-2-methoxy-8-(oxiran-2-yl)quinoxaline

G.i. 7-fluoro-2-methoxy-8-vinylquinoxaline

Methyl triphenyl phosphonium bromide (154 g, 430 mmol) was suspended in THF (1 L) and cooled to 0° C. KOtBu (44.4 g, 400 mmol) was added in one portion and the yellow suspension was stirred at 0° C. for 15 min before a solution of 6-fluoro-3-methoxyquinoxaline-5-carbaldehyde (71 g, 340 mmol) in THF (550 mL) was added dropwise over 70 min. The mixture was stirred at 0° C. for 60 min. Sat. NH$_4$Cl solution (250 mL) and water (250 mL) were added and the phases were separated. The org. layer was dried over MgSO$_4$, filtered and concentrated to dryness. The residue was purified by two filtrations over a plug of silica gel (2×250 g) using an Hept/EA (2:1) mixture as eluent to afford the title alkene as an orange solid (62.7 g, 89% yield).

$^1$H NMR (CDCl$_3$) δ: 8.43 (s, 1H), 7.88 (dd, J=5.6, 9.1 Hz, 1H), 7.49 (dd, J=12.1, 18.2 Hz, 1H), 6.38 (dd, J=1.3, 18.2 Hz, 1H), 5.73 (dt, J=1.8, 12.1 Hz, 1H), 4.12 (s, 3H).

G.ii.
Rac-7-fluoro-2-methoxy-8-(oxiran-2-yl)quinoxaline

Starting from intermediate G.i (60.2 g, 295 mmol), the title epoxide was obtained as a colourless solid (39.8 g) using the procedures described in Preparation F, steps F.ii and F.iii (dihydroxylation: 84% yield, epoxide formation: 86% yield).

$^1$H NMR (CDCl$_3$) δ: 8.45 (s, 1H), 7.97 (dd, J=5.5, 9.1 Hz, 1H), 7.30 (dd, J=9.4, 10.1 Hz, 1H) 4.66 (dd, J=2.9, 4.2 Hz, 1H), 4.12 (s, 3H); 3.59 (ddd, J=0.5, 2.9, 5.5 Hz, 1H), 3.28 (m, 1H).

Preparation H: rac-(4aR*,8aR*)-3-(4-(4-methoxybenzyl)-3-oxo-3,4-dihydro-2H-pyrido[3,2-b][1,4]oxazin-6-yl)octahydro-2H-pyrido[4,3-e][1,3]oxazin-2-one Starting from 6-bromo-4-(4-methoxybenzyl)-2H-pyrido [3,2-b][1,4]oxazin-3(4H)-one (prepared as described in WO 2010/041194, 0.35 g, 1 mmol) and rac-(4aR*,8aR*)-tert-butyl 2-oxohexahydro-2H-pyrido[4,3-e][1,3]oxazine-7(3H)-carboxylate (Preparation A, 0.308 g, 1.2 mmol, 1.2 eq.), the title compound was obtained as an orange foam (0.255 g) using the procedures described in Preparation D, steps D.i and D.ii (Buchwald coupling: 95% yield, Boc deprotection: 63% yield).

MS (ESI, m/z): 425.0 [M+H$^+$] for $C_{22}H_{24}N_4O_5$.

Preparation I: rac-(4aS*,8aS*)-3-(4-(4-methoxybenzyl)-3-oxo-3,4-dihydro-2H-pyrido[3,2-b][1,4]thiazin-6-yl)octahydro-2H-pyrido[4,3-e][1,3]oxazin-2-one

I.i. 6-chloro-4-(4-methoxybenzyl)-2H-pyrido[3,2-b][1,4]thiazin-3 (4H)-one

A suspension of 6-chloro-2H-pyrido[3,2-b][1,4]thiazin-3 (4H)-one (prepared as described in WO 2010/041194, 0.8 g, 3.99 mmol), $Cs_2CO_3$ (1.56 g, 4.78 mmol) and PMB-Cl (0.61 mL, 4.39 mmol) in DMF (8 mL) was stirred at rt for 4 h. The solvent was evaporated to dryness and the residue was partitioned between EA (20 mL) and water (25 mL). The aq. layer was extracted once with EA (15 mL) and the combined org. layers were washed with brine (20 mL), dried over $Na_2SO_4$ and concentrated to dryness. The residue (1.39 g) was crystallized in a mixture of ether/Hept (2:3). After filtration, the title compound was obtained as an orange solid (1.2 g, 93% yield).

$^1$H NMR (d6-DMSO) δ: 7.88 (d, J=8.0 Hz, 1H), 7.13-7.20 (m, 3H); 6.79-6.85 (m, 2H); 5.16 (s, 2H), 3.71 (s, 2H); 3.67 (s, 3H). MS (ESI, m/z): 321.1 [M+H$^+$] for $C_{15}H_{13}N_2O_2ClS$.

I.ii. Rac-(4aS*,8aS*)-3-(4-(4-methoxybenzyl)-3-oxo-3,4-dihydro-2H-pyrido[3,2-b][1,4]thiazin-6-yl)octahydro-2H-pyrido[4,3-e][1,3]oxazin-2-one Starting from intermediate I.i (171 mg, 0.53 mmol), the title compound, was obtained as a yellowish foam (0.132 g) using the procedures described in Preparation D, steps D.i and D.ii (Buchwald coupling: 73% yield, Boc deprotection: 79% yield).

$^1$H NMR (d6-DMSO) δ: 7.79 (d, J=8.5 Hz, 1H); 7.51 (d, J=8.5 Hz, 1H); 7.09-7.14 (m, 2H); 6.78-6.83 (m, 2H); 5.19 (s, 2H); 3.94 (td, J=4.8, 10.2 Hz, 1H); 3.75 (overlapped dd, J=5.3, 11.9 Hz, 1H); 3.72 (s, 2H); 3.67 (s, 3H); 3.08-3.16 (m, 2H); 2.88 (m, 1H); 2.28-2.44 (m, 3H); 1.65-1.86 (m, 2H); 1.16 (m, 1H). MS (ESI, m/z): 441.2 [M+H$^+$] for $C_{22}H_{24}N_4O_4S$.

Preparation J: rac-(4aR*,8aR*)-3-(2,3-dihydro-[1,4]dioxino[2,3-b]pyridin-7-yl)octahydro-2H-pyrido[4,3-e][1,3]oxazin-2-one Starting from commercial 7-bromo-2,3-dihydro-[1,4]dioxino[2,3-b]pyridine (81 mg, 0.37 mmol), the title compound was obtained as a beige foam (73 mg) using the procedures described in Preparation D, steps D.i and D.ii (Buchwald coupling: 67% yield, Boc deprotection: 100% yield).

$^1$H NMR (d6-DMSO) δ: 7.74 (d, J=2.3 Hz, 1H), 7.35 (d, J=2.3 Hz, 1H); 4.36-4.40 (m, 2H); 4.21-4.26 (m, 2H); 4.02 (td, J=4.7, 10.3 Hz, 1H); 3.36-3.50 (m, 2H); 3.13 (dd, J=4.8, 11.6 Hz, 1H), 2.89 (m, 1H); 2.75 (br. s, 1H); 2.36-2.47 (m, 2H); 1.94 (m, 1H); 1.70 (m, 1H); 1.16 (m, 1H). MS (ESI, m/z): 291.9 [M+H$^+$] for $C_{14}H_{17}N_3O_4$.

Preparation K: rac-(4aS*,8aS*)-3-(6,7-dihydro-[1,4]dioxino[2,3-c]pyridazin-3-yl)octahydro-2H-pyrido[4,3-e][1,3]oxazin-2-one Starting from 3-bromo-6,7-dihydro-[1,4]dioxino[2,3-c]pyridazine (180 mg, 1.04 mmol), the title compound was obtained as a white solid (33 mg) using the procedures described in Preparation D, steps D.i and D.ii (Buchwald coupling: 18% yield, Boc deprotection: 62% yield).

$^1$H NMR (d6-DMSO) δ: 7.44 (s, 1H); 4.47-4.52 (m, 2H); 4.35-4.41 (m, 2H); 3.98-4.09 (m, 2H); 3.45 (t, J=11.7 Hz, 1H); 3.13 (dd, J=4.8, 11.6 Hz, 1H), 2.89 (m, 1H); 2.42-2.47 (m, 2H); 1.90 (m, 1H); 1.76 (m, 1H); 1.20 (m, 1H). MS (ESI, m/z): 293.3 [M+H$^+$] for $C_{13}H_{16}N_4O_4$.

Preparation L: rac-(4aR*,8aR*)-3-(2,3-dihydro-[1,4]dioxino[2,3-c]pyridin-7-yl)octahydro-2H-pyrido[4,3-e][1,3]oxazin-2-one

L.i. Rac-(3R*,4R*)-tert-butyl 4-(((2,3-dihydro-[1,4]dioxino[2,3-c]pyridin-7-yl)amino)methyl)-3-hydroxypiperidine-1-carboxylate A mixture of rac-(3R*,4R*)-tert-butyl 3-hydroxy-4-((tosyloxy)methyl)piperidine-1-carboxylate (prepared as described in *Tetrahedron* (2008), 64, 2456-2464, 0.26 g, 0.67 mmol) and tert-butyl (2,3-dihydro-[1,4]dioxino[2,3-c]pyridin-7-yl)carbamate (prepared as described in WO 2009/104159, 0.17 g, 0.67 mmol, 1 eq.) was dissolved in DMF (2.5 mL). NaH (60% dispersion in oil, 0.04 g, 0.88 mmol, 1.3 eq.) was added and the mixture was vigorously stirred at rt for 2 h. More NaH (0.03 g, 0.67 mmol, 1 eq.) was added. After two more hours, sat. aq. $NaHCO_3$ (5 mL) was added and the mixture was extracted with EA (3×10 mL). The combined org. phases were dried over $MgSO_4$ and concentrated under reduced pressure. The residue was purified by CC (DCM/MeOH 19:1) to afford the title compound as a white solid (0.15 g, 62% yield).

MS (ESI, m/z): 366.4 [M+H$^+$] for $C_{18}H_{27}N_3O_5$.

L.ii. Rac-(4aR*,8aR*)-tert-butyl 3-(2,3-dihydro-[1,4]dioxino[2,3-c]pyridin-7-yl)-2-oxohexahydro-2H-pyrido[4,3-e][1,3]oxazine-7(3H)-carboxylate To a suspension of intermediate L.i (0.15 g, 0.4 mmol) in DCM (3 mL) was added TEA (0.12 mL, 0.87 mmol, 2.2 eq.). The mixture was cooled to −78° C. and a solution of triphosgene (0.06 g, 0.21 mmol, 0.54 eq.) in DCM (0.8 mL) was added dropwise. The solution was stirred at this temperature for 1 h. Water (6 mL) and DCM (10 mL) were added. The aq. layer was extracted once with DCM (10 mL). The combined org. layers were washed with brine, dried over $MgSO_4$, filtered and concentrated down. The crude product was purified by CC (DCM/MeOH 19:1) to afford the title product as a white foam (0.12 g, 78% yield).

MS (ESI, m/z): 392.3 [M+H$^+$] for $C_{19}H_{25}N_3O_6$.

L.iii. Rac-(4aR*,8aR*)-3-(2,3-dihydro-[1,4]dioxino[2,3-c]pyridin-7-yl)octahydro-2H-pyrido[4,3-e][1,3]oxazin-2-one A solution of intermediate L.ii (0.12 g, 0.3 mmol) in 4N HCl in dioxane (3.3 mL) was stirred at rt for 2 h. The mixture was concentrated to dryness. The residue was partitioned between sat. aq. $NaHCO_3$ (6 mL) and DCM/MeOH (9:1, 30 mL). The aq. layer was extracted with the same mixture twice more (2×15 mL). The combined org. layers were washed with brine (8 mL), dried over $MgSO_4$, filtered and concentrated to dryness. The residue was purified by CC (DCM/MeOH 19:1+0.5% aq. $NH_4OH$) to afford the title compound as a beige solid (0.06 g, 73% yield).

$^1$H NMR (d6-DMSO) δ: 7.92 (s, 1H); 7.19 (s, 1H); 4.31-4.35 (m, 2H); 4.24-4.29 (m, 2H); 3.87-4.01 (m, 2H); 3.31 (overlapped t, J=11.5 Hz, 1H); 3.13 (dd, J=4.6, 11.5 Hz, 1H), 2.87 (m, 1H); 2.34-2.47 (m, 2H); 1.71-1.91 (m, 2H); 1.18 (m, 1H). MS (ESI, m/z): 292.3 [M+H$^+$] for $C_{14}H_{17}N_3O_4$.

Preparation M: rac-(4aR*,8aR*)-3-(6,7-dihydro-[1,4]oxathiino[2,3-c]pyridazin-3-yl)octahydro-2H-pyrido[4,3-e][1,3]oxazin-2-one Starting from 3-chloro-6,7-dihydro-[1,4]oxathiino[2,3-c]pyridazine (prepared as described in WO 2007/071936, 200 mg, 1.06 mmol), the title compound was obtained as a beige solid (76 mg) using the procedures described in Preparation D, step D.i (Buchwald coupling: 70% yield), and Preparation L, step L.ii (Boc deprotection: 32% yield). The residue was purified by CC (DCM/MeOH 19:1+0.5% aq. NH$_4$OH).

$^1$H NMR (d6-DMSO) δ: 7.80 (s, 1H); 4.55-4.60 (m, 2H); 3.97-4.08 (m, 2H); 3.44 (t, J=11.6 Hz, 1H); 3.26-3.31 (m, 2H); 3.14 (dd, J=4.6, 11.4 Hz, 1H); 2.89 (m, 1H); 2.36-2.50 (m, 2H); 2.34 (br. s, 1H); 1.90 (m, 1H); 1.76 (m, 1H); 1.20 (m, 1H).

MS (ESI, m/z): 309.0 [M+H$^+$] for $C_{13}H_{16}N_4O_3S$.

Examples 1 and 2

(4aR,8aR)-3-(2,3-dihydro-benzo[1,4]dioxin-6-yl)-7-[2-(3-fluoro-6-methoxy-[1,5]naphthyridin-4-yl)-ethyl]-octahydro-pyrido[4,3-e][1,3]oxazin-2-one and (4aS,8aS)-3-(2,3-dihydro-benzo[1,4]dioxin-6-yl)-7-[2-(3-fluoro-6-methoxy-[1,5]naphthyridin-4-yl)-ethyl]-octahydro-pyrido[4,3-e][1,3]oxazin-2-one 1/2.i. Rac-(4aR*,8aR*)-3-(2,3-dihydro-benzo[1,4]dioxin-6-yl)-7-[2-(3-fluoro-6-methoxy-[1,5]naphthyridin-4-yl)-ethyl]-octahydro-pyrido[4,3-e][1,3]oxazin-2-one Typical Procedure for the Addition of the Oxazinone Moiety onto an Alkene To a solution of 7-fluoro-2-methoxy-8-vinyl-1,5-naphthyridine (0.062 g, 0.3 mmol) and intermediate B.ii (0.09 g, 0.3 mmol) in DMF (0.26 mL) was added one drop of TMG. The mixture was stirred at 90° C. for 24 h. The mixture was cooled to rt and concentrated to dryness. The residue was purified by CC (DCM/MeOH 97:3+0.3% aq. NH$_4$OH to 19:1+0.5% aq. NH$_4$OH) to afford the desired compound as a yellowish foam (0.06 g, 40% yield).

$^1$H NMR (d6-DMSO) δ: 8.76 (d, J=0.4 Hz, 1H); 8.27 (d, J=9.1 Hz, 1H); 7.23 (d, J=9.1 Hz, 1H); 6.83 (d, J=2.3 Hz, 1H); 6.81 (d, J=8.4 Hz, 1H); 6.74 (dd, J=2.3, 8.4 Hz, 1H); 4.20 (s, 4H); 4.04 (s, 3H); 4.02 (overlapped m, 1H); 3.25-3.45 (m, 5H); 2.96 (m, 1H); 2.76-2.84 (m, 2H); 2.05-2.20 (m, 2H); 1.68-1.88 (m, 2H); 1.20 (m, 1H). MS (ESI, m/z): 495.4 [M+H$^+$] for $C_{26}H_{27}N_4O_5F$.

1/2.ii. (4aR,8aR)-3-(2,3-dihydro-benzo[1,4]dioxin-6-yl)-7-[2-(3-fluoro-6-methoxy-[1,5]naphthyridin-4-yl)-ethyl]-octahydro-pyrido[4,3-e][1,3]oxazin-2-one and (4aS,8aS)-3-(2,3-dihydro-benzo[1,4]dioxin-6-yl)-7-[2-(3-fluoro-6-methoxy-[1,5]naphthyridin-4-yl)-ethyl]-octahydro-pyrido[4,3-e][1,3]oxazin-2-one Compounds 1/2.i (0.06 g), were separated using the following chiral HPLC conditions: ChiralPak IA (Daicel, 30×250 mm, 5 μm) column, using a ratio of 41 of eluent A (EtOH, in the presence of 0.1% diethylamine) and eluent B (MeCN), at rt, at a flow rate of 0.8 mL/min. The relevant fractions were pooled and concentrated to afford each enantiomer (0.02 g).

Enantiomer 1: t$_R$=10.56 min (ChiralPak IA (Daicel, 4.6× 250 mm, 5 μm), same gradient as before). $^1$H NMR (d6-DMSO) δ: 8.76 (d, J=0.4 Hz, 1H); 8.27 (d, J=9.1 Hz, 1H); 7.23 (d, J=9.1 Hz, 1H); 6.83 (d, J=2.3 Hz, 1H); 6.81 (d, J=8.4 Hz, 1H); 6.74 (dd, J=2.3, 8.4 Hz, 1H); 4.20 (s, 4H); 4.04 (s, 3H); 4.02 (overlapped m, 1H); 3.25-3.45 (m, 5H); 2.96 (m, 1H); 2.76-2.84 (m, 2H); 2.05-2.20 (m, 2H); 1.68-1.88 (m, 2H); 1.20 (m, 1H).

MS (ESI, m/z): 495.2 [M+H$^+$] for $C_{26}H_{27}N_4O_5F$.

Enantiomer 2: t$_R$=12.55 min (ChiralPak IA (Daicel, 4.6× 250 mm, 5 μm), same gradient as before). MS (ESI, m/z): 495.2 [M+H$^+$] for $C_{26}H_{27}N_4O_5F$.

Example 3

(4aR*,8aR*)-3-(2,3-dihydro-benzo[1,4]dioxin-6-yl)-7-[(2RS)-2-hydroxy-2-(6-methoxy-[1,5]naphthyridin-4-yl)-ethyl]-octahydro-pyrido[4,3-e][1,3]oxazin-2-one (mixture of stereoisomers)

Typical Procedure for an Epoxide Opening with an Oxazinone Moiety

To a solution of intermediate B.ii (0.03 g, 0.11 mmol) and rac-2-methoxy-8-(oxiran-2-yl)-1,5-naphthyridine (0.02 g, 0.11 mmol, 1.05 eq.) in DMF (0.38 mL) were added K$_2$CO$_3$ (0.02 g, 0.15 mmol, 1.4 eq.) and lithium perchlorate (0.01 g, 0.11 mmol, 1.05 eq.). The reaction mixture was stirred at 80° C. for 18 h. The mixture was cooled to rt and filtered over Celite. The solid was washed by EA (2×15 mL). The filtrate was concentrated. The residue was purified by CC (DCM/MeOH 97:3+0.3% aq. NH$_4$OH) to afford the title compound as an off-white foam (0.037 g, 71% yield).

$^1$H NMR (d6-DMSO) δ: 8.77 (d, J=4.5 Hz, 1H); 8.25 (d, J=9.1 Hz, 1H); 7.76 (d, J=4.5 Hz, 1H); 7.25 (d, J=9.1 Hz, 1H); 6.80-6.85 (m, 2H); 6.76 (m, 1H); 5.81 (m, 1H); 5.33 (dd, J=2.4, 4.5 Hz, 1H); 4.21 (s, 4H); 4.07 (m, 1H); 4.01 (s, 3H); 3.34-3.48 (m, 2H); 3.24 (m, 1H); 3.12 (m, 1H); 2.81-2.95 (m, 1H); 2.61 (m, 1H); 2.15-2.32 (m, 2H); 1.68-1.89 (m, 2H); 1.25 (m, 1H). MS (ESI, m/z): 493.2 [M+H$^+$] for $C_{26}H_{28}N_4O_6$.

Example 4 rac-(4aR*,8aR*)-3-(2,3-dihydro-benzo[1,4]dioxin-6-yl)-7-[2-(6-methoxy-[1,5]naphthyridin-4-yl)-ethyl]-octahydro-pyrido[4,3-e][1,3]oxazin-2-one Starting from 2-methoxy-8-vinyl-1,5-naphthyridine (0.0215 g, 0.115 mmol) and intermediate B.ii. (0.0335 g, 0.115 mmol), the title compound was obtained as an off-white foam (0.017 g, 31% yield) using the procedure described in Examples 1 and 2, step 1/2.i. The crude material was purified by CC (DCM/MeOH 19:1+0.5% aq. NH$_4$OH).

$^1$H NMR (d6-DMSO) δ: 8.66 (d, J=4.4 Hz, 1H); 8.23 (d, J=9.0 Hz, 1H); 7.59 (d, J=4.4 Hz, 1H); 7.24 (d, J=9.1 Hz, 1H); 6.73-6.83 (m, 3H); 4.21 (s, 4H); 4.07 (m, 1H); 4.01 (s, 3H); 3.25-3.49 (m, 5H); 2.97 (m, 1H); 2.79-2.88 (m, 2H); 2.04-2.21 (m, 2H); 1.70-1.89 (m, 2H); 1.23 (m, 1H). MS (ESI, m/z): 477.2 [M+H$^+$] for $C_{26}H_{28}N_4O_5$.

Example 5 rac-(4aR*,8aR*)-7-[2-(3-fluoro-6-methoxy-[1,5]naphthyridin-4-yl)-ethyl]3-(3-oxo-3,4-dihydro-2H-benzo[1,4]oxazin-6-yl)-octahydro-pyrido[4,3-e][1,3]oxazin-2-one Starting from 7-fluoro-2-methoxy-8-vinyl-1,5-naphthyridine (25 mg, 0.122 mmol) and intermediate C.ii (37 mg, 0.122 mmol), the title compound was obtained as an off-white foam (54 mg, 9% yield) using the procedure described in Examples 1 and 2, step 1/2.i. The crude material was purified by CC (DCM/MeOH 97:3+0.3% aq. NH₄OH).

¹H NMR (d6-DMSO) δ: 10.76 (s, 1H); 8.80 (s, 1H); 8.30 (d, J=9.1 Hz, 1H); 7.26 (d, J=9.1 Hz, 1H); 6.85-6.96 (m, 3H); 4.57 (s, 2H); 4.10 (m, 1H); 4.07 (s, 3H); 3.29-3.50 (m, 5H); 2.99 (m, 1H); 2.80-2.87 (m, 2H); 2.19 (m, 1H); 2.12 (t, J=10.2 Hz, 1H); 1.86 (m, 1H); 1.76 (m, 1H); 1.25 (m, 1H). MS (ESI, m/z): 508.1 [M+H⁺] for $C_{26}H_{26}N_5O_5F$.

Example 6

(4aR*,8aR*)-3-(2,3-dihydro-benzo[1,4]dioxin-6-yl)-7-[(2RS)-2-(3-fluoro-6-methoxy-[1,5]naphthyridin-4-yl)-2-hydroxy-ethyl]-octahydro-pyrido[4,3-e][1,3]oxazin-2-one (mixture of stereoisomers)

Starting from rac-7-fluoro-2-methoxy-8-(oxiran-2-yl)-1,5-naphthyridine (0.025 g, 0.112 mmol) and intermediate B.ii. (0.031 g, 0.107 mmol), the title compound was obtained as a gum (containing still some residual DMF; 0.041 g, 76% yield) using the procedure described in Example 3. The crude material was purified by CC (DCM/MeOH 13:1+0.3% aq. NH₄OH).

¹H NMR (d6-DMSO) δ: 8.80 (app. d, J=1.3 Hz, 1H); 8.31 (app. dd, J=1.3, 9.1 Hz, 1H); 7.28 (app. d, J=3.1, 9.1 Hz, 1H); 6.73-6.84 (m, 3H); 6.03 (m, 1H); 5.56 (t, J=5.5 Hz, 1H); 4.22 (s, 4H); 4.07 (s, 1.5H); 4.05 (s, 1.5H); 3.95 (td, J=4.2, 9.5 Hz, 0.5H); 3.88 (td, J=4.2, 9.5 Hz, 0.5H); 3.29-3.46 (m, 3.5H); 3.16 (dd, J=4.4, 10.4 Hz, 0.5H); 3.00-3.10 (m, 2H); 2.96 (dd, J=6.2, 12.7 Hz, 0.5H); 2.86 (m, 0.5H); 2.07-2.27 (m, 2H); 1.64-1.85 (m, 2H); 1.10 (m, 1H). MS (ESI, m/z): 511.1 [M+H⁺] for $C_{26}H_{27}N_4O_6F$.

Example 7 rac-(4aR*,8aR*)-7-[2-(3-fluoro-6-methoxy-[1,5]naphthyridin-4-yl)-ethyl]-3-(3-oxo-3,4-dihydro-2H-benzo[1,4]thiazin-6-yl)-octahydro-pyrido[4,3-e][1,3]oxazin-2-one 7.i. Rac-(4aR*,8aR*)-7-(2-(3-fluoro-6-methoxy-1,5-naphthyridin-4-yl)ethyl)-3-(4-(4-methoxybenzyl)-3-oxo-3,4-dihydro-2H-benzo[b][1,4]thiazin-6-yl)octahydro-2H-pyrido[4,3-e][1,3]oxazin-2-one Starting from 7-fluoro-2-methoxy-8-vinyl-1,5-naphthyridine (0.033 g, 0.161 mmol) and intermediate D.ii (0.070 g, 0.161 mmol), the title compound was obtained as a beige foam (0.053 g, 52% yield) using the procedure described in Examples 1 and 2, step 1/2.i. The crude material was purified by CC (DCM/MeOH 19:1+0.5% aq. NH₄OH).

MS (ESI, m/z): 644.1 [M+H⁺] for $C_{34}H_{34}N_5O_5FS$.

7.ii. Rac-(4aR*,8aR*)-7-[2-(3-fluoro-6-methoxy-[1,5]naphthyridin-4-yl)-ethyl]-3-(3-oxo-3,4-dihydro-2H-benzo[1,4]thiazin-6-yl)-octahydro-pyrido[4,3-e][1,3]oxazin-2-one To a solution of intermediate 7.i (0.05 g, 0.1 mmol) in TFA (99%, 0.38 mL, 4.97 mmol, 50 eq.) was added concentrated HCl (0.003 mL). The reaction mixture was stirred at 80° C. for 2 h. The volatiles were removed in vacuo and the residue was partitioned between aq. sat. sodium carbonate (4 mL) and DCM/MeOH (9:1, 8 mL). The aq. layer (pH=12, adjusted using 8N NaOH) was extracted with DCM/MeOH (9:1, 2×10 mL). The combined org. layers were dried over Na₂SO₄, filtered and concentrated to dryness. The residue was purified by CC (DCM/MeOH 49:1+0.2% aq. NH₄OH to DCM/MeOH 97:3+0.3% aq.NH₄OH) to give the title compound as an off-white foam (0.038 g, 74% yield).

¹H NMR (d6-DMSO) δ: 10.57 (s, 1H); 8.76 (s, 1H); 8.27 (d, J=9.1 Hz, 1H); 7.30 (d, J=9.1 Hz, 1H); 7.24 (d, J=8.7 Hz, 1H); 6.91-6.98 (m, 2H); 4.09 (overlapped m, 1H); 4.05 (s, 3H); 3.44 (s, 2H); 3.28-3.54 (m, 5H); 2.97 (m, 1H); 2.77-2.85 (m, 2H); 2.06-2.23 (m, 2H); 1.70-1.89 (m, 2H); 1.23 (m, 1H). MS (ESI, m/z): 524.1 [M+H⁺] for $C_{26}H_{26}N_5O_4FS$.

Example 8 rac-(4aR*,8aR*)-3-(2,3-dihydro-benzo[1,4]dioxin-6-yl)-7-[2-(7-methoxy-2-oxo-2H-quinolin-1-yl)-ethyl]-octahydro-pyrido[4,3-e][1,3]oxazin-2-one To a solution of intermediate B.ii (0.048 g, 0.167 mmol) in DCE (1 mL) and THF (0.1 mL) was added 2-(7-methoxy-2-oxoquinolin-1(2H)-yl)acetaldehyde (prepared as described in WO 2008/009700, 0.038 g, 0.175 mmol, 1.05 eq.). The reaction mixture was stirred at rt for 2 h. NaBH(OAc)₃ (0.053 g, 0.25 mmol, 1.5 eq.) was added and the mixture was stirred at rt overnight. Further NaBH(OAc)₃ (0.035 g, 0.167 mmol, 1 eq.) was added and the mixture was stirred 2 more hours. Sat. aq. NaHCO₃ (10 mL) and DCM/MeOH (9:1, 25 mL) were added. The aq. layer was extracted with DCM/MeOH (9:1, 2×25 mL). The combined org. layers were washed with brine, dried over MgSO₄, filtered and concentrated to dryness. The crude product was purified via a preparative HPLC (Method A) to afford the title product as a white foam (0.042 g, 51% yield).

¹H NMR (d6-DMSO) δ: 7.80 (d, J=8.4 Hz, 1H); 7.63 (d, J=8.6 Hz, 1H); 6.96 (d, J=2.1 Hz, 1H); 6.74-6.90 (m, 4H); 6.40 (d, J=9.4 Hz, 1H); 4.29-4.49 (m, 2H), 4.22 (s, 4H); 4.07 (m, 1H); 3.89 (s, 3H); 3.31-3.49 (m, 3H); 2.99 (m, 1H), 2.62-2.71 (m, 2H); 2.04-2.20 (m, 2H); 1.70-1.89 (m, 2H); 1.25 (m, 1H). MS (ESI, m/z): 492.0 [M+H⁺] for $C_{27}H_{29}N_3O_6$.

Example 9 rac-(4aR*,8aR*)-3-(2,3-dihydro-benzo[1,4]dioxin-6-yl)-7-[2-(7-methoxy-2-oxo-2H-quinoxalin-1-yl)-ethyl]-octahydro-pyrido[4,3-e][1,3]oxazin-2-one Starting from 2-(7-methoxy-2-oxoquinoxalin-1(2H)-yl)acetaldehyde (0.04 g, 0.161 mmol) and intermediate B.ii (0.050 g, 0.172 mmol), the title compound was obtained as a yellowish foam (0.039 g, 46% yield) using the procedure described in Example 8. The crude material was purified by a preparative HPLC (Method A).

¹H NMR (d6-DMSO) δ: 8.03 (s, 1H); 7.74 (d, J=8.4 Hz, 1H); 6.95-7.04 (m, 2H); 6.73-6.85 (m, 3H); 4.28-4.48 (m, 2H), 4.21 (s, 4H); 4.01 (m, 1H); 3.91 (s, 3H); 3.30-3.48 (m, 3H); 2.93 (m, 1H); 2.66-2.75 (m, 2H); 2.01-2.19 (m, 2H); 1.68-1.89 (m, 2H); 1.19 (m, 1H).

MS (ESI, m/z): 493.0 [M+H⁺] for $C_{26}H_{28}N_4O_6$.

Example 10 rac-(4aR*,8aR*)-3-(2,3-dihydro-benzo[1,4]dioxin-6-yl)-7-[2-(7-methoxy-2-oxo-2H-[1,8]naphthyridin-1-yl)-ethyl]-octahydro-pyrido[4,3-e][1,3]oxazin-2-one Starting from 2-(7-methoxy-2-oxo-1,8-naphthyridin-1(2H)-yl)acetaldehyde (prepared as described in WO 2008/

009700, 0.04 g, 0.161 mmol) and intermediate B.ii (0.050 g, 0.172 mmol), the title compound was obtained as a yellowish foam (0.057 g, 67% yield) using the procedure described in Example 8. The crude material was purified by a preparative HPLC (Method A).

$^1$H NMR (d6-DMSO) δ: 8.0 (d, J=8.5 Hz, 1H); 7.85 (d, J=9.5 Hz, 1H); 6.70-6.84 (m, 4H); 6.49 (d, J=9.5 Hz, 1H); 4.43-4.60 (m, 2H), 4.21 (s, 4H); 4.03 (m, 1H); 3.98 (s, 3H); 3.30-3.49 (m, 3H); 2.98 (m, 1H); 2.69-2.80 (m, 2H); 2.05-2.20 (m, 2H), 1.68-1.89 (m, 2H); 1.19 (m, 1H). MS (ESI, m/z): 493.2 [M+H$^+$] for $C_{26}H_{28}N_4O_6$.

Example 11 rac-(4aR*,8aR*)-3-(2,3-dihydro-benzo[1,4]dioxin-6-yl)-7-[2-(6-methoxy-3-oxo-3H-pyrido[2,3-b]pyrazin-4-yl)-ethyl]-octahydro-pyrido[4,3-e][1,3]oxazin-2-one Starting from 2-(6-methoxy-3-oxopyrido[2,3-b]pyrazin-4 (3H)-yl)acetaldehyde (prepared as described in WO 2008/009700, 0.04 g, 0.161 mmol) and intermediate B.ii (0.050 g, 0.172 mmol), the title compound was obtained as a yellowish foam (0.053 g, 63% yield) using the procedure described in Example 8. The crude material was purified by a preparative HPLC (Method A).

$^1$H NMR (d6-DMSO) δ: 8.11-8.14 (m, 2H); 6.72-6.85 (m, 4H); 4.37-4.52 (m, 2H), 4.20 (s, 4H); 4.00 (m, 1H); 4.00 (s, 3H); 3.25-3.46 (m, 3H); 2.96 (m, 1H); 2.69-2.85 (m, 2H); 2.03-2.19 (m, 2H), 1.68-1.88 (m, 2H); 1.17 (m, 1H). MS (ESI, m/z): 494.2 [M+H$^+$] for $C_{25}H_{27}N_5O_6$.

Example 12 rac-(4aR*,8aR*)-3-(2,3-dihydro-benzo[1,4]dioxin-6-yl)-7-[2-(3-methoxy-6-oxo-6H-pyrido[2,3-b]pyrazin-5-yl)-ethyl]-octahydro-pyrido[4,3-e][1,3]oxazin-2-one Starting from 2-(3-methoxy-6-oxopyrido[2,3-b]pyrazin-5 (6H)-yl)acetaldehyde (prepared as described in WO 2008/009700, 0.04 g, 0.161 mmol) and intermediate B.ii (0.050 g, 0.172 mmol), the title compound was obtained as a yellowish foam (0.046 g, 54% yield) using the procedure described in Example 8. The crude material was purified by a preparative HPLC (Method A).

$^1$H NMR (d6-DMSO) δ: 8.23 (s, 1H), 7.93 (d, J=9.7 Hz, 1H); 6.68-6.83 (m, 4H); 4.37-4.53 (m, 2H), 4.20 (s, 4H); 4.05 (s, 3H); 3.99 (m, 1H); 3.26-3.48 (m, 3H); 2.96 (m, 1H); 2.69-2.81 (m, 2H); 2.03-2.19 (m, 2H); 1.67-1.90 (m, 2H); 1.18 (m, 1H).

MS (ESI, m/z): 494.2 [M+H$^+$] for $C_{25}H_{27}N_5O_6$.

Example 13

(4aR*,8aR*)-3-(2,3-dihydro-benzo[1,4]dioxin-6-yl)-7-[(R)-2-(3-fluoro-6-methoxy-[1,5]naphthyridin-4-yl)-2-hydroxy-ethyl]-octahydro-pyrido[4,3-e][1,3]oxazin-2-one Starting from (R)-7-fluoro-2-methoxy-8-(oxiran-2-yl)-1,5-naphthyridine (Preparation E, (R)-enantiomer, 0.048 g, 0.21 mmol) and intermediate B.ii (0.060 g, 0.207 mmol), the title compound was obtained as an off-white foam (0.059 g, 56% yield) using the procedure described in Example 3. The crude material was purified by CC (DCM/MeOH 97:3+0.3% aq. NH$_4$OH).

$^1$H NMR (d6-DMSO) δ: 8.80 (app. d, J=1.3 Hz, 1H); 8.31 (app. dd, J=1.3, 9.1 Hz, 1H); 7.28 (app. d, J=3.1, 9.1 Hz, 1H); 6.73-6.84 (m, 3H); 6.03 (m, 1H); 5.56 (dd, J=4.1, 5.7 Hz, 1H); 4.22 (s, 4H); 4.07 (s, 1.5H); 4.05 (s, 1.5H); 3.95 (td, J=4.2, 9.5 Hz, 0.5H); 3.88 (td, J=4.2, 9.5 Hz, 0.5H); 3.29-3.46 (m, 3.5H); 3.16 (dd, J=4.4, 10.4 Hz, 0.5H); 3.00-3.10 (m, 2H); 2.96 (dd, J=6.2, 12.7 Hz, 0.5H); 2.86 (m, 0.5H); 2.07-2.27 (m, 2H); 1.64-1.85 (m, 2H); 1.10 (m, 1H). MS (ESI, m/z): 511.1 [M+H$^+$] for $C_{26}H_{27}N_4O_6F$.

Examples 14 and 15

(4aS,8aS)-3-(2,3-dihydro-benzo[1,4]dioxin-6-yl)-7-[(S)-2-(3-fluoro-6-methoxy-[1,5]naphthyridin-4-yl)-2-hydroxy-ethyl]-octahydro-pyrido[4,3-e][1,3]oxazin-2-one and (4aR,8aR)-3-(2,3-dihydro-benzo[1,4]dioxin-6-yl)-7-[(S)-2-(3-fluoro-6-methoxy-[1,5]naphthyridin-4-yl)-2-hydroxy-ethyl]-octahydro-pyrido[4,3-e][1,3]oxazin-2-one 14/15.i. (4aR*,8aR*)-3-(2,3-dihydro-benzo[1,4]dioxin-6-yl)-7-[(S)-2-(3-fluoro-6-methoxy-[1,5]naphthyridin-4-yl)-2-hydroxy-ethyl]-octahydro-pyrido[4,3-e][1,3]oxazin-2-one Starting from (S)-7-fluoro-2-methoxy-8-(oxiran-2-yl)-1,5-naphthyridine (Preparation E, (S)-enantiomer, 0.048 g, 0.21 mmol) and intermediate B.ii (0.060 g, 0.207 mmol), the title compound (0.064 g, 61% yield) was prepared as off-white foam using the procedure described in Example 3. The crude material was purified by CC (DCM/MeOH 97:3+0.3% aq. NH$_4$OH).

$^1$H NMR (d6-DMSO) δ: 8.80 (app. d, J=1.3 Hz, 1H); 8.31 (app. dd, J=1.3, 9.1 Hz, 1H); 7.28 (app. d, J=3.1, 9.1 Hz, 1H); 6.73-6.84 (m, 3H); 6.03 (m, 1H); 5.56 (dd, J=4.1, 5.7 Hz, 1H); 4.22 (s, 4H); 4.07 (s, 1.5H); 4.05 (s, 1.5H); 3.95 (td, J=4.2, 9.5 Hz, 0.5H); 3.88 (td, J=4.2, 9.5 Hz, 0.5H); 3.29-3.46 (m, 3.5H); 3.16 (dd, J=4.4, 10.4 Hz, 0.5H); 3.00-3.10 (m, 2H); 2.96 (dd, J=6.2, 12.7 Hz, 0.5H); 2.86 (m, 0.5H); 2.07-2.27 (m, 2H); 1.64-1.85 (m, 2H); 1.10 (m, 1H). MS (ESI, m/z): 511.1 [M+H$^+$] for $C_{26}H_{27}N_4O_6F$.

14/15.ii. (4aS,8aS)-3-(2,3-dihydro-benzo[1,4]dioxin-6-yl)-7-[(S)-2-(3-fluoro-6-methoxy-[1,5]naphthyridin-4-yl)-2-hydroxy-ethyl]-octahydro-pyrido[4,3-e][1,3]oxazin-2-one and (4aR,8aR)-3-(2,3-dihydro-benzo[1,4]dioxin-6-yl)-7-[(S)-2-(3-fluoro-6-methoxy-[1,5]naphthyridin-4-yl)-2-hydroxy-ethyl]-octahydro-pyrido[4,3-e][1,3]oxazin-2-one Intermediates 14/15.i (0.052 g) were separated using the following chiral HPLC conditions: ChiralPak IA (Daicel, 30×250 mm, 5 μm) column, using a ratio of 1/9 of eluent A (EtOH, in the presence of 0.1% diethylamine) and eluent B (MeCN), at rt, at a flow rate of 34 mL/min. The relevant fractions were pooled and concentrated to afford each enantiomer (0.022 g).

Enantiomer 1: $t_R$=8.90 min (ChiralPak IA (Daicel, 4.6×250 mm, 5 μm), same gradient as before at a flow rate of 0.8 mL/min).

$^1$H NMR (d6-DMSO) δ: 8.80 (app. d, J=1.3 Hz, 1H); 8.31 (app. dd, J=1.3, 9.1 Hz, 1H); 7.28 (app. d, J=9.1 Hz, 1H); 6.73-6.84 (m, 3H); 6.03 (m, 1H); 5.56 (d, J=5.7 Hz, 1H); 4.22 (s, 4H); 4.05 (s, 3H); 3.95 (td, J=4.2, 9.5 Hz, 1H); 3.42 (m, 1H); 3.30 (m, 1H); 3.16 (dd, J=4.4, 10.4 Hz, 1H); 3.00-3.10

(m, 2H); 2.96 (dd, J=6.2, 12.7 Hz, 1H); 2.17 (t, J=10.3 Hz, 2H); 1.64-1.83 (m, 2H); 1.10 (m, 1H). MS (ESI, m/z): 511.1 [M+H$^+$] for C$_{26}$H$_{27}$N$_4$O$_6$F.

Enantiomer 2: t$_R$=13.10 min (ChiralPak IA (Daicel, 4.6× 250 mm, 5 μm), same gradient as before at a flow rate of 0.8 mL/min).

$^1$H NMR (d6-DMSO) δ: 8.80 (app. d, J=1.3 Hz, 1H); 8.31 (app. dd, J=1.3, 9.1 Hz, 1H); 7.28 (app. d, J=9.1 Hz, 1H); 6.73-6.84 (m, 3H); 6.03 (m, 1H); 5.56 (d, J=5.7 Hz, 1H); 4.22 (s, 4H); 4.07 (s, 3H); 3.87 (td, J=4.2, 9.5 Hz, 1H); 3.27-3.44 (m, 3H); 3.00 (d, J=6.9 Hz, 2H); 2.84 (m, 1H); 2.21 (m, 1H); 2.07 (t, J=10.7 Hz, 1H); 1.64-1.83 (m, 2H); 1.10 (m, 1H). MS (ESI, m/z): 511.1 [M+H$^+$] for C$_{26}$H$_{27}$N$_4$O$_6$F.

Example 16

(4aR*,8aR*)-3-(2,3-dihydro-benzo[1,4]dioxin-6-yl)-7-[(2RS)-2-(7-fluoro-2-methoxy-quinolin-8-yl)-2-hydroxy-ethyl]-octahydro-pyrido[4,3-e][1,3]oxazin-2-one (mixture of stereoisomers)

Starting from rac-7-fluoro-2-methoxy-8-(oxiran-2-yl)quinoline (Preparation F, 0.040 g, 0.18 mmol) and intermediate B.ii (0.050 g, 0.17 mmol), the title compound was obtained as a beige foam (0.065 g, 74% yield) using the procedure described in Example 3. The crude material was purified by CC (DCM/MeOH 13:1+0.3% aq. NH$_4$OH).

MS (ESI, m/z): 510.4 [M+H$^+$] for C$_{27}$H$_{28}$N$_3$O$_6$F.

Example 17

(4aR*,8aR*)-3-(2,3-dihydro-benzo[1,4]dioxin-6-yl)-7-[(2RS)-2-(6-fluoro-3-methoxy-quinoxalin-5-yl)-2-hydroxy-ethyl]-octahydro-pyrido[4,3-e][1,3]oxazin-2-one (mixture of stereoisomers)

Starting from rac-7-fluoro-2-methoxy-8-(oxiran-2-yl)quinoxaline (0.014 g, 0.06 mmol) and intermediate B.ii (0.018 g, 0.06 mmol), the title compound was obtained as a yellowish foam (0.013 g, 43% yield) using the procedure described in Example 3. The crude material was purified by CC (DCM/MeOH 97:3+0.3% aq. NH$_4$OH).

$^1$H NMR (d6-DMSO) δ: 8.58 (s, 1H); 7.96 (dd, J=5.5, 9.1 Hz, 1H), 7.49 (m, 1H); 6.69-6.82 (m, 3H); 5.94 (m, 1H); 5.25 (t, J=5.5 Hz, 1H); 4.19 (s, 4H); 4.06 (s, 1.5H); 4.05 (s, 1.5H); 3.90 (m, 1H); 3.32-3.43 (m, 2H); 2.78-3.16 (m, 4H); 2.07-2.27 (m, 2H); 1.64-1.85 (m, 2H); 1.10 (m, 1H). MS (ESI, m/z): 511.4 [M+H$^+$] for C$_{26}$H$_{27}$N$_4$O$_6$F.

Example 18

(4aR*,8aR*)-3-(2,3-dihydro-benzo[1,4]dioxin-6-yl)-7-[(2RS)-2-hydroxy-2-(3-methoxy-quinoxalin-5-yl)-ethyl]-octahydro-pyrido[4,3-e][1,3]oxazin-2-one (mixture of stereoisomers)

Starting from 2-methoxy-8-(oxiran-2-yl)quinoxaline (prepared as described in WO 2010/041194, 0.028 g, 0.14 mmol) and intermediate B.ii (0.040 g, 0.14 mmol), the title compound was obtained as a yellowish foam (0.042 g, 62% yield) using the procedure described in Example 3. The crude material was purified by CC (DCM/MeOH 97:3+0.3% aq. NH$_4$OH).

$^1$H NMR (d6-DMSO) δ: 8.60 (s, 1H); 7.88 (app. d, J=8.3 Hz, 2H); 7.63 (dd, J=7.3, 8.3 Hz, 1H); 6.73-6.84 (m, 3H); 5.80 (m, 1H); 5.16 (dd, J=2.1, 4.5 Hz, 1H); 4.21 (s, 4H); 4.07 (m, 1H); 4.05 (s, 3H); 3.32-3.49 (m, 2.5H); 3.25 (m, 0.5H); 3.11 (m, 0.5H); 2.95 (m, 0.5H); 2.74-2.81 (m, 1H); 2.54-2.64 (m, 1H); 2.12-2.30 (m, 2H); 1.66-1.87 (m, 2H); 1.26 (m, 1H).

MS (ESI, m/z): 493.4 [M+H$^+$] for C$_{26}$H$_{28}$N$_4$O$_6$.

Example 19 rac-(4aR*,8aR*)-7-[2-(3-fluoro-6-methoxy-[1,5]naphthyridin-4-yl)-ethyl]3-(3-oxo-3,4-dihydro-2H-pyrido[3,2-b][1,4]oxazin-6-yl)-octahydro-pyrido[4,3-e][1,3]oxazin-2-one 19.i. (4aS,8aS)-7-(2-(3-fluoro-6-methoxy-1,5-naphthyridin-4-yl)ethyl)-3-(4-(4-methoxybenzyl)-3-oxo-3,4-dihydro-2H-pyrido[3,2-b][1, 4]oxazin-6-yl)octahydro-2H-pyrido[4,3-e][1,3]oxazin-2-one Starting from 7-fluoro-2-methoxy-8-vinyl-1,5-naphthyridine (0.040 g, 0.19 mmol) and intermediate H.ii (0.070 g, 0.161 mmol), the title compound was obtained as an off-white foam (0.079 g, 64% yield) using the procedure described in Examples 1 and 2, step 1/2.i. The crude material was purified by CC (DCM/MeOH 49:1+0.2% aq. NH$_4$OH).

MS (ESI, m/z): 493.4 [M+H$^+$] for C$_{33}$H$_{33}$N$_6$O$_6$F.

19.ii. Rac-(4aR*,8aR*)-7-[2-(3-fluoro-6-methoxy-[1,5]naphthyridin-4-yl)-ethyl]-3-(3-oxo-3,4-dihydro-2H-pyrido[3,2-b][1,4]oxazin-6-yl)-octahydro-pyrido[4,3-e][1,3]oxazin-2-one To a solution of intermediate 17.i (0.08 g, 0.13 mmol) in DCM (4 mL) was added TFA (0.49 mL, 6.28 mmol, 50 eq.) and trifluoromethanesulfonic acid (0.11 mL, 1.26 mmol, 10 eq.). The reaction mixture was stirred at rt for 1 h. Aq. sat. Na$_2$CO$_3$ (6 mL) and DCM/MeOH (9:1, 8 mL) were added carefully. The two layers were separated. The pH of the aq. layer was adjusted to 12 adding 32% NaOH. The aq. layer was extracted with DCM/MeOH (9:1, 2×10 mL). The combined org. layers were dried over Na$_2$SO$_4$, filtered and concentrated to dryness. The residue was purified by CC (DCM/MeOH 97:3+0.3% NH$_4$OH) to give the title compound as a white solid (0.06 g).

$^1$H NMR (d6-DMSO) δ: 11.1 (br. s, 1H); 8.76 (s, 1H); 8.27 (d, J=9.1 Hz, 1H); 7.37 (d, J=9.1 Hz, 1H); 7.24 (d, J=7.3 Hz, 1H); 7.22 (d, J=7.3 Hz, 1H); 4.61 (s, 2H); 4.05 (overlapped m, 1H); 4.05 (s, 3H); 3.89 (m, 1H); 3.27-3.38 (m, 5H); 2.78-2.85 (m, 2H); 2.02-2.24 (m, 2H); 1.74-1.84 (m, 2H); 1.26 (m, 1H). MS (ESI, m/z): 493.4 [M+H$^+$] for C$_{25}$H$_{25}$N$_6$O$_5$F Examples 20 and 21

(4aR,8aR)-7-[2-(3-fluoro-6-methoxy-[1,5]naphthyridin-4-yl)-ethyl]-3-(3-oxo-3,4-dihydro-2H-pyrido[3,2-b][1,4]thiazin-6-yl)-octahydro-pyrido[4,3-e][1,3]oxazin-2-one and (4aS,8aS)-7-[2-(3-fluoro-6-methoxy-[1,5]naphthyridin-4-yl)-ethyl]-3-(3-oxo-3,4-dihydro-2H-pyrido[3,2-b][1,4]thiazin-6-yl)-octahydro-pyrido[4,3-e][1,3]oxazin-2-one 20/21.i. Rac-(4aR*,8aR*)-7-[2-(3-fluoro-6-methoxy-[1,5]naphthyridin-4-yl)-ethyl]-3-(3-oxo-3,4-dihydro-2H-pyrido[3,2-b][1,4]thiazin-6-yl)-octahydro-pyrido[4,3-e][1,3]oxazin-2-one Starting from 7-fluoro-2-methoxy-8-vinyl-1,5-naphthyridine (0.028 g, 0.13 mmol) and intermediate H.ii (0.060 g, 0.13 mmol), the title compound was obtained as an off-white foam (0.050 g) using the procedure described in Examples 1 and 2, step 1/2.i (alkene addition: 84% yield) and Example 19, step 19.ii (PMB deprotection: 88% yield). The crude material was purified by CC (DCM/MeOH 97:3+0.3% aq. NH$_4$OH).

$^1$H NMR (d6-DMSO) δ: 10.84 (s, 1H); 8.77 (s, 1H); 8.27 (d, J=9.1 Hz, 1H); 7.75 (d, J=8.4 Hz, 1H); 7.40 (d, J=8.4 Hz, 1H); 7.23 (d, J=9.0 Hz, 1H); 4.01-4.11 (overlapped m, 2H); 4.05 (s, 3H); 3.52 (s, 2H); 3.28-3.38 (m, 4H); 2.99 (m, 1H); 2.70-2.86 (m, 2H); 2.07-2.26 (m, 2H); 1.72-1.86 (m, 2H); 1.26 (m, 1H). MS (ESI, m/z): 525.2 [M+H$^+$] for C$_{25}$H$_{25}$N$_6$O$_4$FS.

20/21.ii. (4aR,8aR)-7-[2-(3-fluoro-6-methoxy-[1,5]naphthyridin-4-yl)-ethyl]-3-(3-oxo-3,4-dihydro-2H-pyrido[3,2-b][1,4]thiazin-6-yl)-octahydro-pyrido[4,3-e][1,3]oxazin-2-one and (4aS,8aS)-7-[2-(3-fluoro-6-methoxy-[1,5]naphthyridin-4-yl)-ethyl]-3-(3-oxo-3,4-dihydro-2H-pyrido[3,2-b][1,4]thiazin-6-yl)-octahydro-pyrido[4,3-e][1,3]oxazin-2-one Intermediates 20/21.i (0.042 g) were separated using the following chiral HPLC conditions: ChiralPak IB (Daicel, 30×250 mm, 5 μm) column, using a ratio of 1/9 of eluent A (EtOH, in the presence of 0.1% diethylamine) and eluent B (MeCN), at rt, at a flow rate of 34 mL/min. The relevant fractions were pooled and concentrated to afford each enantiomer (0.006 g).

Enantiomer 1: t$_R$=7.45 min (ChiralPak IB (Daicel, 4.6×250 mm, 5 μm) same gradient as before at a flow rate of 0.8 mL/min).

$^1$H NMR (d6-DMSO) δ: 10.84 (s, 1H); 8.77 (s, 1H); 8.27 (d, J=9.1 Hz, 1H); 7.75 (d, J=8.4 Hz, 1H); 7.40 (d, J=8.4 Hz, 1H); 7.23 (d, J=9.0 Hz, 1H); 4.01-4.11 (overlapped m, 2H); 4.05 (s, 3H); 3.52 (s, 2H); 3.28-3.38 (m, 4H); 2.99 (m, 1H); 2.70-2.86 (m, 2H); 2.07-2.26 (m, 2H); 1.72-1.86 (m, 2H); 1.26 (m, 1H). MS (ESI, m/z): 525.3 [M+H$^+$] for C$_{25}$H$_{25}$N$_6$O$_4$FS.

Enantiomer 2: t$_R$=13.10 min (ChiralPak IB (Daicel, 4.6×250 mm, 5 μm) same gradient as before at a flow rate of 0.8 mL/min).

$^1$H NMR (d6-DMSO) δ: 10.84 (s, 1H); 8.77 (s, 1H); 8.27 (d, J=9.1 Hz, 1H); 7.75 (d, J=8.4 Hz, 1H); 7.40 (d, J=8.4 Hz, 1H); 7.23 (d, J=9.0 Hz, 1H); 4.01-4.11 (overlapped m, 2H); 4.05 (s, 3H); 3.52 (s, 2H); 3.28-3.38 (m, 4H); 2.99 (m, 1H); 2.70-2.86 (m, 2H); 2.07-2.26 (m, 2H); 1.72-1.86 (m, 2H); 1.26 (m, 1H). MS (ESI, m/z): 525.2 [M+H$^+$] for C$_{25}$H$_{25}$N$_6$O$_4$FS.

Example 22 rac-(4aR*,8aR*)-3-(2,3-dihydro-[1,4]dioxino[2,3-b]pyridin-7-yl)-7-[2-(3-fluoro-6-methoxy-[1,5]naphthyridin-4-yl)-ethyl]-octahydro-pyrido[4,3-e][1,3]oxazin-2-one Starting from 7-fluoro-2-methoxy-8-vinyl-1,5-naphthyridine (0.048 g, 0.23 mmol) and intermediate J (0.072 g, 0.24 mmol), the title compound was obtained as a beige foam (0.078 g, 67% yield) using the procedure described in Examples 1 and 2, step 1/2.i. The crude material was purified by CC (DCM/MeOH 97:3+0.3% aq. NH$_4$OH).

$^1$H NMR (d6-DMSO) δ: 8.77 (s, 1H); 8.27 (d, J=9.1 Hz, 1H); 7.72 (d, J=2.3 Hz, 1H); 7.34 (d, J=2.3 Hz, 1H); 7.23 (d, J=9.1 Hz, 1H); 4.35-4.40 (m, 2H); 4.15-4.21 (m, 2H); 4.07 (overlapped m, 1H), 4.05 (s, 3H); 3.26-3.50 (m, 5H); 2.97 (m, 1H); 2.77-2.85 (m, 2H), 2.15 (m, 1H); 2.10 (t, J=10.0 Hz, 1H); 1.84 (m, 1H); 1.74 (m, 1H); 1.20 (m, 1H). MS (ESI, m/z): 496.3 [M+H$^+$] for C$_{25}$H$_{26}$N$_5$O$_5$F.

Example 23 rac-(4aR*,8aR*)-3-(6,7-dihydro-[1,4]dioxino[2,3-c]pyridazin-3-yl)-7-[2-(3-fluoro-6-methoxy-[1,5]naphthyridin-4-yl)-ethyl]-octahydro-pyrido[4,3-e][1,3]oxazin-2-one Starting from 7-fluoro-2-methoxy-8-vinyl-1,5-naphthyridine (0.023 g, 0.11 mmol) and intermediate K (0.033 g, 0.11 mmol), the title compound was obtained as a yellowish foam (0.037 g, 66% yield) using the procedure described in Examples 1 and 2, step 1/2.i. The crude material was purified by CC (DCM/MeOH 97:3+0.3% aq. NH$_4$OH).

$^1$H NMR (d6-DMSO) δ: 8.76 (s, 1H); 8.27 (d, J=9.1 Hz, 1H); 7.43 (s, 1H); 7.23 (d, J=9.1 Hz, 1H); 4.47-4.51 (m, 2H); 4.36-4.40 (m, 2H); 4.05-4.15 (m, 2H), 4.05 (s, 3H); 3.46 (t, J=11.3 Hz, 1H); 3.28-3.36 (m, 3H); 2.98 (m, 1H); 2.77-2.86 (m, 2H); 2.08-2.26 (m, 2H); 1.77-1.90 (m, 2H); 1.25 (m, 1H). MS (ESI, m/z): 497.3 [M+H$^+$] for C$_{24}$H$_{25}$N$_6$O$_5$F.

Example 24 rac-(4aR*,8aR*)-3-(2,3-dihydro-[1,4]dioxino[2,3-c]pyridin-7-yl)-7-[2-(3-fluoro-6-methoxy-[1,5]naphthyridin-4-yl)-ethyl]-octahydro-pyrido[4,3-e][1,3]oxazin-2-one Starting from 7-fluoro-2-methoxy-8-vinyl-1,5-naphthyridine (0.041 g, 0.2 mmol) and intermediate L (0.061 g, 0.21 mmol), the title compound was obtained as an off-white foam (0.047 g, 48% yield) using the procedure described in Examples 1 and 2, step 1/2.i. The crude material was purified by CC (DCM/MeOH 97:3+0.3% aq. NH$_4$OH).

$^1$H NMR (d6-DMSO) δ: 8.76 (d, J=0.3 Hz, 1H); 8.27 (d, J=9.1 Hz, 1H); 7.92 (s, 1H), 7.23 (d, J=9.1 Hz, 1H); 7.18 (s, 1H); 4.31-4.35 (m, 2H); 4.25-4.29 (m, 2H); 4.05 (s, 3H); 4.03 (m, 1H); 3.93 (dd, J=5.1, 11.6 Hz, 1H); 3.26-3.37 (m, 4H); 2.97 (m, 1H); 2.76-2.83 (m, 2H); 2.17 (m, 1H); 2.10 (t, J=10.1 Hz, 1H); 1.69-1.84 (m, 2H); 1.25 (m, 1H).

MS (ESI, m/z): 496.3 [M+H$^+$] for C$_{25}$H$_{26}$N$_5$O$_5$F.

Example 25 rac-(4aR*,8aR*)-7-[2-(7-methoxy-2-oxo-2H-[1,8]naphthyridin-1-yl)-ethyl]-3-(3-oxo-3,4-dihydro-2H-pyrido[3,2-b][1,4]oxazin-6-yl)-octahydro-pyrido[4,3-e][1,3]oxazin-2-one Starting from 2-(7-methoxy-2-oxo-1,8-naphthyridin-1(2H)-yl)acetaldehyde (prepared as described in WO 2008/009700, 0.038 g, 0.18 mmol) and intermediate H (0.072 g, 0.17 mmol), the title compound was obtained as a colourless foam (0.060 g) using the procedures described in Example 7 (reductive amination: 85% yield) and Example 19, step 19.ii (PMB deprotection: 82% yield). The crude material was purified by CC (DCM/MeOH 97:3+0.3% aq. NH$_4$OH).

$^1$H NMR (d6-DMSO) δ: 11.18 (s, 1H); 8.04 (d, J=8.5 Hz, 1H); 7.85 (d, J=9.4 Hz, 1H); 7.37 (d, J=8.4 Hz, 1H); 7.21 (d, J=8.5 Hz, 1H), 6.72 (d, J=8.4 Hz, 1H), 6.49 (d, J=9.4 Hz, 1H); 4.61 (s, 2H), 4.44-4.56 (m, 2H); 4.06 (m, 1H); 3.98 (s, 3H); 3.88 (m, 1H); 3.30-3.39 (m, 2H); 2.98 (m, 1H); 2.68-2.78 (m, 2H), 2.18 (m, 1H), 2.11 (t, J=10.1 Hz, 1H); 1.71-1.86 (m, 2H); 1.27 (m, 1H). MS (ESI, m/z): 507.2 [M+H$^+$] for C$_{25}$H$_{26}$N$_6$O$_6$.

Example 26 rac-(4aR*,8aR*)-7-[2-(7-methoxy-2-oxo-2H-[1,8] naphthyridin-1-yl)-ethyl]-3-(3-oxo-3,4-dihydro-2H-pyrido[3,2-b][1,4]thiazin-6-yl)-octahydro-pyrido[4,3-e][1,3]oxazin-2-one

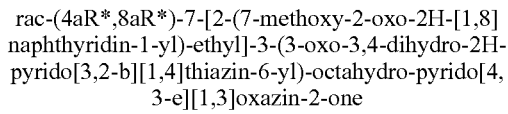

Starting from 2-(7-methoxy-2-oxo-1,8-naphthyridin-1 (2H)-yl)acetaldehyde (prepared as described in WO 2008/009700, 0.028 g, 0.12 mmol) and intermediate I (0.053 g, 0.12 mmol), the title compound was obtained as a colourless foam (0.024 g) using the procedures described in Example 7 (reductive amination: 56% yield) and Example 19, step 19.ii (PMB deprotection: 69% yield). The crude material was purified by CC (DCM/MeOH 97:3+0.3% aq. NH$_4$OH).

$^1$H NMR (d6-DMSO) δ: 10.85 (s, 1H), 8.04 (d, J=8.5 Hz, 1H); 7.85 (d, J=9.4 Hz, 1H); 7.75 (d, J=8.4 Hz, 1H); 7.41 (d, J=8.4 Hz, 1H); 6.72 (d, J=8.4 Hz, 1H); 6.49 (d, J=9.4 Hz, 1H); 4.44-4.58 (m, 2H); 3.98-4.12 (m, 2H); 3.98 (s, 3H); 3.52 (s, 2H); 3.27-3.38 (m, 2H); 2.98 (m, 1H); 2.69-2.78 (m, 2H); 2.19 (m, 1H), 2.11 (t, J=10.1 Hz, 1H); 1.72-1.86 (m, 2H); 1.28 (m, 1H). MS (ESI, m/z): 523.0 [M+H$^+$] for C$_{25}$H$_{26}$N$_6$O$_5$S.

Example 27 rac-(4aR*,8aR*)-3-(6,7-dihydro-8-oxa-5-thia-1,2-diaza-naphthalen-3-yl)-7-[2-(3-fluoro-6-methoxy-[1,5]naphthyridin-4-yl)-ethyl]-octahydro-pyrido[4,3-e][1,3]oxazin-2-one

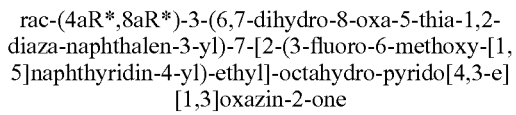

Starting from 7-fluoro-2-methoxy-8-vinyl-1,5-naphthyridine (0.030 g, 0.147 mmol) and intermediate M (0.046 g, 0.147 mmol), the title compound was obtained as a yellowish foam (0.036 g, 48% yield) using the procedure described in Examples 1 and 2, step 1/2.i. The crude material was purified by CC (DCM/MeOH 97:3+0.3% aq. NH$_4$OH).

$^1$H NMR (d6-DMSO) δ: 8.76 (d, J=0.5 Hz, 1H), 8.27 (d, J=9.1 Hz, 1H), 7.79 (s, 1H), 7.23 (d, J=9.1 Hz, 1H); 4.55-4.60 (m, 2H); 3.99-4.13 (m, 2H); 4.05 (s, 3H); 3.25-3.37 (m, 6H); 2.97 (m, 1H); 2.77-2.85 (m, 2H); 2.18 (m, 1H); 2.12 (t, J=10.2 Hz, 1H); 1.76-1.84 (m, 2H); 1.25 (m, 1H). MS (ESI, m/z): 512.9 [M+H$^+$] for C$_{24}$H$_{25}$N$_6$O$_4$FS.

Example 28 rac-(4aR*,8aR*)-3-(6,7-dihydro-8-oxa-5-thia-1,2-diaza-naphthalen-3-yl)-7-[2-(6-methoxy-3-oxo-3H-pyrido[2,3-b]pyrazin-4-yl)-ethyl]-octahydro-pyrido[4,3-e][1,3]oxazin-2-one

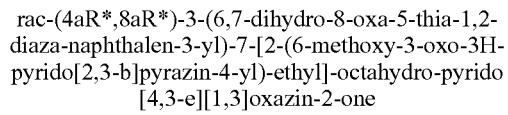

Starting from 2-(6-methoxy-3-oxopyrido[2,3-b]pyrazin-4 (3H)-yl)acetaldehyde (prepared as described in WO 2008/009700, 0.02 g, 0.08 mmol) and intermediate M (0.025 g, 0.08 mmol), the title compound was obtained as a white solid (0.020 g, 50% yield) using the procedure described in Example 8. The crude material was purified by a preparative HPLC (Method A).

$^1$H NMR (d6-DMSO) δ: 8.12 (d, J=8.6 Hz, 1H); 8.11 (s, 1H); 7.79 (s, 1H); 6.84 (d, J=8.6 Hz, 1H); 4.55-4.60 (m, 2H); 4.38-4.53 (m, 2H); 4.01 (s, 3H); 3.99-4.11 (m, 2H); 3.44 (t, J=11.4 Hz, 1H); 3.25-3.35 (m, 3H); 2.97 (m, 1H); 3.25-3.35 (m, 2H); 2.18 (m, 1H); 2.12 (t, J=10.2 Hz, 1H); 1.76-1.84 (m, 2H); 1.25 (m, 1H). MS (ESI, m/z): 512.2 [M+H$^+$] for C$_{23}$H$_{25}$N$_7$O$_5$S.

Example 29

(R)-2-[(4aR*,8aR*)-3-(2,3-dihydro-benzo[1,4]dioxin-6-yl)-2-oxo-octahydro-pyrido[4,3-e][1,3]oxazin-7-ylmethyl]-9-fluoro-1,2-dihydro-pyrrolo[3,2,1-ij]quinolin-4-one (mixture of stereoisomers)

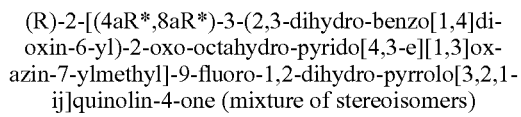

To a solution of intermediate B.ii (0.057 g, 0.20 mmol) in DMF (1.6 mL) were added (R)-(9-fluoro-4-oxo-2,4-dihydro-1H-pyrrolo[3,2,1-ij]quinolin-2-yl)methyl methanesulfonate (prepared as described in WO 2009/104147, 0.068 g, 0.23 mmol) and DIPEA (0.067 mL, 0.39 mmol). The mixture was stirred at 80° C. for 48 h. The solvent was removed in vacuo. The residue was partitioned between sat. aq. NaHCO$_3$ (5 mL) and DCM/MeOH (9:1, 10 mL). The phases were separated and the aq. layer was extracted twice with the same mixture (2×10 mL). The combined org. layers were dried over Na$_2$SO$_4$, filtered and concentrated to dryness. The residue was purified by a preparative HPLC (Method A) to give the title compound formate salt as a white solid (0.007 g, 6% yield).

MS (ESI, m/z): 492.25 [M+H$^+$] for C$_{24}$H$_{25}$N$_6$O$_4$FS.

Example 30

(RS)-4-[(4aR*,8aR*)-3-(2,3-dihydro-benzo[1,4]dioxin-6-yl)-2-oxo-octahydro-pyrido[4,3-e][1,3]oxazin-7-ylmethyl]-3-fluoro-4,5-dihydro-pyrrolo[3,2,1-de][1,5]naphthyridin-7-one (mixture of stereoisomers)

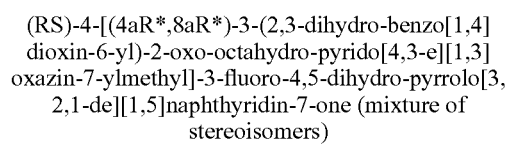

Starting from 3-fluoro-4-methylene-4H-pyrrolo[3,2,1-de][1,5]naphthyridin-7(5H)-one (prepared as described in WO 2007/071936, 0.058 g, 0.29 mmol) and intermediate B.ii (0.041 g, 0.14 mmol), the title compound was obtained as a yellow solid (0.012 g, 18% yield) using the procedure described in Examples 1 and 2, step 1/2.i. The crude material was purified by CC (DCM/MeOH 19:1+0.5% aq. NH$_4$OH).

MS (ESI, m/z): 512.9 [M+H$^+$] for C$_{26}$H$_{25}$N$_4$O$_5$F.

Example 31 rac-(4aR*,8aR*)-7-(2-(7-methoxy-2-oxo-1,8-naphthyridin-1(2H)-yl)ethyl)-3-(3-oxo-3,4-dihydro-2H-benzo[b][1,4]thiazin-6-yl)octahydro-2H-pyrido[4,3-e][1,3]oxazin-2-one

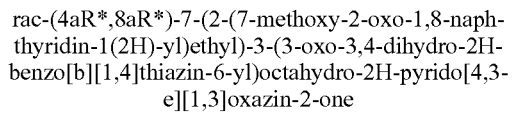

Starting from 2-(7-methoxy-2-oxo-1,8-naphthyridin-1 (2H)-yl)acetaldehyde (prepared as described in WO 2008/009700; 0.030 g; 0.14 mmol) and intermediate D (0.058 g, 0.13 mmol), the title compound was obtained as a colourless foam (0.040 g) using the procedures described in Example 7 (reductive amination: 77% yield) and Example 19, step 19.ii (PMB deprotection: 76% yield). The crude material was purified by CC (DCM/MeOH 97:3+0.3% aq. NH$_4$OH).

$^1$H NMR (d6-DMSO) δ: 10.5 (s, 1H); 8.04 (d, J=8.5 Hz, 1H); 7.86 (d, J=9.4 Hz, 1H); 7.30 (d, J=8.4 Hz, 1H), 6.94-6.97 (m, 2H); 6.73 (d, J=8.4 Hz, 1H), 6.49 (d, J=9.4 Hz, 1H); 4.44-4.56 (m, 2H); 4.08 (m, 1H); 3.98 (s, 3H); 3.38-3.51 (m, 2H); 3.45 (s, 2H); 3.31 (m, 1H); 2.98 (m, 1H); 2.69-2.79 (m, 2H); 2.17 (m, 1H); 2.10 (t, J=10.1 Hz, 1H); 1.71-1.86 (m, 2H); 1.24 (m, 1H). MS (ESI, m/z): 522.0 [M+H$^+$] for C$_{26}$H$_{27}$N$_5$O$_5$S.

Example 32

(4aR*,8aR*)-7-((2RS)-2-(3-fluoro-6-methoxy-1,5-naphthyridin-4-yl)-2-hydroxyethyl)-3-(3-oxo-3,4-dihydro-2H-benzo[b][1,4]oxazin-6-yl)octahydro-2H-pyrido[4,3-e][1,3]oxazin-2-one Starting from rac-7-fluoro-2-methoxy-8-(oxiran-2-yl)-1,5-naphthyridine (prepared as described in WO 2004/058144; 0.044 g; 0.2 mmol) and intermediate C.i (0.080 g, 0.19 mmol), the title compound was obtained as a yellow foam (0.033 g) using the procedures described in Example 3 (epoxide opening, 74% yield) and Example 19, step 19.ii (PMB deprotection, 44% yield). The crude material was purified by CC (DCM/MeOH 13:1+0.3% aq. $NH_4OH$).

MS (ESI, m/z): 524.4 [M+H$^+$] for $C_{26}H_{26}N_5O_6F$.

Example 33

(4aR*,8aR*)-7-0(R)-9-fluoro-4-oxo-2,4-dihydro-1H-pyrrolo[3,2,1-ij]quinolin-2-yl)methyl)-3-(3-oxo-3,4-dihydro-2H-pyrido[3,2-b][1,4]oxazin-6-yl)octahydro-2H-pyrido[4,3-e][1,3]oxazin-2-one Starting from intermediate H (0.110 g, 0.336 mmol) and (R)-(9-fluoro-4-oxo-2,4-dihydro-1H-pyrrolo[3,2,1-ij]quinolin-2-yl)methyl methanesulfonate (prepared as described in WO 2009/104147; 0.110 g, 0.26 mmol), the title compound was obtained as a yellow foam (0.061 g) using the procedure described in Example 29 (mesylate displacement, 54% yield) and Example 19, step 19.ii (PMB deprotection, 90% yield). The crude material was purified by CC (DCM/MeOH 13:1+0.3% aq. $NH_4OH$).

MS (ESI, m/z): 506.2 [M+H$^+$] for $C_{26}H_{24}N_5O_5F$.

Example 34 rac-(4aR*,8aR*)-7-(2-(7-methoxy-2-oxo-1,8-naphthyridin-1(2H)-yl)ethyl)-3-(3-oxo-3,4-dihydro-2H-benzo[b][1,4]oxazin-6-yl)octahydro-2H-pyrido[4,3-e][1,3]oxazin-2-one Starting from 2-(7-methoxy-2-oxo-1,8-naphthyridin-1(2H)-yl)acetaldehyde (prepared as described in WO 2008/009700; 0.030 g; 0.14 mmol) and intermediate C.i (0.057 g, 0.135 mmol), the title compound was obtained as a colourless foam (0.029 g) using the procedures described in Example 7 (reductive amination: 50% yield) and Example 19, step 19.ii (PMB deprotection: 85% yield). The crude material was purified by CC (DCM/MeOH 97:3+0.3% aq. $NH_4OH$).

$^1$H NMR (d6-DMSO) δ: 10.7 (s, 1H); 8.04 (d, J=8.5 Hz, 1H); 7.85 (d, J=9.4 Hz, 1H); 6.83-6.93 (m, 3H); 6.73 (d, J=8.4 Hz, 1H), 6.49 (d, J=9.4 Hz, 1H); 4.54 (s, 2H); 4.44-4.56 (m, 2H); 4.08 (m, 1H); 3.98 (s, 3H); 3.38-3.49 (m, 2H); 3.32 (m, 1H); 2.98 (m, 1H); 2.68-2.80 (m, 2H); 2.16 (m, 1H), 2.09 (t, J=10.1 Hz, 1H); 1.71-1.86 (m, 2H); 1.22 (m, 1H).

MS (ESI, m/z): 506.2 [M+H$^+$] for $C_{26}H_{27}N_5O_6$.

Pharmacological Properties of the Invention Compounds
In Vitro Assays
Bacterial Growth Minimal Inhibitory Concentrations:
Experimental Methods:

Minimal inhibitory concentrations (MICs; mg/l) were determined in cation-adjusted Mueller-Hinton Broth by a microdilution method following the description given in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA, 2006.

All Example compounds were tested against several Gram positive and Gram negative bacteria. Typical antibacterial test results are given in the table hereafter (MIC in mg/l).

| Example No. | MIC for S. aureus 29213 | Example No. | MIC for S. aureus 29213 |
|---|---|---|---|
| 1 | ≤0.031 | 2 | ≤0.031 |
| 3 | 0.125 | 4 | 0.063 |
| 5 | ≤0.031 | 6 | 0.063 |
| 7 | ≤0.031 | 8 | ≤0.031 |
| 9 | ≤0.031 | 10 | ≤0.031 |
| 11 | ≤0.031 | 12 | ≤0.031 |
| 13 | 0.063 | 14 | ≤0.031 |
| 15 | 0.063 | 16 | 0.125 |
| 17 | 0.063 | 18 | 0.063 |
| 19 | ≤0.031 | 20 | ≤0.031 |
| 21 | ≤0.031 | 22 | ≤0.031 |
| 23 | ≤0.031 | 24 | ≤0.031 |
| 25 | ≤0.031 | 26 | ≤0.031 |
| 27 | ≤0.031 | 28 | ≤0.031 |
| 29 | 0.25 | 30 | 0.5 |
| 31 | ≤0.031 | 32 | 0.125 |
| 33 | 0.125 | 34 | 0.25 |

The invention claimed is:

1. A compound of formula I comprising a relative trans configuration of the octahydro-pyrido[4,3-e][1,3]oxazinone moiety

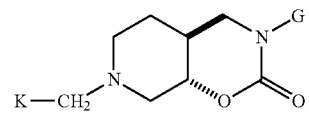

wherein
K represents the group Ka

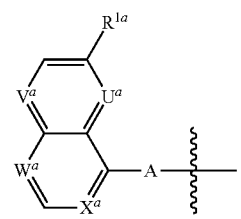

wherein R$^{1a}$ represents alkoxy, halogen or cyano;
one or two of U$^a$, V$^a$, W$^a$ represent(s) N and the remaining two or one of U$^a$, V$^a$, W$^a$ represent(s) CH;
X$^a$ represents CR$^a$ wherein R$^a$ represents hydrogen or halogen;
A represents CHR$^b$ wherein R$^b$ represents hydrogen or hydroxyl;

or K represents the group Kb

Kb wherein R$^{1b}$ represents hydrogen, alkoxy, halogen or cyano;
one or two of U$^b$, V$^b$ and W$^b$ represent(s) N and the remaining two or one of U$^b$, V$^b$ W$^b$ represent(s) CH;
or K represents the group Kc or Kd wherein Kc Kd wherein R$^{1c}$ and R$^{1d}$ independently represent H or F;
V$^c$, V$^d$, W$^c$ and W$^d$ independently represent CH or N; and
G represents one of the groups Ga, Gb, Gc and Gd (Ga)

(Gb)

(Gc)

(Gd)

wherein M represents CH or N; and Q and Q' independently represent O or S;
or a salt of the compound.

2. The compound according to claim 1, wherein K represents the group Ka or Kb;
or a salt of the compound.

3. The compound according to claim 2, wherein K represents the group Ka wherein R1a represents methoxy, or wherein K represents the group Kb wherein R1b represents methoxy;
or a salt of the compound.

4. The compound according to claim 2, wherein K represents the group Ka;
or a salt of the compound.

5. The compound according to claim 1, wherein A represents CHRb wherein Rb represents hydrogen;
or a salt of the compound.

6. The compound according to claim 1, wherein A represents CHRb wherein Rb represents hydroxyl, and the absolute configuration of the carbon atom to which Rb is attached to is (R);
or a salt of the compound.

7. The compound according to claim 2, wherein K represents the group Kb;
or a salt of the compound.

8. The compound according to claim 1, wherein G represents a group of (Ga)

(Gb)

(Gc)

, or (Gd)

wherein
M represents CH and Q' represent O or S; or
M represents N and Q' represents S; and
Q represents O or S;
or a salt of the compound.

9. The compound according to claim 1, wherein:
K represents the group Ka

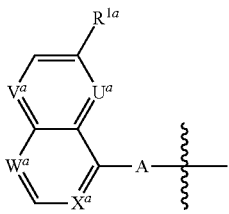

wherein $R^{1a}$ represents methoxy;
$U^a$ and $W^a$ each represent N and $V^a$ and $X^a$ each represent CH;
$X^a$ represents $CR^a$ wherein $R^a$ represents fluorine;
A represents $CHR^b$ wherein $R^b$ represents hydrogen or hydroxyl;
or K represents the group Kb

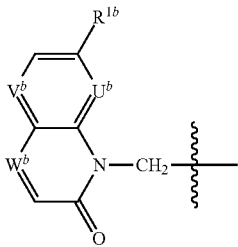

wherein $R^{1b}$ represents methoxy;
$U^b$ represents N, $V^b$ represents CH and $W^b$ represents CH or N; and
G represents one of the groups Gb and Gc

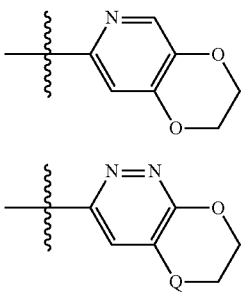

wherein Q represents O or S;
or a salt of the compound.

10. The compound according to claim 1, wherein the compound is:
(4aR,8aR)-3-(2,3-dihydro-benzo[1,4]dioxin-6-yl)-7-[2-(3-fluoro-6-methoxy-[1,5]naphthyridin-4-yl)-ethyl]-octahydro-pyrido[4,3-e][1,3]oxazin-2-one;
(4aS,8aS)-3-(2,3-dihydro-benzo[1,4]dioxin-6-yl)-7-[2-(3-fluoro-6-methoxy-[1,5]naphthyridin-4-yl)-ethyl]-octahydro-pyrido[4,3-e][1,3]oxazin-2-one;
(4aR*,8aR*)-3-(2,3-dihydro-benzo[1,4]dioxin-6-yl)-7-[2-hydroxy-2-(6-methoxy-[1,5]naphthyridin-4-yl)-ethyl]-octahydro-pyrido[4,3-e][1,3]oxazin-2-one;
(4aR*,8aR*)-3-(2,3-dihydro-benzo[1,4]dioxin-6-yl)-7-[2-(6-methoxy-[1,5]naphthyridin-4-yl)-ethyl]-octahydro-pyrido[4,3-e][1,3]oxazin-2-one;
(4aR*,8aR*)-7-[2-(3-fluoro-6-methoxy-[1,5]naphthyridin-4-yl)-ethyl]-3-(3-oxo-3,4-dihydro-2H-benzo[1,4]oxazin-6-yl)-octahydro-pyrido[4,3-e][1,3]oxazin-2-one;
(4aR*,8aR*)-3-(2,3-dihydro-benzo[1,4]dioxin-6-yl)-7-[2-(3-fluoro-6-methoxy-[1,5]naphthyridin-4-yl)-2-hydroxy-ethyl]-octahydro-pyrido[4,3-e][1,3]oxazin-2-one;
(4aR*,8aR*)-7-[2-(3-fluoro-6-methoxy-[1,5]naphthyridin-4-yl)-ethyl]-3-(3-oxo-3,4-dihydro-2H-benzo[1,4]thiazin-6-yl)-octahydro-pyrido[4,3-e][1,3]oxazin-2-one;
(4aR*,8aR*)-3-(2,3-dihydro-benzo[1,4]dioxin-6-yl)-7-[2-(7-methoxy-2-oxo-2H-quinolin-1-yl)-ethyl]-octahydro-pyrido[4,3-e][1,3]oxazin-2-one;
(4aR*,8aR*)-3-(2,3-dihydro-benzo[1,4]dioxin-6-yl)-7-[2-(7-methoxy-2-oxo-2H-quinoxalin-1-yl)-ethyl]-octahydro-pyrido[4,3-e][1,3]oxazin-2-one;
(4aR*,8aR*)-3-(2,3-dihydro-benzo[1,4]dioxin-6-yl)-7-[2-(7-methoxy-2-oxo-2H-[1,8]naphthyridin-1-yl)-ethyl]-octahydro-pyrido[4,3-e][1,3]oxazin-2-one;
(4aR*,8aR*)-3-(2,3-dihydro-benzo[1,4]dioxin-6-yl)-7-[2-(6-methoxy-3-oxo-3H-pyrido[2,3-b]pyrazin-4-yl)-ethyl]-octahydro-pyrido[4,3-e][1,3]oxazin-2-one;
(4aR*,8aR*)-3-(2,3-dihydro-benzo[1,4]dioxin-6-yl)-7-[2-(3-methoxy-6-oxo-6H-pyrido[2,3-b]pyrazin-5-yl)-ethyl]-octahydro-pyrido[4,3-e][1,3]oxazin-2-one;
(4aR*,8aR*)-3-(2,3-dihydro-benzo[1,4]dioxin-6-yl)-7-[(R)-2-(3-fluoro-6-methoxy-[1,5]naphthyridin-4-yl)-2-hydroxy-ethyl]octahydro-pyrido[4,3-e][1,3]oxazin-2-one;
(4aS,8aS)-3-(2,3-dihydro-benzo[1,4]dioxin-6-yl)-7-[(S)-2-(3-fluoro-6-methoxy-[1,5]naphthyridin-4-yl)-2-hydroxy-ethyl]-octahydro-pyrido[4,3-e][1,3]oxazin-2-one;
(4aR,8aR)-3-(2,3-dihydro-benzo[1,4]dioxin-6-yl)-7-[(S)-2-(3-fluoro-6-methoxy-[1,5]naphthyridin-4-yl)-2-hydroxy-ethyl]-octahydro-pyrido[4,3-e][1,3]oxazin-2-one;
(4aR*,8aR*)-3-(2,3-dihydro-benzo[1,4]dioxin-6-yl)-7-[2-(7-fluoro-2-methoxy-quinolin-8-yl)-2-hydroxy-ethyl]-octahydro-pyrido[4,3-e][1,3]oxazin-2-one;
(4aR*,8aR*)-3-(2,3-dihydro-benzo[1,4]dioxin-6-yl)-7-[2-(6-fluoro-3-methoxy-quinoxalin-5-yl)-2-hydroxy-ethyl]-octahydro-pyrido[4,3-e][1,3]oxazin-2-one;
(4aR*,8aR*)-3-(2,3-dihydro-benzo[1,4]dioxin-6-yl)-7-[2-hydroxy-2-(3-methoxy-quinoxalin-5-yl)-ethyl]-octahydro-pyrido[4,3-e][1,3]oxazin-2-one;
(4aR*,8aR*)-7-[2-(3-fluoro-6-methoxy[1,5]naphthyridn-4-yl)-ethyl]-3-(3-oxo-3,4-dihydro-2H-pyrido[3,2-b][1,4]oxazin-6-yl)-octahydro-pyrido[4,3-e][1,3]oxazin-2-one;
(4aR,8aR)-7-[2-(3-fluoro-6-methoxy-[1,5]naphthyridin-4-yl)-ethyl]-3-(3-oxo-3,4-dihydro-2H-pyrido[3,2-b][1,4]thiazin-6-yl)-octahydro-pyrido[4,3-e][1,3]oxazin-2-one;

(4aS,8aS)-7-[2-(3-fluoro-6-methoxy-[1,5]naphthyridin-4-yl)-ethyl]-3-(3-oxo-3,4-dihydro-2H-pyrido[3,2-b][1,4]thiazin-6-yl)-octahydro-pyrido[4,3-e][1,3]oxazin-2-one;

(4aR*,8aR*)-3-(2,3-dihydro-[1,4]dioxino[2,3-b]pyridin-7-yl)-7-[2-(3-fluoro-6-methoxy-[1,5]naphthyridin-4-yl)-ethyl]octahydro-pyrido[4,3-e][1,3]oxazin-2-one;

(4aR*,8aR*)-3-(6,7-dihydro-[1,4]dioxino[2,3-c]pyridazin-3-yl)-7-[2-(3-fluoro-6-methoxy-[1,5]naphthyridin-4-yl)-ethyl]-octahydro-pyrido[4,3-e][1,3]oxazin-2-one;

(4aR*,8aR*)-3-(2,3-dihydro-[1,4]dioxino[2,3-c]pyridin-7-yl)-7-[2-(3-fluoro-6-methoxy-[1,5]naphthyridin-4-yl)-ethyl]-octahydro-pyrido[4,3-e][1,3]oxazin-2-one;

(4aR*,8aR*)-7-[2-(7-methoxy-2-oxo-2H-[1,8]naphthyridin-1-yl)-ethyl]-3-(3-oxo-3,4-dihydro-2H-pyrido[3,2-b][1,4]oxazin-6-yl)-octahydro-pyrido[4,3-e][1,3]oxazin-2-one;

(4aR*,8aR*)-7-[2-(7-methoxy-2-oxo-2H-[1,8]naphthyridin-1-yl)-ethyl]-3-(3-oxo-3,4-dihydro-2H-pyrido[3,2-b][1,4]thiazin-6-yl)-octahydro-pyrido[4,3-e][1,3]oxazin-2-one;

(4aR*,8aR*)-3-(6,7-dihydro-8-oxa-5-thia-1,2-diaza-naphthalen-3-yl)-7-[2-(3-fluoro-6-methoxy-[1,5]naphthyridin-4-yl)-ethyl]-octahydro-pyrido[4,3-e][1,3]oxazin-2-one;

(4aR*,8aR*)-3-(6,7-dihydro-8-oxa-5-thia-1,2-diaza-naphthalen-3-yl)-7-[2-(6-methoxy-3-oxo-3H-pyrido[2,3-b]pyrazin-4-yl)-ethyl]-octahydro-pyrido[4,3-e][1,3]oxazin-2-one;

(R)-2-[(4aR*,8aR*)-3-(2,3-dihydro-benzo[1,4]dioxin-6-yl)-2-oxo-octahydro-pyrido[4,3-e][1,3]oxazin-7-ylmethyl]-9-fluoro-1,2-dihydro-pyrrolo[3,2,1-ij]quinolin-4-one;

4-[(4aR*,8aR*)-3-(2,3-dihydro-benzo[1,4]dioxin-6-yl)-2-oxo-octahydro-pyrido[4,3-e][1,3]oxazin-7-ylmethyl]-3-fluoro-4,5-dihydro-pyrrolo[3,2,1-de][1,5]naphthyridin-7-one;

(4aR*,8aR*)-7-(2-(7-methoxy-2-oxo-1,8-naphthyridin-1(2H)-yl)ethyl)-3-(3-oxo-3,4-dihydro-2H-benzo[b][1,4]thiazin-6-yl)octahydro-2H-pyrido[4,3-e][1,3]oxazin-2-one;

(4aR*,8aR*)-7-((2RS)-2-(3-fluoro-6-methoxy-1,5-naphthyridin-4-yl)-2-hydroxyethyl)-3-(3-oxo-3,4-dihydro-2H-benzo[b][1,4]oxazin-6-yl)octahydro-2H-pyrido[4,3-e][1,3]oxazin-2-one;

(4aR*,8aR*)-7-(((R)-9-fluoro-4-oxo-2,4-dihydro-1H-pyrrolo[3,2,1-ij]quinolin-2-yl)methyl)-3-(3-oxo-3,4-dihydro-2H-pyrido[3,2-b][1,4]oxazin-6-yl)octahydro-2H-pyrido[4,3-e][1,3]oxazin-2-one; or (4aR*,8aR*)-7-(2-(7-methoxy-2-oxo-1,8-naphthyridin-1(2H)-yl)ethyl)-3-oxo-3,4-dihydro-2H-benzo[b][1,4]oxazin-6-yl)octahydro-2H-pyrido[4,3-e][1,3]oxazin-2-one;

or a salt of the compound.

11. A pharmaceutical composition comprising as an active principle the compound according to claim 1, or a pharmaceutically acceptable salt thereof, and at least one therapeutically inert excipient.

12. A method of treating a bacterial infection comprising administering to a subject in need thereof an effective amount of the compound according to claim 1, wherein the bacterial infection is a respiratory tract infection, otitis media, meningitis, skin and soft tissue infection, pneumonia, bacteremia, endocarditis, intraabdominal infection, gastrointestinal infection, *Clostridium difficile* infection, urinary tract infection, sexually transmitted infection, foreign body infection, osteomyelitis, lyme disease, topical infection, opthalmological infection, tuberculosis, tropical disease or combinations thereof.

13. The method according to claim 12, wherein the bacterial infection is respiratory tract infection, otitis media, meningitis, skin and soft tissue infection, pneumonia, bacteremia, or combinations thereof.

14. The method according to claim 12, wherein the bacterial infection is caused by *Staphylococcus aureus*.

15. A method of treating a bacterial infection caused by *Staphylococcus aureus* bacteria comprising administering to a subject in need thereof an effective amount of the compound according to claim 1.

* * * * *